United States Patent [19]

Lang et al.

[11] Patent Number: 4,845,118

[45] Date of Patent: Jul. 4, 1989

[54] SUBSTITUTED THIENOIMIDAZOLE DERIVATIVES, PHARMACEUTICAL COMPOSITIONS CONTAINING THEM, AND THEIR USE AS INHIBITORS OF GASTRIC ACID SECRETION

[75] Inventors: Hans-Jochen Lang; Robert Rippel, both of Hofheim am Taunus; Andreas W. Herling, Dreieich; Klaus Weidmann, Kronberg/Taunus, all of Fed. Rep. of Germany

[73] Assignee: Hoechst Aktiengesellschaft, Frankfurt am Main, Fed. Rep. of Germany

[21] Appl. No.: 136,360

[22] Filed: Dec. 22, 1987

Related U.S. Application Data

[63] Continuation-in-part of Ser. No. 16,139, Feb. 18, 1987, abandoned.

[30] Foreign Application Priority Data

Feb. 20, 1986 [DE] Fed. Rep. of Germany ....... 3605395
Jul. 12, 1986 [DE] Fed. Rep. of Germany ....... 3623683
Jan. 9, 1987 [DE] Fed. Rep. of Germany ....... 3700436

[51] Int. Cl.[4] .................... A61K 31/44; A61K 31/38; A61K 31/47; C07D 405/14
[52] U.S. Cl. .................... 514/338; 514/212; 514/228.5; 514/234.2; 514/253; 514/254; 514/299; 514/312; 514/313; 514/314; 540/597; 544/60; 544/61; 544/62; 544/124; 544/127; 544/128; 544/360; 544/361; 544/362; 544/363
[58] Field of Search .......... 546/271; 514/338

[56] References Cited

FOREIGN PATENT DOCUMENTS

| | | | |
|---|---|---|---|
| 57164/86 | 11/1986 | Australia ............ | 546/271 |
| 0005129 | 4/1981 | European Pat. Off. ........... | 546/271 |
| 176308 | 4/1986 | European Pat. Off. ........... | 546/271 |
| 201094 | 12/1986 | European Pat. Off. ........... | 546/271 |
| 237248 | 9/1987 | European Pat. Off. ........... | 546/271 |
| 2548340 | 7/1977 | Fed. Rep. of Germany ...... | 546/271 |
| 3240248 | 6/1983 | Fed. Rep. of Germany ...... | 546/271 |

OTHER PUBLICATIONS

The Peptides, Schroder et al., vol. I, pp. 177–181 (1965).

Primary Examiner—Mary C. Lee
Assistant Examiner—J. Richter
Attorney, Agent, or Firm—Finnegan, Henderson, Farabow, Garrett and Dunner

[57] ABSTRACT

The invention relates to compounds of the formula

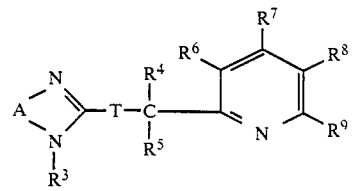

in which
A represents

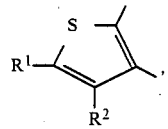
(a)

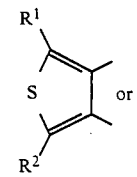

(b)

or

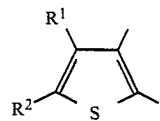
(c)

T denotes —S—, —SO— or —SO$_2$—, and
$R^1$ to $R^9$ have the meanings given in the description, to a process for their preparation, to pharmaceutical compositions containing them, and to their use as inhibitors of gastric acid secretion.

21 Claims, No Drawings

SUBSTITUTED THIENOIMIDAZOLE DERIVATIVES, PHARMACEUTICAL COMPOSITIONS CONTAINING THEM, AND THEIR USE AS INHIBITORS OF GASTRIC ACID SECRETION

This application is a continuation-in-part application of Ser. No. 016,139 filed Feb. 18, 1987 now abandoned by Hans-Jochen Lang et al.

Benzimidazole derivatives having an action inhibiting gastric acid secretion are disclosed in, for example, German Pat. No. A-25 48 340, European Pat. No. A-5129 and German Pat. No. A-32 40 248. European Pat. No. A-176 308 (laid open on Apr. 2, 1986) relates to N-substituted benzimidazole derivatives.

The present invention relates to thienoimidazole derivatives of the formula I

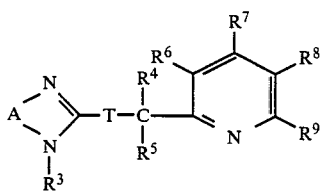     (I)

in which

A represents

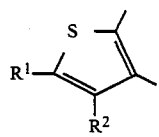     (a)

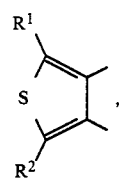     (b)

or

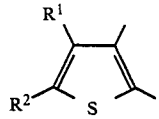     (c)

T denotes —S—, —SO— or —SO$_2$—, $R^1$ and $R^2$ are identical or different and denote hydrogen, halogen, cyano, nitro, (C$_1$-C$_6$)-alkyl, (C$_1$-C$_6$)-hydroxyalkyl, (C$_1$-C$_6$)-alkoxy, —O[—CH$_2$]$_x$—C$_f$H$_{(2f+1-g)}$F$_g$, preferably trifluormethyl or (C$_1$-C$_4$)-Fluoralkyl, —OCF$_2$Cl, O—CF$_2$—CHFCl, (C$_1$-C$_6$)-alkylmercapto, (C$_1$-C$_6$)-alkylsulfinyl, (C$_1$-C$_6$)-alkylsulfonyl, (C$_1$-C$_6$)-alkylcarbonyl, (C$_1$-C$_6$)-alkoxycarbonyl, carbamoyl, N-(C$_1$-C$_4$)-alkylcarbamoyl, N,N-di-(C$_1$-C$_4$)-alkylcarbamoyl, (C$_1$-C$_6$)-alkylcarbonyloxy, (C$_3$-C$_8$)-cycloalkyl, phenyl, benzyl, phenoxy, benzyloxy, anilino, N-methylanilino, phenylmercapto, phenylsulfonyl, phenylsulfinyl, sulfamoyl, N-(C$_1$-C$_4$)-alkylsulfamoyl or N,N-di-(C$_1$-C$_4$)-alkylsulfamoyl or, if A is as defined above under (a) or (c), can also together denote —[CH$_2$]$_n$— or —CH=CH—CH=CH—, one CH$_2$ group optionally being replaced by O, S, SO or SO$_2$, $R^3$ denotes hydrogen, alkanoyl, (C$_1$-C$_6$)-alkylcarbamoyl or another physiologically tolerated N$^{im}$ protective group which can be eliminated, preferably in an acid medium and/or under physiological conditions, $R^4$ and $R^5$ are identical or different and denote hydrogen or (C$_1$-C$_3$)-alkyl, $R^6$, $R^7$, $R^8$ and $R^9$ are identical or different and denote hydrogen, halogen, (C$_1$-C$_{12}$)-alkyl, (C$_1$-C$_{12}$)-alkoxy, —O[—CH$_2$]$_x$—C$_f$H$_{(2f+1-g)}$F$_g$, -NR'R", (C$_1$-C$_{12}$)-alkoxy-(C$_1$-C$_{12}$)-alkyl, (C$_1$-C$_{12}$)-alkoxy-(C$_1$-C$_{12}$)-alkoxy, (C$_7$-C$_{11}$)-aralkyloxy, (C$_1$-C$_{12}$)-alkylmercapto, (C$_1$-C$_{12}$)-alkylsulfinyl or (C$_1$-C$_{12}$)-alkylsulfonyl, or $R^5$ and $R^6$ together represent —[CH$_2$]$_i$—, R' and R" are identical or different and denote hydrogen or (C$_1$-C$_4$)-alkyl, or R' and R" together represent —[CH$_2$]$_h$— in which one CH$_2$ group can be replaced by O, S, N-(C$_1$-C$_4$)-alkanoylimino or N-(C$_1$-C$_4$)-alkoxycarbonylimino, f is an integer from 1 to 10, preferably from 1 to 4, g is 1 to (2f+1), h is 4, 5 or 6, i is 1, 2 or 3, x is 0 or 1, preferably 1, and n is 3 or 4, and to their physiologically tolerated salts.

1H-Thieno[3,4-d]imidazole derivatives of the formula I in which A is as defined above under (b) are preferred. In addition, compounds of the formula I in which $R^9$ represents hydrogen are preferred. T is preferably a —SO— group.

Particularly preferred compounds of the formula I are those in which

A is preferably as defined above under (b),

T preferably denotes a —SO— group, $R^1$ and $R^2$ are identical or different and denote hydrogen, (C$_1$-C$_3$)-alkyl, halogen, (C$_1$-C$_4$)-alkoxy or (C$_1$-C$_4$)-alkoxycarbonyl, $R^3$ is as defined above, $R^4$ and $R^5$ each denote hydrogen, and/or $R^6$, $R^7$, $R^8$ and $R^9$ are identical or different and denote hydrogen, halogen, —O[—CH$_2$]$_x$—C$_f$H$_{(2f+1-g)}$F$_g$, (C$_1$-C$_3$)-alkyl (C$_1$-C$_4$)-alkoxy, benzyloxy or (C$_1$-C$_7$)-alkoxy-(C$_1$-C$_3$)-alkyl, $R^9$ preferably representing hydrogen, and halogen preferably denoting chlorine or bromine, but especially preferred compounds of the formula I are those in which A is preferably as defined above under (b), T preferably denotes a —SO— group, $R^1$ and $R^2$ are identical or different and denote hydrogen or (C$_1$-C$_3$)-alkyl, $R^3$ is as defined above, $R^4$ and $R^5$ each denote hydrogen, $R^6$ and $R^8$ are identical or different and denote hydrogen, chlorine, methyl or ethyl, $R^9$ denotes hydrogen and/or $R^7$ denotes hydrogen, —O—[CH$_2$]$_x$C$_f$H$_{(2f+1-g)}$F$_g$, (C$_1$-C$_4$)-alkoxy, (C$_1$-C$_3$)-alkyl or benzyloxy.

The following are of particular importance:

2-(2-Picolylsulfinyl)-1H-thieno[3,4-d]imidazole;

2-(4-methoxy-2-picolylsulfinyl)-1H-thieno[3,4-d]imidazole;

2-(4-methoxy-3-methyl-2-picolysulfinyl)-1H-thieno[3,4-d]imidazole;

2-(4-methoxy-3,5-dimethyl-2-picolylsulfinyl)-1H-thieno[3,4-d]imidazole;

2-(3-methyl-2-picolysulfinyl)-1H-thieno[3,4-d]imidazole;

2-(5-methyl-2-picolylsulfinyl)-1H-thieno[3,4-d]imidazole;

2-(4-methyl-2-picolylsulfinyl)-1H-thieno[3,4-d]imidazole;

2-(5-ethyl-2-picolylsulfinyl)-1H-thieno[3,4-d]imidazole;

4,6-dimethyl-2-(5-methyl-2-picolylsulfinyl)-1H-thieno[3,4-d]imidazole;

2-(3-chloro-4-methoxy-2-picolylsulfinyl)-1H-thieno[3,4-d]imidazole,

2-[4-(2,2,3,3,4,4,5,5-octafluoropentyloxy)-2-picolylsulfinyl]-1H-thieno[3,4-d]imidazole;

2-[4-(2,2,3,3,4,4,4-heptafluorobutyloxy)-2-picolylsulfinyl]-4,6-dimethyl-1H-thieno[3,4-d]imidazole;

2-[4-(2,2,2-trifluoroethyloxy)-2-picolylsulfinyl]-4,6-dimethyl-1H-thieno[3,4-d]imidazole;

2-[4-(2,2,3,3-tetrafluoropropyloxy)-2-picolylsulfinyl]-4,6-dimethyl-1H-thieno[3,4-d]imidazole;

2-[4-(2,2,3,3,3-pentafluoropropyloxy)-2-picolylsulfinyl]-4,6-dimethyl-1H-thieno[3,4-d]imidazole;

2-[3-methyl-4-(2,2,2-trifluoroethyloxy)-2-picolylsulfinyl]-1H-thieno[3,4-d]imidazole;

2-[5-methyl-4-(2,2,2-trifluoroethyloxy)-2-picolylsulfinyl]-1H-thieno[3,4-d]imidazole;

4-[3-methyl-(2,2,3,3,3-pentafluoropropyloxy)-2-picolylsulfinyl]-1H-thieno[3,4-d]imidazole;

2-[3-methyl-4-(2,2,3,3,4,4,4-heptafluorobutyloxy)-2-picolylsulfinyl-1H-thieno[3,4-d]imidazole;

2-[4-(2,2,2-trifluoroethyloxy)-2-picolylsulfinyl]-1H-thieno[3,4-d]imidazole;

2-[4-(2,2,3,3-tetrafluoropropyloxy)-2-picolylsulfinyl]-1H-thieno[3,4-d]imidazole;

2-[4-(2,2,3,3,3-pentafluoropropyloxy)-2-picolylsulfinyl]-1H-thieno[3,4-d]imidazole;

Alkyl and radicals derived therefrom, such as, for example, alkoxy, alkylmercapto, alkylsulfinyl, alkylsulfonyl, aralkyl or alkanoyl, can be straight-chain or branched.

$(C_6-C_{12})$-Aryl is, for example, phenyl, naphthyl or biphenylyl, and is preferably phenyl.

$(C_7-C_{11})$-Aralkyl is, for example, benzyl or phenethyl, preferably benzyl. A corresponding statement applies to radicals derived therefrom, such as aralkyloxy.

Halogen represents fluorine, chlorine, bromine or iodine.

$C_fH_{(2f+1-g)}F_g$ is a straight-chain or branched fluorinated alkylradical.

$R^3$ preferably represents hydrogen, $(C_1-C_6)$-alkylcarbamoyl or a radical of the formula VI

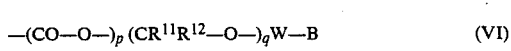

in which p denotes 0 or 1, q denotes 0 or 1, and B denotes hydrogen, an acyl radical or an optionally substituted alkyl radical.

$R^{11}$ and $R^{12}$ are identical or different and denote hydrogen, $(C_1-C_6)$-alkyl, $(C_3-C_8)$-cycloalkyl, $(C_7-C_{11})$-aralkyl or $(C_6-C_{12})$-aryl.

B and $R^{11}$ can also together represent a $-[CH_2]_r-$ chain with r being 3, 4 or 5, preferably 4, it being possible on one or more of the $CH_2$ groups for one hydrogen atom in each case to be replaced by OH, protected OH, amino, acylamino and/or halogen. A radical having a substituted $-[CH_2]_r-$ chain is preferably a glycosyl radical which is derived from a glycopyranose, glycofuranose or an oligosaccharide and is optionally partially or completely protected by protective groups customary in carbohydrate chemistry.

Both α- and β-glycosidic linkage of the glycosyl radical is possible.

It can be, for example, a glucofuranosyl or glucopyranosyl radical which derives from naturally occurring aldotetroses, aldopentoses, aldohexoses, ketopentoses, deoxyaldoses, aminoaldoses and oligosaccharides such as disaccharides and trisaccharides, as well as their stereoisomers.

These glycosyl radicals are derived, in particular, from natural D- or L-monosaccharides which occur in microorganisms, plants, animals or humans, such as ribose (Rib), arabinose (Ara), xylose (Xyl), lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc) or disaccharides such as maltose (Mal), lactose (Lac), cellobiose (Cel), gentiobiose (Gen), N-acetyllactosamine (LacNAc), chitobiose (Chit), β-galactopyranosyl-(1-3)-N-acetylgalactosamine and β-galactopyranosyl-(1-3)- or -(1-4)-N-acetylglucosamine, as well as their synthetic derivatives such as 2-deoxy-, 2-amino-, 2-acetamido-or 2-halogeno-, preferably bromo- or iodo-sugars.

Protective groups customary in carbohydrate chemistry are particularly understood to be, for example, the $(C_1-C_{10})$-acyl protective groups such as $(C_1-C_6)$-alkanoyl (for example acetyl, trichloroacetyl and trifluoroacetyl), benzoyl or p-nitrobenzoyl, as well as optionally modified methyl, methyloxymethyl, benzyl, tetrahydropyranyl, benzylidene, isopropylidene or trityl group, preference being given here to the acyl protective groups, in particular the acetyl (Ac) group.

(a) Where p and q are 0, the radicals preferably have the following meanings:

W is a bond or denotes $-CO-$, $-CR^{13}R^{14}-$ or $-CO-CR^{13}R^{14}-$;

B denotes hydrogen (only if W is not a bond), $(C_1-C_{10})$-alkyl; $(C_2-C_{12})$-alkenyl; $(C_3-C_{12})$-cycloalkyl;

$(C_6-C_{12})$-aryl which is optionally substituted by 1, 2 or 3 identical or different radicals from the series comprising $(C_1-C_4)$-alkyl, chlorine, bromine, fluorine, nitro, trifluoromethyl, $(C_1-C_4)$-alkoxy and hydroxyl; $-(CH_2)_s-CH(NH_2)-R^{15}$ with s=1-9; the acyl radical of an amino acid, or $(C_1-C_6)$-alkyl which is substituted by up to 4 identical or different radicals from the series comprising F, Cl or Br.

$R^{13}$ and $R^{14}$ are identical or different and denote hydrogen, $(C_1-C_6)$-alkyl, $(C_1-C_6)$-alkoxy, $(C_3-C_8)$-cycloalkyl, $(C_7-C_{11})$-aralkyl, $(C_6-C_{12})$-aryl or pyridyl, or $R^{13}$ and $R^{14}$ together represent $-[CH_2]_4-$, $-[CH_2]_5-$ or $-[CH_2]_6-$, in which 1 or 2 $CH_2$ groups can be replaced by 0.

$R^{15}$ denotes hydrogen or $(C_1-C_{10})$-alkyl.

(b) Where q is 1, W and B are as defined above under (a). In addition, W can denote $-CO-O-$ and —CO—O—CR$^{13}$—R$^{14}$—, R$^{13}$ and R$^{14}$ having the abovementioned meanings. B can also represent hydrogen in the case where W is a bond.

(c) Where p is 1 and q is 0, W represents a bond or denotes —CR$^{13}$R$^{14}$—, R$^{13}$ and R$^{14}$ having the meanings as under (a). B is defined as under (a), but cannot represent the acyl radical of an amino acid. In addition, —CO—O—W—B can represent other N$^{im}$ protective groups of the urethane type which are not embraced by the above-mentioned definition (cf. for example Hubbuch, Kontakte Merck 3/79 14–23; Büllesbach, Kontakte Merck 1/80 23-35).

An optionally substituted ($C_6$-$C_{12}$)-aryl radical (see above under (a)) is to be understood to be, for example, phenyl, (o-, m-, p-)tolyl, (o-, m-, p-)ethylphenyl, 2-ethyltolyl, 4-ethyl-o-tolyl, 5-ethyl-m-tolyl, (o-, m- or p-)propylphenyl, 2-propyl-(o-, m- or p-)tolyl, 4-isopropyl-2,6-xylyl, 3-propyl-4-ethylphenyl, (2,3,4-, 2,3,6- or 2,4,5-)trimethylphenyl, (o-, m- or p-)fluorophenyl, (o-, m- or p-trifluoromethyl)phenyl, 4-fluoro-2,5-xylyl, (2,4-, 2,5-, 2,6-, 3,4- or 3,5-)difluorophenyl, (o-, m- or p-) chlorophenyl, 2-chloro-p-tolyl, (3-, 4- or 5-or 6-)chlorotolyl, 4-chloro-2-propylphenyl, 2-isopropyl-4-chlorophenyl, 4-chloro-3,5-xylyl, (2,3-, 2,4-, 2,5-, 2,6- or 3,5-)dichlorophenyl, 4-chloro-3-fluorophenyl, (3- or 4-)chloro-2-fluorophenyl, (o-, m- or p-)trifluoromethylphenyl, (o-, m- or p-)ethoxyphenyl, (4- or 5-)chloro-2-methoxyphenyl, 2,4-dichloro-(5- or 6-)methylphenyl or (o-, m- or p-)methoxyphenyl.

($C_1$-$C_{10}$)-Alkyl is, for example, methyl, ethyl, propyl, butyl, pentyl, hexyl, heptyl, octyl, nonyl, decyl or their isomeric forms.

($C_3$-$C_{12}$)-Cycloalkyl also includes alkyl-substituted cycloalkyl and bicyclic and polycyclic systems. It is to be understood to include, for example: cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, 2,2-dimethylcyclohexyl, cycloheptyl, cyclononyl, cyclodecyl, norbornyl or adamantyl.

An acyl radical of an amino acid is to be understood to be, preferably, the radical of an α-amino acid, in particular from the series of naturally occurring α-amino acids or their antipodes, such as, for example, H-Gly, H-Ala, H-Val, H-Leu, H-Ile, H-Phe, H-Lys, H-Pro, H-Trp, H-Met, H-Ser, H-Thr, H-Cys, H-Tyr, H-Asn, H-Gln, H-Asp, H-Glu, H-Arg, H-Orn, or the corresponding radicals in the D configuration.

Without confining the subject-matter of the invention to them, a few urethane protective groups R$^3$=—CO—O—WB according to the invention may be mentioned hereinafter. ($C_1$-$C_6$)-Alkoxycarbonyl such as Boc; ($C_3$-$C_{12}$)-cycloalkyloxycarbonyl such as Mboc, Iboc or Adoc;

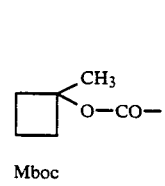

Mboc

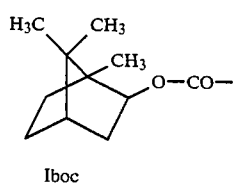

Iboc

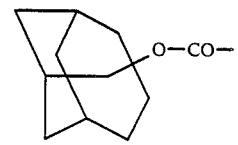

Adoc ($C_3$-$C_{12}$)-cycloalkyl-($C_1$-$C_6$)-alkoxycarbonyl such as Adpoc;

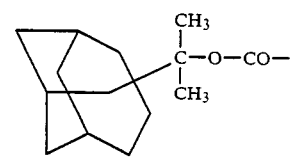

Adpoc ($C_6$-$C_{12}$)-aryl-($C_1$-$C_6$)-alkoxycarbonyl such as Z, Fmoc or Bpoc,

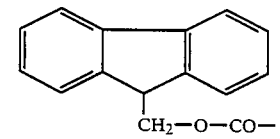

Fmoc

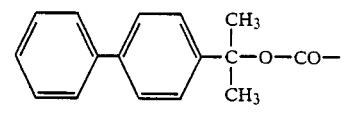

Bpoc substituted Z radicals such as Moc, Ddz and Z (p—NO$_2$)

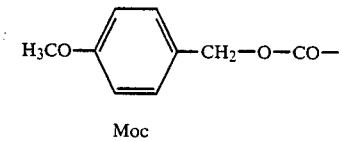

Moc

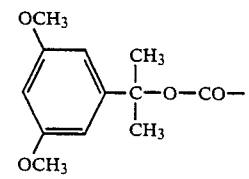

Ddz and modified Z radicals such as Pyoc and their radicals derived from 2- and 3-picoline, which can be substituted as indicated above for ($C_6$-$C_{12}$)-aryl.

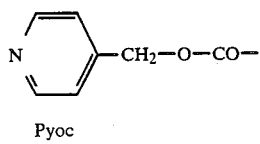

Pyoc

Preferred N$^{im}$ protective groups are those which can be eliminated in the presence of acids, preferably in a pH range of about 1–6 and/or under physiological conditions.

It is surprising that compounds of the formula I with R$^3 \neq$H are much more stable than the corresponding compounds with R$^3$=H. In particular, they are more stable under acid conditions, as prevail in, for example, the stomach, and in the presence of water. Thus, by specific selection of an N$^{im}$ protective group it is possible for those skilled in the art to control the release of the active compounds in such a way that this takes place selectively at the site of action.

Chiral carbon and sulfur atoms which are present where appropriate can exist both in the R and in the S configuration. In such cases, compounds of the formula I are in the form of the pure enantiomers or a mixture of stereoisomers (such as a mixture of enantiomers and a mixture of diastereomers).

Suitable salts are, in particular, alkali metal and alkaline earth metal salts and salts with physiologically tolerated amines.

The invention also relates to a process for the preparation of compounds of the formula I, which comprises
(a) reaction of compounds of the formula II

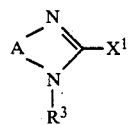 (II)

in which A, R$^1$, R$^2$ and R$^3$ are as defined above, and X$^1$ denotes
 i. a leaving group or
 ii. —SH, —S$^-$ or —SO$_2^-$,
with compounds of the formula III

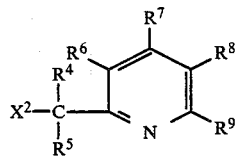 (III)

in which R$^4$, R$^5$, R$^6$, R$^7$, R$^8$ and R$^9$ are as defined above and X$^2$ in the abovementioned case
 i. denotes —SH, —S$^-$ or —SO$_2^-$ and in the abovementioned case
 ii. denotes a leaving group or
(b) reaction of compounds of the formula IV

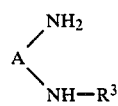 (IV)

in which A, R$^1$, R$^2$ and R$^3$ are as defined above, with compounds of the formula V

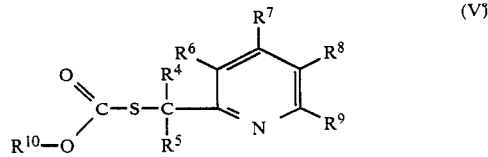 (V)

in which R$^4$, R$^5$, R$^6$, R$^7$, R$^8$ and R$^9$ are as defined above and R$^{10}$ represents an esterifying group, and
 i. if desired, oxidation of (an) —S— group(s) which are (is) present, where appropriate, in compounds of the formula I to (an) —SO— or —SO$_2$— group(s),
 ii. if desired, oxidation of (an) —SO— group(s) which are (is) present, where appropriate, in compounds of the formula I to (an) —SO$_2$— group(s),
 iii. if desired, acylation, alkylation or aralkylation of compounds of the formula I in which R$^3$ denotes hydrogen, and
 iv. if desired, hydrolysis of compounds of the formula I in which R$^3$ does not denote hydrogen, and
 v. if desired, conversion of compounds of the formula I into their physiologically tolerated salts,
it also being possible for two or more of measures i.-iv. to be carried out in a sequence different from that indicated.

If, in accordance with process variant (a), which is preferred in this connection, compounds of the formula II are reacted with compounds of the formula III, then X$^1$ or X$^2$ represents a leaving group which can be removed nucleophilically, such as Cl, Br, I, —O—SO$_2$—CH$_3$, —O—SO$_2$—CF$_3$ or —O—SO$_2$—(C$_6$H$_4$—pCH$_3$).

The reaction of a compound of the formula II with a compound of the formula III or its salts is carried out in an inert solvent such as, for example, water, methylene chloride, methanol, ethanol, acetone, ethyl acetate, toluene, tetrahydrofuran, acetonitrile, dimethylformamide, dimethyl sulfoxide or mixtures of these solvents, advantageously in the presence of an inorganic or organic base such as, for example, sodium or potassium hydroxide, carbonate, alkoxide, hydride or amide, ammonia, triethylamine, tributylamine or pyridine, at −20° to +150° C., preferably at 0°–80° C.

The compounds of the formula II can be prepared in analogy to known processes, for example by ring closure of appropriately substituted 2,3-, 3,4- or 4,5-diaminothiophenes of the formula IV defined above with appropriate sulfur compounds such as carbon disulfide (for example German Pat. No. A-31 32 167).

The 2,3-, 3,4- or 4,5-diaminothiophenes required for this purpose are either known from the literature or can be prepared in analogy to known processes. They are obtained by, for example, reduction of appropriately substituted aminonitrothiophenes.

R$^{10}$ in the esters of the formula V used in process variant (b) represents an esterifying group, preferably (C$_1$-C$_6$)-alkyl or benzyl.

The reaction of a compound of the formula IV with a compound of the formula V in accordance with process variant (b) is carried out in analogy to the procedures described in Preston et al., Benzimidazoles and Congeneric Tricyclic Compounds, Part 1, New York, pages 10–13.

The compounds of the formula I thus obtained can, if R³ denotes hydrogen, be converted into physiologically tolerated salts.

Compounds of the formula I with T=—S— can, furthermore, be converted into those with T=—SO— or —SO₂— using suitable oxidizing agents. It is also possible in the same manner to oxidize —S— groups in the substituents R¹, R² and R⁶ to R⁹.

This reaction is carried out in a suitable inert solvent such as, for example, methylene chloride, chloroform, carbon tetrachloride, 1,2-dichloroethane, toluene, ethyl acetate, acetic acid, trifluoroacetic acid, water, methanol, ethanol or mixtures thereof, at −20° C. to +150° C., preferably at −10° C. to +40° C.

Examples of suitable oxidizing agents are: hydrogen peroxide, peracids and peresters, such as peracetic acid, trifluoroperacetic acid, monoperphthalic acid, m-chloroperbenzoic acid and their esters, ozone, dinitrogen tetroxide, iodosobenzene, N-chlorosuccinimide, 1-chlorobenzotriazole, sodium hypochlorite, potassium peroxodisulfate, t-butyl hypochlorite, tetrabutylammonium periodate or permanganate, sodium metaperiodate, selenium dioxide or manganese dioxide, ceric ammonium nitrate, chromic acid, chlorine, bromine, diazabicyclo[2.2.2]octanebromine bromine complex, dioxane dibromide, pyridinium perbromide, sulfuryl chloride, 2-arylsulfonyl-3-aryloxaziridines, titanium tetraisopropylate/tert.-butyl hydroperoxide (where appropriate with the addition of dialkyl esters of (D)- or (L)-tartaric acid and a defined amount of water).

It is likewise possible to use isolated, where appropriate immobilized, oxidizing enzymes or microorganisms as oxidizing agents.

The oxidizing agents are used in equimolar amounts, and optionally in a small excess of 5-10 mol % in the oxidation to T=—SO—, or in larger excess and/or at a higher reaction temperature when oxidation to T=—SO₂— is desired.

Compounds of the formula I with R³≠H can be prepared starting from compounds of the formula IV with R³=H and compounds of the formula V, or by acylation, alkylation or aralkylation of compounds of the formula I with R³=H. The second route will be dealt with in some detail hereinafter.

The acylation, alkylation or aralkylation of compounds of the formula I is carried out in a manner known per se using the appropriate acylating agents, alkylating agents or aralkylating agents in a suitable organic solvent, as a rule at a temperature between −78° C. and the boiling point of the reaction mixture, where appropriate in the presence of a base.

N$^{im}$ protective groups of the formula VI with p=O, q=1, W=bond and B=hydrogen can be introduced into compounds of the formula I (R³=H, T=S) by, for example, hydroxyalkylation, it being possible to introduce N$^{im}$ protective groups with R¹¹=R¹²=hydrogen in a manner known per se (cf. for example Eur. J. Med. Chem. 15 [1980] 586; J. Med. Chem. 22 [1979] 1113) by hydroxymethylation with formaldehyde in an organic solvent such as, for example, acetonitrile. The hydroxyalkylation is carried out at a temperature between 0° C. and the boiling point of the reaction mixture, where appropriate in the presence of a base such as triethylamine.

Hydroxymethyl compounds of the formula VII

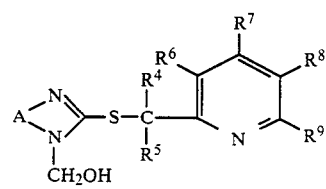

can be converted in the manner described in European Pat. No. A-176308, page 11, into acyl derivatives of the formula VIII

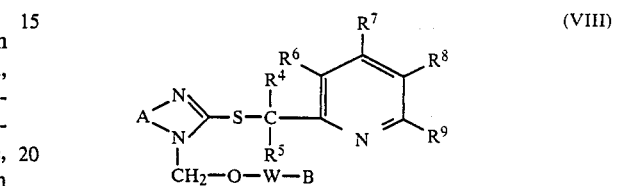

in which W—B is an acyl radical.

Compounds of the formula I with R³=H can also be alkylated with reagents of the formula IX

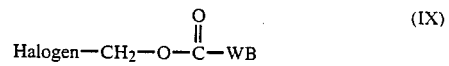

such as, for example, chloromethyl pivalate, in a known manner, the corresponding carbonates (W=—CO—O— or —CO—O—CR¹³R¹⁴—) being obtained. The reaction is carried out in the manner described in, for example, European Pat. No. A-176308, page 12.

Acyl radicals of amino acids are coupled onto compounds of the formula I with R³=H in a known manner (for example the DCC/HOBt or dialkylphosphinic anhydride method).

N$^{im}$ protective groups of the formula VI with p=0, q=1 and R¹¹ and/or R¹²≠hydrogen are introduced by reacting a compound of the formula I (R³=H, T=S) with 1 to 10 equivalents, preferably 2 to 3 equivalents, of the corresponding α-halogenoalkyl ester. The α-halogenoalkyl esters which are used are obtained from acid halides and aldehydes by known methods (cf. for example J. Amer. Chem. Soc. 43 [1921] 660; J. Med. Chem. 23 [1980] 469-474).

Bromoalkyl esters are preferably used. Alternatively, it is possible to treat the anion of a compound of the formula I (R³=H, T=S), which can be obtained from the latter and NaH, with the α-halogenoalkyl ester.

It is also possible in place of the α-halogenoalkyl esters to use (1-alkylcarbonyloxyalkyl)pyridinium salts which are prepared in analogy to the known (1-arylcarbonyloxyalkyl)pyridinium salts (cf. Angew. Chem. Suppl. 1982, 675-685) from the corresponding acyl halides, aldehydes and pyridine.

Alkylamino acetals of the formula I in which R³ represents a radical of the formula VI in which p is 0, q is 1 and W denotes a bond or —CR¹³R¹⁴—, and B has the abovementioned meaning, are prepared by treating a compound of the abovementioned formula I (R³=H, T=S) in a dipolar aprotic solvent such as dimethylformamide, at about 20° to 50° C., preferably at about 25° C., with about one equivalent of NaH. The anion which is thus obtained is then reacted with about one equivalent of a halogeno ether of the formula halogen- CR¹¹R¹²—W—B (halogen=chlorine or bromine), the reaction mixture being stirred at about 20° to 50° C., preferably at about 25° C., for 15 minutes. The halogeno ethers are known and many of them are commercially available or can be prepared in analogy to known compounds.

Urethanes of the formula I in which $R^3$ represents a urethane protective group of the formula VI (p=1, q=0 and W=bond or —CR¹³R¹⁴—) are obtained from the corresponding compounds with $R^3$=H by reacting the latter, where appropriate in the presence of a base such as NaH, in a suitable solvent such as DMF, with esters of fluoroformic or chloroformic acid of the formula Cl(F)—CO—O—WB (in analogy to the procedure described in European Pat. No. A-176308, page 12).

The fluoroformates and chloroformates are known and are often commercially available or can be prepared by known methods.

Aralkyloxycarbonyl and alkoxycarbonyl groups can also be introduced using the known dicarbonates, which can often be bought, such as di-tert.-butyl decarbonate and dibenzyl dicarbonate.

Substituted or modified Z groups in which $R^{13}$ and/or $R^{14}$ are not hydrogen are prepared by reaction of the corresponding unprotected compound of the formula I, if necessary with the assistance of a base, with the appropriate azides or the appropriate carbonates.

It is possible to use for acylation of the compounds of the formula I ($R^3$=H, T=S) not only the customary standard conditions (for example acetic anhydride, triethylamine, dimethylaminopyridine) but also other processes such as, for example, reaction with N-(1-arylcarbonyloxyalkyl)pyridinium salts (known from Angew. Chem. Suppl. 1982, 675–685).

To prepare dialkoxy derivatives of the formula I ($R^3$=—CR¹³R¹⁴—B in which $R^{13}$ and $R^{14}$ each denote alkoxy or together denote alkylenedioxy and B denotes H; T=S or SO) preferably the corresponding compound of the formula I with $R^3$=H is reacted, in the presence of a base, with the appropriate orthoformic esters such as trialkyl orthoformates.

Apart from the thienoimidazole derivatives described in the exemplary embodiments, it is also possible to obtain according to the invention, for example, the compounds of the general formula I, or their salts, which are compiled in Table 1 which follows.

Abbreviations used: methyl (Me), ethyl (Et), propyl (Pr), butyl (Bu), hexyl (Hex), acetyl (Ac), phenyl (Ph), cyclo (c), iso (i).

TABLE 1

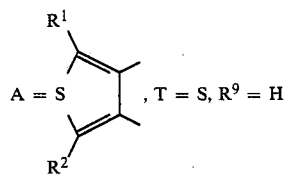

A = S, T = S, R⁹ = H

| R¹ | R² | R³ | R⁴ | R⁵ | R⁶ | R⁷ | R⁸ |
|---|---|---|---|---|---|---|---|
| H | H | H | H | Me | H | H | H |
| H | H | H | H | Me | H | OMe | H |
| H | H | H | H | Me | H | OEt | H |
| H | H | H | H | Me | Me | H | H |
| H | H | H | H | Me | Me | OMe | H |
| H | H | H | H | Me | Me | OMe | Me |
| H | H | H | H | Me | H | H | Me |
| H | H | H | H | Me | H | Me | H |
| H | H | H | H | H | Me | Me | H |
| H | H | H | H | H | Et | H | H |
| H | H | H | H | H | H | Et | H |
| H | H | H | H | H | H | Pr | H |
| H | H | H | H | H | H | H | Pr |
| H | H | H | H | H | H | H | Bu |
| H | H | H | H | H | Me | OEt | H |
| H | H | H | H | H | H | OPr | H |
| H | H | H | H | H | H | OBu | H |
| H | H | H | H | H | H | OHex | H |
| H | H | H | H | H | H | H | Hex |
| H | H | H | H | H | Me | Me | Me |
| H | H | H | H | H | H | O—iPr | H |
| H | H | H | H | H | H | iPr | H |
| H | H | H | H | H | H | H | iPr |
| H | H | H | H | H | Cl | H | H |
| H | H | H | H | H | H | Cl | H |
| H | H | H | H | H | H | H | Cl |
| H | H | H | H | H | Cl | H | Me |
| H | H | H | H | H | Cl | Me | H |
| H | H | H | H | H | H | Cl | Me |
| H | H | H | H | H | H | Me | Cl |
| H | H | H | H | H | Cl |  | H |

TABLE 1-continued $$A = S \begin{matrix} R^1 \\ \\ R^2 \end{matrix}, T = S, R^9 = H$$

| R¹ | R² | R³ | R⁴ | R⁵ | R⁶ | R⁷ | R⁸ |
|---|---|---|---|---|---|---|---|
| H | H | H | H | H | Cl | piperidin-1-yl | H |
| H | H | H | H | H | Cl | OEt | H |
| H | H | H | H | H | Cl | OPr | H |
| H | H | H | H | H | Cl | OBu | H |
| H | H | H | H | H | Cl | morpholin-4-yl | H |
| H | H | H | H | H | Cl | O—(CH₂)₂—OMe | H |
| H | H | H | H | H | Me | O—(CH₂)₂—OMe | H |
| H | H | H | H | H | H | O—(CH₂)₂—Ph | H |
| H | H | H | H | H | H | O—(CH₂)₃—Ph | H |
| H | H | H | H | H | H | OCH₂CF₃ | H |
| H | H | H | H | H | H | OCH₂(CF₂)₂CF₃ | H |
| H | H | H | H | H | H | OCH₂CF₂CF₃ | H |
| H | H | H | H | H | H | OCH₂—CF₂—CF₂H | H |
| H | H | H | H | H | Me | OCH₂—CF₃ | H |
| H | H | H | H | H | H | OCH₂CF₃ | Me |
| H | H | H | H | H | Cl | OCH₂CF₃ | H |
| H | H | H | H | H | Me | OCH₂mF₂CF₃ | H |
| Me | H | H | H | H | H | H | H |
| Me | H | H | H | H | H | OMe | H |
| Me | H | H | H | H | Me | OMe | H |
| Me | H | H | H | H | Me | OMe | Me |
| Me | H | H | H | H | Me | H | H |
| Me | H | H | H | H | H | Me | H |
| Me | H | H | H | H | H | H | Me |
| Me | H | H | H | H | H | H | Et |
| Me | H | H | H | H | H | O—CH₂—Ph | H |
| Me | H | H | H | H | Cl | piperidin-1-yl | H |
| Me | H | H | H | H | Cl | morpholin-4-yl | H |
| Me | H | H | H | H | Cl | H | H |
| Me | H | H | H | H | H | Cl | H |
| Me | H | H | H | H | Cl | Me | H |
| Me | H | H | H | H | H | OCH₂CF₃ | H |
| Me | H | H | H | H | Me | H | Me |
| Et | H | H | H | H | H | H | H |
| Et | H | H | H | H | H | OMe | H |
| Et | H | H | H | H | Me | H | H |
| Et | H | H | H | H | H | H | Me |
| i-Pr | H | H | H | H | H | H | H |
| i-Pr | H | H | H | H | H | OMe | H |
| i-Pr | H | H | H | H | H | H | Me |

TABLE 1-continued $A = S$ [thiophene structure with R¹, R²], $T = S$, $R^9 = H$

| R¹ | R² | R³ | R⁴ | R⁵ | R⁶ | R⁷ | R⁸ |
|---|---|---|---|---|---|---|---|
| —CH(OH)—Me | H | H | H | H | H | H | H |
| —CH(OH)—Me | H | H | H | H | H | OMe | H |
| —CH(OH)—Me | H | H | H | H | Me | H | H |
| —CH(OH)—Me | H | H | H | H | H | H | Me |
| —CH(OH)—Me | H | H | H | H | Me | H | Me |
| OMe | Me | H | H | H | H | H | H |
| OMe | Me | H | H | H | Me | OMe | Me |
| OMe | me | H | H | H | Me | H | H |
| OMe | Me | H | H | H | H | H | Me |
| OMe | Me | H | H | H | H | OMe | H |
| OMe | Me | H | H | H | H | Me | H |
| OMe | Me | H | H | H | Cl | morpholino | H |
| OMe | Me | H | H | H | Cl | H | H |
| OMe | Me | H | H | H | H | H | Et |
| OMe | Me | H | H | H | Me | H | Me |
| Me | Ac | H | H | H | H | H | Me |
| Me | Ac | H | H | H | H | OMe | H |
| Me | Ac | H | H | H | Me | OMe | Me |
| OEt | Me | H | H | H | H | H | H |
| OEt | Me | H | H | H | Me | OMe | Me |
| OEt | Me | H | H | H | H | OMe | H |
| OEt | Me | H | H | H | H | H | Me |
| OEt | Me | H | H | H | Me | H | H |
| OBu | Me | H | H | H | H | H | Me |
| OBu | Me | H | H | H | Me | OMe | Me |
| OMe | OMe | H | H | H | H | H | H |
| OMe | OMe | H | H | H | H | OMe | H |
| OMe | OMe | H | H | H | Me | OMe | Me |
| OMe | OMe | H | H | H | Me | H | H |
| OMe | OMe | H | H | H | H | Me | H |
| OMe | OMe | H | H | H | H | H | Me |
| OMe | OMe | H | H | H | H | H | Et |
| OMe | OMe | H | H | H | Cl | morpholino | H |
| OMe | OMe | H | H | H | Cl | OMe | H |
| OMe | Me | H | H | H | Cl | OMe | H |
| OMe | H | H | H | H | H | H | H |
| OMe | H | H | H | H | H | OMe | H |
| OMe | H | H | H | H | Me | OMe | Me |
| OMe | H | H | H | H | H | H | Me |
| OMe | H | H | H | H | H | Me | H |

TABLE 1-continued

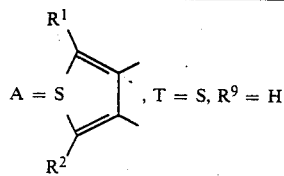

A = S, T = S, R⁹ = H

| R¹ | R² | R³ | R⁴ | R⁵ | R⁶ | R⁷ | R⁸ |
|---|---|---|---|---|---|---|---|
| OMe | H | H | H | H | Me | H | H |
| OMe | Cl | H | H | H | H | H | H |
| OMe | Cl | H | H | H | Me | OMe | Me |
| OMe | Cl | H | H | H | H | H | Me |
| PhSO₂ | PhSO₂ | H | H | H | H | H | |
| PhSO₂ | PhSO₂ | H | H | H | Me | OMe | |
| PhSO₂ | PhSO₂ | H | H | H | H | H | Me |
| NH—Ph | H | H | H | H | H | H | H |
| NH—Ph | H | H | H | H | Me | OMe | Me |
| NH—Ph | H | H | H | H | H | H | Me |
| NH—Ph | Cl | H | | | H | H | H |
| NH—Ph | Cl | H | | | Me | OMe | Me |
| NH—Ph | Cl | H | | | H | H | Me |
| O—Ph | H | H | H | H | H | H | H |
| O—Ph | H | H | H | H | Me | OMe | H |
| O—Ph | H | H | H | H | H | H | Me |
| O—Ph | Cl | H | H | H | H | H | H |
| Me | Me | H | H | H | H | H | Et |
| Me | Me | H | H | H | H | Et | H |
| Me | Me | H | H | H | Me | H | Me |
| Me | Me | H | H | H | Me | Me | Me |
| Me | Me | H | H | H | Cl | Me | H |
| Me | Me | H | H | H | Cl | OMe | H |
| Me | Me | H | H | H | Cl | H | H |
| Me | Me | H | H | H | Cl | Cl | H |
| Me | Me | H | H | H | Cl | piperidino | H |
| Me | Me | H | H | H | Cl | N-methylmorpholino | H |
| Me | Me | H | H | H | H | O—CH₂Ph | H |
| Me | Me | H | H | H | H | —O—CH₂—CF₃ | H |
| Me | Me | H | H | H | H | —O—CH₂—CF₂CF₃ | H |
| Me | Et | H | H | H | H | H | H |
| Me | Et | H | H | H | Me | OMe | Me |
| Me | Et | H | H | H | H | H | Me |
| Cl | COOMe | H | H | H | H | H | H |
| Cl | COOMe | H | H | H | Me | OMe | Me |
| Cl | COOMe | H | H | H | H | OMe | H |
| Cl | COOMe | H | H | H | H | H | Me |
| H | CONEt₂ | H | H | H | H | H | H |
| H | CONEt₂ | H | H | H | Me | OMe | Me |
| H | CONEt₂ | H | H | H | H | H | Me |
| H | CONH₂ | H | H | H | H | H | H |
| H | CONH₂ | H | H | H | Me | OMe | Me |
| H | CONH₂ | H | H | H | H | H | Me |
| H | CONHEt | H | H | H | H | H | H |
| H | CONHEt | H | H | H | Me | OMe | Me |
| H | CONHEt | H | H | H | H | H | Me |
| SO₂NMe₂ | H | H | H | H | H | H | H |
| SO₂NMe₂ | H | H | H | H | Me | OMe | Me |
| SO₂NMe₂ | H | H | H | H | H | H | Me |
| H | H | H | H | H | H | H | H |
| H | H | H | H | H | Me | H | H |
| H | H | H | H | H | H | Me | H |
| H | H | H | H | H | Me | H | Me |
| H | H | H | H | H | H | H | Me |
| H | H | H | H | H | H | OMe | H |
| H | H | H | H | H | Me | OMe | Me |
| Me | Me | H | H | H | H | H | Et |
| Me | Me | H | H | H | H | H | H |

TABLE 1-continued

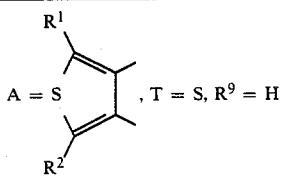

A = S, T = S, R⁹ = H

| R¹ | R² | R³ | R⁴ | R⁵ | R⁶ | R⁷ | R⁸ |
|---|---|---|---|---|---|---|---|
| Me | Me | H | H | H | Me | OMe | Me |
| Me | Me | H | H | H | H | H | Me |
| H | H | H | H | H | Cl |  | H |
| H | H | H | H | H | H | OCH₂CF₃ | H |
| H | COOEt | H | H | H | H | H | H |
| H | COOEt | H | H | H | Me | OMe | Me |
| H | COOEt | H | H | H | H | H | Me |
| COOMe | COOMe | H | H | H | H | H | H |
| COOMe | COOMe | H | H | H | Me | OMe | Me |
| COOMe | COOMe | H | H | H | H | H | Me |
| —(CH₂)₄— | | H | H | H | H | H | H |
| —(CH₂)₄— | | H | H | H | Me | OMe | Me |
| —(CH₂)₄— | | H | H | H | H | H | Me |
| —CH₂—O—CH₂— | | H | H | H | H | H | H |
| —CH₂—O—CH₂— | | H | H | H | Me | OMe | Me |
| —CH₂—O—CH₂— | | H | H | H | H | H | Me |
| —CH₂—S—CH₂— | | H | H | H | H | H | H |
| —CH₂—S—CH₂— | | H | H | H | Me | OMe | H |
| —CH₂—S—CH₂— | | H | H | H | H | H | Me |
| —CH₂—SO—CH₂— | | H | H | H | H | H | H |
| —CH₂—SO—CH₂— | | H | H | H | Me | OMe | Me |
| —CH₂—SO—CH₂— | | H | H | H | Me | H | H |
| —CH₂—SO—CH₂— | | H | H | H | H | H | Me |
| —CH=CH—CH=CH— | | H | H | H | H | H | H |
| —CH=CH—CH=CH— | | H | H | H | Me | OMe | Me |
| —CH=CH—CH=CH— | | H | H | H | H | H | Me |
| H | H | H | H | Me | H | H | H |
| H | H | H | H | Me | H | OMe | H |
| H | H | H | H | Me | H | OEt | H |
| H | H | H | H | Me | Me | H | H |
| H | H | H | H | Me | Me | OMe | H |
| H | H | H | H | Me | Me | OMe | Me |
| H | H | H | H | Me | H | H | Me |
| H | H | H | H | Me | H | Me | H |
| H | H | H | H | H | Me | Me | H |
| H | H | H | H | H | Et | H | H |
| H | H | H | H | H | H | Et | H |
| H | H | H | H | H | H | Pr | H |
| H | H | H | H | H | H | H | Pr |
| H | H | H | H | H | H | H | Bu |
| H | H | H | H | H | Me | OEt | H |
| H | H | H | H | H | H | OPr | H |
| H | H | H | H | H | H | OBu | H |
| H | H | H | H | H | H | OHex | H |
| H | H | H | H | H | H | H | Hex |
| H | H | H | H | H | Me | Me | Me |
| H | H | H | H | H | H | O—iPr | H |
| H | H | H | H | H | H | iPr | H |
| H | H | H | H | H | H | H | iPr |
| H | H | H | H | H | Cl | H | H |
| H | H | H | H | H | H | Cl | H |
| H | H | H | H | H | H | H | Cl |
| H | H | H | H | H | Cl | H | Me |
| H | H | H | H | H | Cl | Me | H |
| H | H | H | H | H | H | Me | Cl |
| H | H | H | H | H | Cl |  | H |

TABLE 1-continued

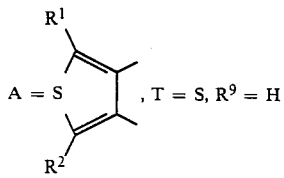

A = S, T = S, R⁹ = H

| R¹ | R² | R³ | R⁴ | R⁵ | R⁶ | R⁷ | R⁸ |
|---|---|---|---|---|---|---|---|
| H | H | H | H | H | Cl | 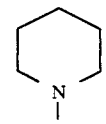 | H |
| H | H | H | H | H | Cl | OEt | H |
| H | H | H | H | H | Cl | OPr | H |
| H | H | H | H | H | Cl | OBu | H |
| H | H | H | H | H | Cl | 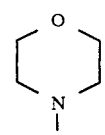 | H |
| H | H | H | H | H | Cl | O—(CH$_2$)$_2$—OMe | H |
| H | H | H | H | H | Me | O—(CH$_2$)$_2$OMe | H |
| H | H | H | H | H | H | O—(CH$_2$)$_2$—Ph | H |
| H | H | H | H | H | H | O—(CH$_2$)$_3$—Ph | H |
| H | H | H | H | H | H | OCH$_2$CF$_3$ | H |
| H | H | H | H | H | H | OCH$_2$(CF$_2$)$_2$CF$_3$ | H |
| H | H | H | H | H | H | OCH$_2$CF$_2$CF$_3$ | H |
| H | H | H | H | H | H | OCH$_2$—CF$_2$—CF$_2$H | H |
| H | H | H | H | H | Me | OCH$_2$—CF$_3$ | H |
| H | H | H | H | H | H | OCH$_2$CF$_3$ | Me |
| H | H | H | H | H | Cl | OCH$_2$CF$_3$ | H |
| H | H | H | H | H | Me | OCH$_2$CF$_2$CF$_3$ | H |
| Me | H | H | H | H | H | H | H |
| Me | H | H | H | H | H | OMe | H |
| Me | H | H | H | H | Me | OMe | H |
| Me | H | H | H | H | Me | OME | Me |
| Me | H | H | H | H | Me | H | H |
| Me | H | H | H | H | H | Me | H |
| Me | H | H | H | H | H | H | Me |
| Me | H | H | H | H | H | H | Et |
| Me | H | H | H | H | H | O—CH$_2$—Ph | H |
| Me | H | H | H | H | Cl | 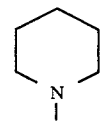 | H |
| Me | H | H | H | H | Cl | 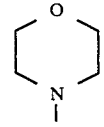 | H |
| Me | H | H | H | H | Cl | H | H |
| Me | H | H | H | H | H | Cl | H |
| Me | H | H | H | H | Cl | Me | H |
| Me | H | H | H | H | H | OCH$_2$CF$_3$ | H |
| Me | H | H | H | H | Me | H | Me |
| Et | H | H | H | H | H | H | H |
| Et | H | H | H | H | H | OMe | H |
| Et | H | H | H | H | Me | H | H |
| Et | H | H | H | H | H | H | Me |
| i-Pr | H | H | H | H | H | H | H |
| i-Pr | H | H | H | H | H | OMe | H |
| i-Pr | H | H | H | H | H | H | Me |

TABLE 1-continued $A = S$ [structure with R¹, R²], $T = S$, $R^9 = H$

| R¹ | R² | R³ | R⁴ | R⁵ | R⁶ | R⁷ | R⁸ |
|---|---|---|---|---|---|---|---|
| —CH(OH)—Me | H | H | H | H | H | H | H |
| —CH(OH)—Me | H | H | H | H | OMe | H |  |
| —CH(OH)—Me | H | H | H | H | Me | H | H |
| —CH(OH)—Me | H | H | H | H | H | H | Me |
| —CH(OH)—Me | H | H | H | H | Me | H | Me |
| OMe | Me | H | H | H | H | H | H |
| OMe | Me | H | H | H | Me | OMe | Me |
| OMe | Me | H | H | H | Me | H | H |
| OMe | Me | H | H | H | H | H | Me |
| OMe | Me | H | H | H | H | OMe | H |
| OMe | Me | H | H | H | H | Me | H |
| OMe | Me | H | H | H | Cl | N-methylmorpholino | H |
| OMe | Me | H | H | H | Cl | H | H |
| OMe | Me | H | H | H | H | H | Et |
| OMe | Me | H | H | H | Me | H | Me |
| Me | Ac | H | H | H | H | H | Me |
| Me | Ac | H | H | H | H | OMe | H |
| Me | Ac | H | H | H | Me | OMe | Me |
| OEt | Me | H | H | H | H | H | H |
| OEt | Me | H | H | H | Me | OMe | Me |
| OEt | Me | H | H | H | H | OMe | H |
| OEt | Me | H | H | H | H | H | Me |
| OEt | Me | H | H | H | Me | H | H |
| OBut | Me | H | H | H | H | H | Me |
| OBut | Me | H | H | H | Me | OMe | Me |
| OMe | OMe | H | H | H | H | H | H |
| OMe | OMe | H | H | H | H | OMe | H |
| OMe | OMe | H | H | H | Me | OMe | Me |
| OMe | OMe | H | H | H | Me | H | H |
| OMe | OMe | H | H | H | H | Me | H |
| OMe | OMe | H | H | H | H | H | Me |
| OMe | OMe | H | H | H | H | H | Et |
| OMe | OMe | H | H | H | Cl | N-methylmorpholino | H |
| OMe | OMe | H | H | H | Cl | OMe | H |
| OMe | Me | H | H | H | Cl | OMe | H |
| OMe | H | H | H | H | H | H | H |
| OMe | H | H | H | H | H | OMe | H |
| OMe | H | H | H | H | Me | OMe | Me |
| OMe | H | H | H | H | H | H | Me |
| OMe | H | H | H | H | H | Me | H |

TABLE 1-continued

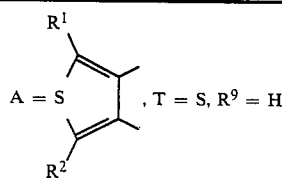

$A = S$, $T = S$, $R^9 = H$

| $R^1$ | $R^2$ | $R^3$ | $R^4$ | $R^5$ | $R^6$ | $R^7$ | $R^8$ |
|---|---|---|---|---|---|---|---|
| OMe | H | H | H | H | Me | H | H |
| OMe | Cl | H | H | H | H | H | H |
| OMe | Cl | H | H | H | Me | OMe | Me |
| OMe | Cl | H | H | H | H | H | Me |
| PhSO$_2$ | PhSO$_2$ | H | H | H | H | H | H |
| PhSO$_2$ | PhSO$_2$ | H | H | H | Me | OMe | Me |
| PhSO$_2$ | PhSO$_2$ | H | H | H | H | H | Me |
| NH—Ph | H | H | H | H | H | H | H |
| NH—Ph | H | H | H | H | Me | OMe | Me |
| NH—Ph | H | H | H | H | H | H | Me |
| NH—Ph | Cl | H |   |   | H | H | H |
| NH—Ph | Cl | H |   |   | Me | OMe | Me |
| NH—Ph | Cl | H |   |   | H | H | Me |
| O—Ph | H | H | H | H | H | H | H |
| O—Ph | H | H | H | H | Me | OMe | H |
| O—Ph | H | H | H | H | H | H | Me |
| O—Ph | H | H | H | H | H | H | H |
| Me | Me | H | H | H | H | H | Et |
| Me | Me | H | H | H | H | Et | H |
| Me | Me | H | H | H | Me | H | Me |
| Me | Me | H | H | H | Me | Me | Me |
| Me | Me | H | H | H | Cl | Me | H |
| Me | Me | H | H | H | Cl | OMe | H |
| Me | Me | H | H | H | Cl | H | H |
| Me | Me | H | H | H | Cl | Cl | H |
| Me | Me | H | H | H | Cl | N-piperidinyl | H |
| Me | Me | H | H | H | Cl | N-morpholinyl | H |
| Me | Me | H | H | H | H | O—CH$_2$Ph | H |
| Me | Me | H | H | H | H | —O—CH$_2$CF$_3$ | H |
| Me | Me | H | H | H | H | —O—CH$_2$—CF$_2$CF$_3$ | H |
| Me | Et | H | H | H | H | H | H |
| Me | Et | H | H | H | Me | OMe | Me |
| Me | Et | H | H | H | H | H | Me |
| Cl | COOMe | H | H | H | H | H | H |
| Cl | COOMe | H | H | H | Me | OMe | Me |
| Cl | COOMe | H | H | H | H | OMe | H |
| Cl | COOMe | H | H | H | H | H | Me |
| H | CONEt$_2$ | H | H | H | H | H | H |
| H | CONEt$_2$ | H | H | H | Me | OMe | Me |
| H | CONEt$_2$ | H | H | H | H | H | Me |
| H | CONH$_2$ | H | H | H | H | H | H |
| H | CONH$_2$ | H | H | H | Me | OMe | Me |
| H | CONH$_2$ | H | H | H | H | H | Me |
| H | CONHEt | H | H | H | H | H | H |
| H | CONHEt | H | H | H | Me | OMe | Me |
| Me | CONHEt | H | H | H | H | H | H |
| SO$_2$NMe$_2$ | H | H | H | H | H | H | H |
| SO$_2$NMe$_2$ | H | H | H | H | Me | OMe | Me |
| SO$_2$NMe$_2$ | H | H | H | H | H | H | Me |
| H | H | H | H | H | H | H | H |
| H | H | H | H | H | Me | H | H |
| H | H | H | H | H | H | Me | H |
| H | H | H | H | H | Me | H | Me |
| H | H | H | H | H | H | OMe | H |
| H | H | H | H | H | Me | OMe | Me |

TABLE 1-continued

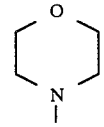

A = S, T = S, R⁹ = H

| R¹ | R² | R³ | R⁴ | R⁵ | R⁶ | R⁷ | R⁸ |
|---|---|---|---|---|---|---|---|
| H | H | H | H | H | H | H | Et |
| Me | Me | H | H | H | H | H | H |
| Me | Me | H | H | H | Me | OMe | Me |
| Me | Me | H | H | H | H | H | Me |
| H | H | H | H | H | Cl | morpholino | H |
| H | H | H | H | H | H | OCH$_2$CF$_3$ | H |
| H | COOEt | H | H | H | H | H | H |
| H | COOEt | H | H | H | Me | OMe | Me |
| H | COOEt | H | H | H | H | H | Me |
| COOMe | COOMe | H | H | H | H | H | H |
| COOMe | COOMe | H | H | H | Me | OMe | H |
| COOMe | COOMe | H | H | H | H | H | Me |
| —(CH$_2$)$_4$— | | H | H | H | H | H | H |
| —(CH$_2$)$_4$— | | H | H | H | Me | OMe | Me |
| —(CH$_2$)$_4$— | | H | H | H | H | H | Me |
| —CH$_2$—O—CH$_2$— | | H | H | H | H | H | H |
| —CH$_2$—O—CH$_2$— | | H | H | H | Me | OMe | Me |
| —CH$_2$—O—CH$_2$— | | H | H | H | H | H | Me |
| —CH$_2$—S—CH$_2$— | | H | H | H | H | H | H |
| —CH$_2$—S—CH$_2$— | | H | H | H | Me | OMe | H |
| —CH$_2$—S—CH$_2$— | | H | H | H | H | H | Me |
| —CH$_2$—SO—CH$_2$— | | H | H | H | H | H | H |
| —CH$_2$—SO—CH$_2$— | | H | H | H | Me | OMe | Me |
| —CH$_2$—SO—CH$_2$— | | H | H | H | Me | H | H |
| —CH$_2$—SO—CH$_2$— | | H | H | H | H | H | Me |
| —CH=CH—CH=CH— | | H | H | H | H | H | H |
| —CH=CH—CH=CH— | | H | H | H | Me | OMe Me | |
| —CH=CH—CH=CH— | | H | H | H | H | H | Me |
| H | H | H | H | H | Cl | OMe | Cl |
| H | H | H | H | H | Cl | OEt | Cl |
| H | H | H | H | H | Cl | OPr | Cl |
| H | H | H | H | H | Cl | OHex | Cl |
| H | H | H | H | H | Cl | OiPr | Cl |
| H | H | H | H | H | Cl | OCH$_2$Ph | Cl |
| H | H | H | H | H | Cl | O(CH$_2$)$_2$OMe | Cl |
| H | H | H | H | H | Cl | O(CH$_2$)$_2$Ph | Cl |
| H | H | H | H | H | Cl | OCH$_2$CF$_3$ | Cl |
| H | H | H | H | H | Cl | OCH$_2$(CF$_2$)$_2$CF$_3$ | Cl |
| H | H | H | H | H | Cl | OCH$_2$CF$_2$CF$_3$ | Cl |
| H | H | H | H | H | Cl | OCH$_2$CF$_2$CF$_2$H | Cl |
| Me | Me | H | H | H | Cl | OMe | Cl |
| Me | Me | H | H | H | Cl | OEt | Cl |
| Me | Me | H | H | H | Cl | OPr | Cl |
| Me | Me | H | H | H | Cl | OHex | Cl |
| Me | Me | H | H | H | Cl | OiPr | Cl |
| Me | Me | H | H | H | Cl | OCH$_2$Ph | Cl |
| Me | Me | H | H | H | Cl | O(CH$_{2w}$)$_2$OMe | Cl |
| Me | Me | H | H | H | Cl | O(CH$_2$)$_2$Ph | Cl |
| Me | Me | H | H | H | Cl | OCH$_2$CF$_3$ | Cl |
| Me | Me | H | H | H | Cl | OCH$_{2(CF2)}$$_2$CF$_3$ | Cl |
| Me | Me | H | H | H | Cl | OCH$_2$CF$_2$CF$_3$ | Cl |
| Me | Me | H | H | H | Cl | OCH$_2$CF$_2$CF$_2$H | Cl |
| Me | H | H | H | H | Cl | OMe | Cl |
| OMe | H | H | H | H | Cl | OEt | Cl |
| OMe | H | H | H | H | Cl | OPr | Cl |
| OMe | H | H | H | H | Cl | OHex | Cl |
| OMe | H | H | H | H | Cl | OiPr | Cl |
| OMe | H | H | H | H | Cl | OCH$_2$Ph | Cl |
| OMe | H | H | H | H | Cl | O(CH$_2$)$_2$OMe | Cl |
| OMe | H | H | H | H | Cl | O(CH$_2$)$_2$Ph | Cl |
| OMe | H | H | H | H | Cl | OCH$_2$CF$_3$ | Cl |

-continued

| | | |
|---|---|---|
| OMe | H | H |
| OMe | H | H |
| OMe | H | H |
| OM | OMe | H |
| Me | OMe | H |
| Me | OMe | H |
| Me | OMe | H |
| Me | OMe | H |
| Me | OMe | H |
| Me | OMe | H |
| Me | OMe | H |
| Me | OMe | H |
| Me | OMe | H |
| Me | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| H | H | H |
| H | H | H |
| H | H | H |
| H | H | H |
| H | H | H |
| H | H | H |
| H | H | H |
| H | H | H |
| H | H | H |
| H | H | H |
| Me | Me | H |
| Me | Me | H |
| Me | Me | H |
| Me | Me | H |
| Me | Me | H |
| Me | Me | H |
| Me | Me | H |
| Me | Me | H |
| Me | Me | H |
| Me | Me | H |
| H | OMe | H |
| H | OMe | H |
| H | OMe | H |
| H | OMe | H |
| H | OMe | H |
| H | OMe | H |
| H | OMe | H |
| H | OMe | H |
| H | OMe | H |
| H | OMe | H |
| OMe | Me | H |
| OMe | Me | H |
| OMe | Me | H |
| OMe | Me | H |
| OMe | Me | H |
| OMe | Me | H |
| OMe | Me | H |
| OMe | Me | H |
| OMe | Me | H |
| OMe | Me | H |
| OMe | OMe | H |
| OMe | OMe | H |
| OMe | OMe | H |
| OMe | OMe | H |
| OMe | OMe | H |
| OMe | OMe | H |

| | | | | |
|---|---|---|---|---|
| H | H | Cl | $OCH_2(CF_2)_2CF_3$ | Cl |
| H | H | Cl | $OCH_2CF_2CF_3$ | Cl |
| H | H | Cl | $OCH_2CF_2CF_2H$ | Cl |
| H | H | Cl | OMe | Cl |
| H | H | Cl | OEt | Cl |
| H | H | Cl | OPr | Cl |
| H | H | Cl | OHex | Cl |
| H | H | Cl | OiPr | Cl |
| H | H | Cl | $OCH_2Ph$ | Cl |
| H | H | Cl | $O(CH_2)_2OMe$ | Cl |
| H | H | Cl | $O(CH_2)_2Ph$ | Cl |
| H | H | Cl | $OCH_2CF_3$ | Cl |
| H | H | Cl | $OCH_2(CF_2)_2CF_3$ | Cl |
| H | H | Cl | $OCH_2CF_2CF_3$ | Cl |
| H | H | Cl | $OCH_2CF_2CF_2H$ | Cl |
| H | H | Cl | OMe | Cl |
| H | H | Cl | OEt | Cl |
| H | H | Cl | OPr | Cl |
| H | H | Cl | OHex | Cl |
| H | H | Cl | OiPr | Cl |
| H | H | Cl | $OCH_2Ph$ | Cl |
| H | H | Cl | $O(CH_2)_2OMe$ | Cl |
| H | H | Cl | $O(CH_2)_2Ph$ | Cl |
| H | H | Cl | $OCH_2CF_3$ | Cl |
| H | H | Cl | $OCH_2(CF_2)_2CF_3$ | Cl |
| H | H | Cl | $OCH_2CF_2CF_3$ | Cl |
| H | H | Cl | $OCH_2CF_2CF_2H$ | Cl |
| H | H | Cl | OMe | H |
| H | H | Cl | OEt | H |
| H | H | Cl | OPr | H |
| H | H | Cl | OHex | H |
| H | H | Cl | OiPr | H |
| H | H | Cl | $OCH_2Ph$ | H |
| H | H | Cl | $O(CH_2)_2OMe$ | H |
| H | H | Cl | $O(CH_2)_2Ph$ | H |
| H | H | Cl | $OCH_2CF_3$ | H |
| H | H | Cl | $OCH_2(CF_2)_2CF_3$ | H |
| H | H | Cl | $OCH_2CF_2CF_3$ | H |
| H | H | Cl | $OCH_2CF_2CF_2H$ | H |
| H | H | Cl | OMe | H |
| H | H | Cl | OEt | H |
| H | H | Cl | OPr | H |
| H | H | Cl | OHex | H |
| H | H | Cl | OiPr | H |
| H | H | Cl | $OCH_2Ph$ | H |
| H | H | Cl | $O(CH_2)_2OMe$ | H |
| H | H | Cl | $O(CH_2)_2Ph$ | H |
| H | H | Cl | $OCH_2CF_3$ | H |
| H | H | Cl | $OCH_2(CF_2)_2CF_3$ | H |
| H | H | Cl | $OCH_2CF_2CF_3$ | H |
| H | H | Cl | $OCH_2CF_2CF_2H$ | H |
| H | H | Cl | OMe | H |
| H | H | Cl | OEt | H |
| H | H | Cl | OPr | H |
| H | H | Cl | OHex | H |
| H | H | Cl | OiPr | H |
| H | H | Cl | $OCH_2Ph$ | H |
| H | H | Cl | $O(CH_2)_2OMe$ | H |
| H | H | Cl | $O(CH_2)_2Ph$ | H |
| H | H | Cl | $OCH_2CF_3$ | H |
| H | H | Cl | $OCH_2(CFC_2)_2CF_3$ | H |
| H | H | Cl | $OCH_2CF_2CF_3$ | H |
| H | H | Cl | $OCH_2CF_2CF_2H$ | H |
| H | H | Cl | OMe | H |
| H | H | Cl | OEt | H |
| H | H | Cl | OPr | H |
| H | H | Cl | OHex | H |
| H | H | Cl | OiPr | H |
| H | H | Cl | $OCH_2Ph$ | H |
| H | H | Cl | $O(CH_2)_2OMe$ | H |
| H | H | Cl | $O(CH_2)_2Ph$ | H |
| H | H | Cl | $OCH_2CF_3$ | H |
| H | H | Cl | $OCH_2(CF_2)_2CF_3$ | H |
| H | H | Cl | $OCH_2CF_2CFC_3$ | H |
| H | H | Cl | $OCH_2CF_2CF_2H$ | H |
| H | H | Cl | OMe | H |
| H | H | Cl | OEt | H |
| H | H | Cl | OPr | H |
| H | H | Cl | OHex | H |
| H | H | Cl | OiPr | H |
| H | H | Cl | $OCH_2Ph$ | H |
| H | H | Cl | $O(CH_2)_2OMe$ | H |
| H | H | Cl | $O(CH_2)_2Ph$ | H |

-continued

| | | | | |
|---|---|---|---|---|
| OMe | OMe | H | | |
| OMe | OMe | H | | |
| OMe | OMe | H | | |
| OMe | OMe | H | | |
| H | H | H | | |
| H | H | H | | |
| H | H | H | | |
| H | H | H | | |
| H | H | H | | |
| H | H | H | | |
| H | H | H | | |
| H | H | H | | |
| H | H | H | | |
| H | H | H | | |
| Me | Me | H | | |
| Me | Me | H | | |
| Me | Me | H | | |
| Me | Me | H | | |
| Me | Me | H | | |
| Me | Me | H | | |
| Me | Me | H | | |
| Me | Me | H | | |
| Me | Me | H | | |
| Me | Me | H | | |
| OMe | H | H | | |
| OMe | H | H | | |
| OMe | H | H | | |
| OMe | H | H | | |
| OMe | H | H | | |
| OMe | H | H | | |
| OMe | H | H | | |
| OMe | H | H | | |
| OMe | H | H | | |
| OMe | H | H | | |
| OMe | H | H | | |
| Me | OMe | H | | |
| Me | OMe | H | | |
| Me | OMe | H | | |
| Me | OMe | H | | |
| Me | OMe | H | | |
| Me | OMe | H | | |
| Me | OMe | H | | |
| Me | OMe | H | | |
| Me | OMe | H | | |
| Me | OMe | H | | |
| Me | OMe | H | | |
| OMe | OMe | H | | |
| OMe | OMe | H | | |
| OMe | OMe | H | | |
| OMe | OMe | H | | |
| OMe | OMe | H | | |
| OMe | OMe | H | | |
| OMe | OMe | H | | |
| OMe | OMe | H | | |
| OMe | OMe | H | | |
| OMe | OMe | H | | |
| OMe | OMe | H | | |
| H | H | H | | |
| H | H | H | | |
| H | H | H | | |
| H | H | H | | |
| H | H | H | | |
| H | H | H | | |
| H | H | H | | |
| H | H | H | | |
| H | H | H | | |
| H | H | H | | |
| H | H | H | | |
| Me | Me | H | | |
| Me | Me | H | | |
| Me | Me | H | | |
| Me | Me | H | | |
| Me | Me | H | | |
| Me | Me | H | | |
| Me | Me | H | | |

| | | | | |
|---|---|---|---|---|
| H | H | Cl | OCH$_2$CF$_3$ | H |
| H | H | Cl | OCH$_2$(CF$_2$)$_2$CF$_3$ | H |
| H | H | Cl | OCH$_2$CF$_2$CF$_3$ | H |
| H | H | Cl | OCH$_2$CF$_2$CF$_2$H | H |
| H | H | Me | OMe | Cl |
| H | H | Me | OEt | Cl |
| H | H | Me | OPr | Cl |
| H | H | Me | OHex | Cl |
| H | H | Me | OiPr | Cl |
| H | H | Me | OCH$_2$Ph | Cl |
| H | H | Me | O(CH$_2$)$_2$OMe | Cl |
| H | H | Me | O(CH$_2$)$_2$Ph | Cl |
| H | H | Me | OCH$_2$CF$_3$ | Cl |
| H | H | Me | OCH$_2$(CF$_2$)$_2$CF$_3$ | Cl |
| H | H | Me | OCH$_2$CF$_2$CF$_3$ | Cl |
| H | H | Me | OCH$_2$CF$_2$CF$_2$H | Cl |
| H | H | Me | OMe | Cl |
| H | H | Me | OEt | Cl |
| H | H | Me | OPr | Cl |
| H | H | Me | OHex | Cl |
| H | H | Me | OiPr | Cl |
| H | H | Me | OCH$_2$Ph | Cl |
| H | H | Me | O(CH$_2$)$_2$OMe | Cl |
| H | H | Me | O(CH$_2$)$_2$Ph | Cl |
| H | H | Me | OCH$_2$CF$_3$ | Cl |
| H | H | Me | OCH$_2$(CF$_2$)$_2$CF$_3$ | Cl |
| H | H | Me | OCH$_2$CF$_2$CF$_3$ | Cl |
| H | H | Me | OCH$_2$CF$_2$CF$_2$H | Cl |
| H | H | Me | OMe | Cl |
| H | H | Me | OEt | Cl |
| H | H | Me | OPr | Cl |
| H | H | Me | OHex | Cl |
| H | H | Me | OiPr | Cl |
| H | H | Me | OCH$_2$Ph | Cl |
| H | H | Me | O(CH$_2$)$_2$OMe | Cl |
| H | H | Me | O(CH$_2$)$_2$Ph | Cl |
| H | H | Me | OCH$_2$CF$_3$ | Cl |
| H | H | Me | OCH$_2$(CF$_2$)$_2$CF$_3$ | Cl |
| H | H | Me | OCH$_2$CF$_2$CF$_3$ | Cl |
| H | H | Me | OCH$_2$CF$_2$CF$_2$H | Cl |
| H | H | Me | OMe | Cl |
| H | H | Me | OEt | Cl |
| H | H | Me | OPr | Cl |
| H | H | Me | OHex | Cl |
| H | H | Me | OiPr | Cl |
| H | H | Me | OCH$_2$Ph | Cl |
| H | H | Me | O(CH$_2$)$_2$OMe | Cl |
| H | H | Me | O(CH$_2$)$_2$Ph | Cl |
| H | H | Me | OCH$_2$CF$_3$ | Cl |
| H | H | Me | OCH$_2$(CF$_2$)$_2$CF$_3$ | Cl |
| H | H | Me | OCH$_2$CF$_2$CF$_3$ | Cl |
| H | H | Me | OCH$_2$CF$_2$CF$_2$H | Cl |
| H | H | Cl | OMe | Me |
| H | H | Cl | OEt | Me |
| H | H | Cl | OPr | Me |
| H | H | Cl | OHex | Me |
| H | H | Cl | OiPr | Me |
| H | H | Cl | OCH$_2$Ph | Me |
| H | H | Cl | O(CH$_2$)$_2$OMe | Me |
| H | H | Cl | O(CH$_2$)$_2$Ph | Me |
| H | H | Cl | OCH$_2$CF$_3$ | Me |
| H | H | Cl | OCH$_2$(CF$_2$)$_2$CF$_3$ | Me |
| H | H | Cl | OCH$_2$CF$_2$CF$_3$ | Me |
| H | H | Cl | OCH$_2$CF$_2$CF$_2$H | Me |
| H | H | Cl | OMe | Me |
| H | H | Cl | OEt | Me |
| H | H | Cl | OPr | Me |
| H | H | Cl | OHex | Me |
| H | H | Cl | OiPr | Me |
| H | H | Cl | OCH$_2$Ph | Me |
| H | H | Cl | O(CH$_2$)$_2$OMe | Me |

-continued

| | | |
|---|---|---|
| Me | Me | H |
| Me | Me | H |
| Me | Me | H |
| Me | Me | H |
| Me | Me | H |
| H | OMe | H |
| H | OMe | H |
| H | OMe | H |
| H | OMe | H |
| H | OMe | H |
| H | OMe | H |
| H | OMe | H |
| H | OMe | H |
| H | OMe | H |
| H | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OMe | OMe | H |
| OEt | H | H |
| OEt | H | H |
| OEt | H | H |
| OEt | H | H |
| OEt | H | H |
| OEt | H | H |
| OEt | H | H |
| OEt | H | H |
| OEt | H | H |
| OEt | H | H |
| H | H | H |
| H | H | H |
| H | H | H |
| Me | H | H |
| Me | Me | H |
| Me | Me | H |
| H | OMe | H |
| H | OMe | H |
| H | OMe | H |
| H | OMe | H |
| H | OMe | H |
| Me | OMe | H |
| Me | OMe | H |
| OMe | OMe | H |
| OMe | OMe | H |
| OMe | OMe | H |
| H | H | H |
| H | H | H |
| H | H | H |
| Me | H | H |
| Me | Me | H |
| Me | Me | H |
| H | OMe | H |
| H | OMe | H |
| H | OMe | H |
| Me | OMe | H |
| OMe | OMe | H |
| OMe | OMe | H |
| H | H | H |
| H | H | H |
| H | H | H |
| Me | Me | H |
| Me | Me | H |
| OMe | H | H |
| OMe | H | H |
| OMe | H | H |
| OMe | H | H |

| | | | | |
|---|---|---|---|---|
| H | H | Cl | O(CH₂)₂Ph | Me |
| H | H | Cl | OCH₂CF₃ | Me |
| H | H | Cl | OCH₂(CF₂)₂CF₃ | Me |
| H | H | Cl | OCH₂CF₂CF₃ | Me |
| H | H | Cl | OCH₂CF₂CF₂H | Me |
| H | H | Cl | OMe | Me |
| H | H | Cl | OEt | Me |
| H | H | Cl | OPr | Me |
| H | H | Cl | OHex | Me |
| H | H | Cl | OiPr | Me |
| H | H | Cl | OCH₂Ph | Me |
| H | H | Cl | O(CH₂)₂OMe | Me |
| H | H | Cl | O(CH₂)₂Ph | Me |
| H | H | Cl | OCH₂CF₃ | Me |
| H | H | Cl | OCH₂(CF₂)₂CF₃ | Me |
| H | H | Cl | OCH₂CF₂CF₃ | Me |
| H | H | Cl | OCH₂CF₂CF₂H | Me |
| H | H | Cl | OMe | Me |
| H | H | Cl | OEt | Me |
| H | H | Cl | OPr | Me |
| H | H | Cl | OHex | Me |
| H | H | Cl | OiPr | Me |
| H | H | Cl | OCH₂Ph | Me |
| H | H | Cl | O(CH₂)₂OMe | Me |
| H | H | Cl | O(CH₂)₂Ph | Me |
| H | H | Cl | OCH₂CF₃ | Me |
| H | H | Cl | OCH₂(CF₂)₂CF₃ | Me |
| H | H | Cl | OCH₂CF₂CF₃ | Me |
| H | H | Cl | OCH₂CF₂CF₂H | Me |
| H | H | Cl | OMe | Me |
| H | H | Cl | OEt | Me |
| H | H | Cl | OPr | Me |
| H | H | Cl | OHex | Me |
| H | H | Cl | OiPr | Me |
| H | H | Cl | OCH₂Ph | Me |
| H | H | Cl | O(CH₂)₂OMe | Me |
| H | H | Cl | O(CH₂)₂Ph | Me |
| H | H | Cl | OCH₂CF₃ | Me |
| H | H | Cl | OCH₂(CF₂)₂CF₃ | Me |
| H | H | Cl | OCH₂CF₂CF₃ | Me |
| H | H | Cl | OCH₂CF₂CF₂H | Me |
| H | H | Me | OMe | Br |
| H | H | Me | OEt | Br |
| H | H | Me | OCH₂Ph | Br |
| H | H | Me | OCH₂CF₃ | Br |
| H | H | Me | OMe | Br |
| H | H | Me | OMe | Br |
| H | H | Me | OEt | Br |
| H | H | Me | OiPr | Br |
| H | H | Me | OMe | Br |
| H | H | Me | OEt | Br |
| H | H | Me | OiPr | Br |
| H | H | Me | OCH₂Ph | Br |
| H | H | Me | OCH₂CF₃ | Br |
| H | H | Me | OCH₂CH₂CF₃ | Br |
| H | H | Me | OMe | Br |
| H | H | Me | OPr | Br |
| H | H | Me | OCH₂Ph | Br |
| H | H | Me | OCH₂CF₃ | Br |
| H | H | Cl | OMe | Br |
| H | H | Cl | OPr | Br |
| H | H | Cl | OCH₂Ph | Br |
| H | H | Br | OEt | Br |
| H | H | Br | OMe | Br |
| H | H | Br | OCH₂Ph | Br |
| H | H | Br | OMe | Cl |
| H | H | Br | OPr | Cl |
| H | H | Br | OCH₂Ph | Cl |
| H | H | Br | OCH₂CF₃ | Cl |
| H | H | Br | OMe | Cl |
| H | H | Br | OMe | Cl |
| H | H | Br | OEt | Cl |
| H | H | Br | OCH₂Ph | H |
| H | H | Br | OCH₂CF₃ | H |
| H | H | Br | OCH₂CF₂CF₃ | H |
| H | H | Br | OMe | H |
| H | H | Br | OCH₂Ph | H |
| H | H | Br | OMe | H |
| H | H | Br | OCH₂Ph | H |
| H | H | Br | OCH₂CF₃ | H |
| H | H | Br | OCH₂CF₂CF₃ | H |

| | | |
|---|---|---|
| Me | OMe | H |
| Me | OMe | H |
| OMe | OMe | H |
| OMe | OMe | H |
| OMe | OMe | H |
| OMe | OMe | H |
| OMe | OMe | H |
| H | H | H |
| H | H | H |
| H | H | H |
| H | H | H |
| H | H | H |
| Me | Me | H |
| Me | Me | H |
| Me | Me | H |
| Me | Me | H |
| OMe | H | H |
| OMe | H | H |
| OMe | H | H |
| OMe | H | H |
| OMe | H | H |
| OMe | OMe | H |
| OMe | OMe | H |
| H | H | C₂OAc |
| H | H | CH₂OAc |
| H | H | CH₂OAc |
| H | H | CH₂OAc |
| Me | H | CH₂OAc |
| Me | Me | CH₂OAc |
| Me | Me | CH₂OAc |
| Me | Me | CH₂OAc |
| H | OMe | CH₂OAc |
| H | OMe | CH₂OAc |
| H | OMe | CH₂OAc |
| H | OMe | CH₂OAc |
| H | OMe | CH₂OAc |
| H | OMe | CH₂OAc |
| Me | OMe | CH₂OAc |
| OMe | OMe | CH₂OAc |
| OMe | OMe | CH₂OAc |
| OMe | OMe | CH₂OAc |
| OMe | OMe | CH₂OAc |
| H | H | CH₂OAc |
| H | H | CH₂OAc |
| H | H | CH₂OAc |
| Me | H | CH₂OAc |
| Me | Me | CH₂OAc |
| Me | Me | CH₂OAc |
| H | OMe | CH₂OAc |
| H | OMe | CH₂OAc |
| H | OMe | CH₂OAc |
| Me | OMe | CH₂OAc |
| OMe | OMe | CH₂OAc |
| OMe | OMe | CH₂OAc |
| H | H | CH₂OAc |
| H | H | CH₂OAc |
| H | H | CH₂OAc |
| Me | Me | CH₂OAc |
| Me | Me | CH₂OAc |
| OMe | H | CH₂OAc |
| OMe | H | CH₂OAc |
| OMe | H | CH₂OAc |
| Me | OMe | CH₂OAc |
| Me | OMe | CH₂OAc |
| OMe | OMe | CH₂OAc |
| OMe | OMe | CH₂OAc |
| OMe | OMe | CH₂OAc |
| OMe | OMe | CH₂OAc |
| H | H | CH₂OAc |
| H | H | CH₂OAc |
| H | H | CH₂OAc |
| H | H | CH₂OAc |
| Me | Me | CH₂OAc |
| Me | Me | CH₂OAc |
| Me | Me | CH₂OAc |
| Me | Me | CH₂OAc |
| OMe | H | CH₂OAc |
| OMe | H | CH₂OAc |
| OMe | H | CH₂OAc |
| OMe | H | CH₂OAc |

-continued

| | | | | |
|---|---|---|---|---|
| H | H | Br | OEt | H |
| H | H | Br | OCH₂CF₂CF₃ | H |
| H | H | Br | OMe | H |
| H | H | Br | OEt | H |
| H | H | Br | OiPr | H |
| H | H | Br | OCH₂Ph | H |
| H | H | Br | OC₂CF₃ | H |
| H | H | Br | OMe | Me |
| H | H | Br | OEt | Me |
| H | H | Br | OiPr | Me |
| H | H | Br | OCH₂Ph | Me |
| H | H | Br | OC₂CF₂CF₃ | Me |
| H | H | Br | OMe | Me |
| H | H | Br | OEt | Me |
| H | H | Br | OCH₂CF₃ | Me |
| H | H | Br | OCH₂CF₂CF₃ | Me |
| H | H | Br | OMe | Me |
| H | H | Br | OiPr | Me |
| H | H | Br | OCH₂Ph | Me |
| H | H | Br | OCH₂CF₃ | Me |
| H | H | Br | OMe | Me |
| H | H | Br | OMe | Me |
| H | H | Br | OCH₂Ph | Me |
| H | H | Me | OMe | Cl |
| H | H | Me | OEt | Cl |
| H | H | Me | OCH₂Ph | Cl |
| H | H | Me | OCH₂CF₃ | Cl |
| H | H | Me | OMe | Cl |
| H | H | Me | OMe | Cl |
| H | H | Me | OEt | Cl |
| H | H | Me | OiPr | Cl |
| H | H | Me | OMe | Cl |
| H | H | Me | OEt | Cl |
| H | H | Me | OiPr | Cl |
| H | H | Me | OCH₂Ph | Cl |
| H | H | Me | OC₂CF₃ | Cl |
| H | H | Me | OCH₂CH₂CF₃ | Cl |
| H | H | Me | OMe | Cl |
| H | H | Me | OMe | Cl |
| H | H | Me | Opr | Cl |
| H | H | Me | OCH₂Ph | Cl |
| H | H | Me | OCH₂CF₃ | Cl |
| H | H | Cl | OMe | Cl |
| H | H | Cl | OPr | Cl |
| H | H | Cl | OCH₂Ph | Cl |
| H | H | Cl | OEt | Cl |
| H | H | Cl | OMe | Cl |
| H | H | Cl | OCH₂Ph | Cl |
| H | H | Cl | OMe | Cl |
| H | H | Cl | OPr | Cl |
| H | H | Cl | OCH₂Ph | Cl |
| H | H | Cl | OCH₂CF₃ | Cl |
| H | H | Cl | OMe | Cl |
| H | H | Cl | OMe | Cl |
| H | H | Cl | OEt | Cl |
| H | H | Cl | OCH₂Ph | H |
| H | H | Cl | OCH₂CF₃ | H |
| H | H | Cl | OCH₂CF₂CF₃ | H |
| H | H | Cl | OMe | H |
| H | H | Cl | OCH₂Ph | H |
| H | H | Cl | OMe | H |
| H | H | Cl | OCH₂Ph | H |
| H | H | Cl | OCH₂CF₂CF₃ | H |
| H | H | Cl | OEt | H |
| H | H | Cl | OCH₂CF₂CF₃ | H |
| H | H | Cl | OMe | H |
| H | H | Cl | OEt | H |
| H | H | Cl | OiPr | H |
| H | H | Cl | OCH₂Ph | H |
| H | H | Cl | OCH₂CF₃ | H |
| H | H | Cl | OMe | Me |
| H | H | Cl | OEt | Me |
| H | H | Cl | OiPr | Me |
| H | H | Cl | OCH₂Ph | Me |
| H | H | Cl | OCH₂CF₂CF₃ | Me |
| H | H | Cl | OMe | Me |
| H | H | Cl | OEt | Me |
| H | H | Cl | OCH₂CF₃ | Me |
| H | H | Cl | OCH₂CF₂CF₃ | Me |
| H | H | Cl | OMe | Me |
| H | H | Cl | OiPr | Me |
| H | H | Cl | OC₂Ph | Me |
| H | H | Cl | OCH₂CF₃ | Me |

-continued

| | | | | | | | |
|---|---|---|---|---|---|---|---|
| OMe | Me | CH₂OAc | H | H | Cl | OMe | Me |
| OMe | OMe | CH₂OAc | H | H | Cl | OMe | Me |
| OMe | OMe | CH₂OAc | H | H | Cl | OCH₂Ph | Me |
| OMe | OMe | CH₂OAc | H | H | Cl | OiPr | Cl |
| OMe | OMe | CH₂OAc | H | H | Cl | OCH₂Ph | Cl |
| OMe | OMe | CH₂OAc | H | H | Cl | OC₂CF₃ | Cl |
| H | H | CH₂OAc | H | H | Me | OMe | Me |
| H | H | CH₂OAc | H | H | Me | OCH₂Ph | Me |
| Me | Me | CH₂OAc | H | H | Me | OMe | Me |
| Me | Me | CH₂OAc | H | H | Me | OCH₂CF₃ | Me |
| OMe | H | CH₂OAc | H | H | Me | OMe | Me |
| OMe | H | CH₂OAc | H | H | Me | Opr | Me |
| OMe | Me | CH₂OAc | H | H | Me | OMe | Me |
| OMe | Me | CH₂OAc | H | H | Me | O(CH₂)₂OMe | Me |
| OMe | OMe | CH₂OAc | H | H | Me | OMe | Me |
| OMe | OMe | CH₂OAc | H | H | Me | OCH₂CF₃ | Me |
| H | H | CH₂OAc | H | H | Cl | OMe | H |
| H | H | CH₂OAc | H | H | Cl | OEt | H |
| H | H | CH₂OAc | H | H | Cl | OiPr | H |
| OMe | OMe | CH₂OAc | H | H | Cl | OCH₂CF₃ | Me |
| H | H | CH₂OAc | H | H | H | Me | H |
| Me | H | CH₂OAc | H | H | H | iPr | H |
| Me | Me | CH₂OAc | H | H | Me | iPr | H |
| OMe | H | CH₂OAc | H | H | H | Me | H |
| OMe | H | CH₂OAc | H | H | Me | Me | H |
| OMe | H | CH₂OAc | H | H | Me | iPr | H |
| OMe | Me | CH₂OAc | H | H | Me | Me | H |
| OMe | OMe | CH₂OAc | H | H | H | Me | H |
| OMe | OMe | CH₂OAc | H | H | Me | Me | H |
| OMe | OMe | CH₂OAc | H | H | H | Me | Me |
| H | H | CH₂OAc | H | H | Me | Me | Me |
| H | H | CH₂OAc | H | H | Cl | Me | H |
| Me | Me | CH₂OAc | H | H | Me | Me | Me |
| Me | Me | CH₂OAc | H | H | Cl | Me | H |
| Me | Me | CH₂OAc | H | H | H | Me | Cl |
| OMe | H | CH₂OAc | H | H | Me | Me | Me |
| OMe | H | CH₂OAc | H | H | Cl | Me | H |
| OMe | OMe | CH₂OAc | H | H | Me | Me | Me |
| OMe | OMe | CH₂OAc | H | H | Cl | Me | H |
| OMe | OMe | CH₂OAc | H | H | Me | Et | Me |
| H | H | CH₂OAc | H | H | Cl | Me | Cl |
| H | H | CH₂OAc | H | H | Cl | Me | Me |
| H | H | CH₂OAc | H | H | Cl | Et | Me |
| Me | Me | CH₂OAc | H | H | Cl | Me | Me |
| Et | Et | CH₂OAc | H | H | Me | Me | Cl |
| OMe | H | CH₂OAc | H | H | Cl | Me | Cl |
| OMe | H | CH₂OAc | H | H | Cl | Me | Me |
| OMe | Me | CH₂OAc | H | H | Me | Me | Cl |
| OMe | OMe | CH₂OAc | H | H | Cl | Me | Me |
| OMe | OMe | CH₂OAc | H | H | Me | Me | Cl |
| OEt | OEt | CH₂OAc | H | H | Me | Me | Cl |
| H | H | CH₂OAc | H | H | Me | 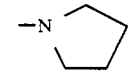 | H |
| Me | Me | CH₂OAc | H | H | Me | 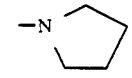 | H |
| OMe | H | CH₂OAc | H | H | Me | 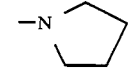 | H |
| OEt | H | CH₂OAc | H | H | H | —NMe₂ | Me |
| OMe | OMe | CH₂OAc | H | H | CH₃ | —NMe₂ | H |
| OEt | OEt | CH₂OAc | H | H | H | —NMe₂ | Me |
| Me | H | CH₂OAc | H | H | Cl | 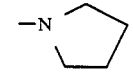 | H |
| Me | Me | CH₂OAc | H | H | Cl | —NMe₂ | H |
| OMe | H | CH₂OAc | H | H | Cl | —NMe₂ | H |
| OMe | OMe | CH₂OAc | H | H | Cl | —NMe₂ | H |

-continued

| | | | | | | | |
|---|---|---|---|---|---|---|---|
| OMe | OMe | CH₂OAc | H | H | Cl | —N(pyrrolidine) | H |
| H | H | CH₂OAc | H | H | Cl | —NMe₂ | Cl |
| Me | H | CH₂OAc | H | H | Cl | —N(piperidine) | Cl |
| Et | H | CH₂OAc | H | H | Cl | —NMe₂ | CH₃ |
| Me | Me | CH₂OAc | H | H | Cl | —N(pyrrolidine) | Cl |
| OMe | H | CH₂OAc | H | H | Cl | —NMe₂ | Cl |
| OCH₂Ph | H | CH₂OAc | H | H | Cl | —N(pyrrolidine) | Cl |
| OEt | H | CH₂OAc | H | H | Cl | —N(piperidine) | Cl |
| OMe | H | CH₂OAc | H | H | Cl | —NMe₂ | Me |
| OMe | H | CH₂OAc | H | H | Cl | NMe₂ | Cl |
| OMe | OMe | CH₂OAc | H | H | Cl | —N(piperidine) | Cl |
| OMe | OMe | CH₂OAc | H | H | Cl | —N(pyrrolidine) | Me |
| OEt | OEt | CH₂OAc | H | H | Me | —N(piperidine) | Cl |
| H | H | CH(CH₃)OAc | H | H | Me | OMe | Cl |
| H | H | CH(CH₃)OAc | H | H | Me | OEt | Cl |
| H | H | CH(CH₃)OAc | H | H | Me | OCH₂Ph | Cl |
| H | H | CH(CH₃)OAc | H | H | Me | OCH₂CF₃ | Cl |
| Me | H | CH(CH₃)OAc | H | H | Me | OMe | Cl |
| Me | Me | CH(CH₃)OAc | H | H | Me | OMe | Cl |
| Me | Me | CH(CH₃)OAc | H | H | Me | OEt | Cl |
| Me | Me | CH(CH₃)OAc | H | H | Me | OiPr | Cl |
| H | OMe | CH(CH₃)OAc | H | H | Me | OMe | Cl |
| H | OMe | CH(CH₃)OAc | H | H | Me | OEt | Cl |
| H | OMe | CH(CH₃)OAc | H | H | Me | OiPr | Cl |
| H | OMe | CH(CH₃)OAc | H | H | Me | OCH₂Ph | Cl |
| H | OMe | CH(CH₃)OAc | H | H | Me | OCH₂CF₃ | Cl |
| H | OMe | CH(CH₃)OAc | H | H | Me | OCH₂CH₂CF₃ | Cl |
| Me | OMe | CH(CH₃)OAc | H | H | Me | OMe | Cl |
| OMe | OMe | CH(CH₃)OAc | H | H | Me | OMe | Cl |
| OMe | OMe | CH(CH₃)OAc | H | H | Me | Opr | Cl |
| OMe | OMe | CH(CH₃)OAc | H | H | Me | OCH₂Ph | Cl |
| OMe | OMe | CH(CH₃)OAc | H | H | Me | OCH₂CF₃ | Cl |
| H | H | CH(CH₃)OAc | H | H | Cl | OMe | Cl |
| H | H | CH(CH₃)OAc | H | H | Cl | Opr | Cl |
| H | H | CH(CH₃)OAc | H | H | Cl | OCH₂Ph | Cl |
| Me | H | CH(CH₃)OAc | H | H | Cl | OEt | Cl |
| Me | Me | CH(CH₃)OAc | H | H | Cl | OMe | Cl |

-continued

| | | | | | | | |
|---|---|---|---|---|---|---|---|
| Me | Me | CH(CH₃)OAc | H | H | Cl | OCH₂Ph | Cl |
| H | OMe | CH(CH₃)OAc | H | H | Cl | OMe | Cl |
| H | OMe | CH(CH₃)OAc | H | H | Cl | OPr | Cl |
| H | OMe | CH(CH₃)OAc | H | H | Cl | OCH₂Ph | Cl |
| H | OMe | CH(CH₃)OAc | H | H | Cl | OCH₂CF₃ | Cl |
| Me | OMe | CH(CH₃)OAc | H | H | Cl | OMe | Cl |
| OMe | OMe | CH(CH₃)OAc | H | H | Cl | OMe | Cl |
| OMe | OMe | CH(CH₃)OAc | H | H | Cl | OEt | Cl |
| H | H | CH(CH₃)OAc | H | H | Cl | OCH₂Ph | H |
| H | H | CH(CH₃)OAc | H | H | Cl | OCH₂CF₃ | H |
| H | H | CH(CH₃)OAc | H | H | Cl | OCH₂CF₂CF₃ | H |
| Me | Me | CH(CH₃)OAc | H | H | Cl | OMe | H |
| Me | Me | CH(CH₃)OAc | H | H | Cl | OCH₂Ph | H |
| OMe | H | CH(CH₃)OAc | H | H | Cl | OMe | H |
| OMe | H | CH(CH₃)OAc | H | H | Cl | OCH₂Ph | H |
| OMe | H | CH(CH₃)OAC | H | H | Cl | OCH₂CF₃ | H |
| OMe | H | CH(CH₃)OAc | H | H | Cl | OCH₂CF₂CF₃ | H |
| Me | OMe | CH(CH₃)OAc | H | H | Cl | OEt | H |
| Me | OMe | CH(CH₃)OAc | H | H | Cl | OCH₂CF₂CF₃ | H |
| OMe | OMe | CH(CH₃)OAc | H | H | Cl | OMe | H |
| OMe | OMe | CH(CH₃)OAc | H | H | Cl | OEt | H |
| OMe | OMe | CH(CH₃)OAc | H | H | Cl | OiPr | H |
| OMe | OMe | CH(CH₃)OAc | H | H | Cl | OCH₂Ph | H |
| OMe | OMe | CH(CH₃)OAc | H | H | Cl | OCH₂CF₃ | H |
| H | H | CH(CH₃)OAc | H | H | Cl | OMe | Me |
| H | H | CH(CH₃)OAc | H | H | Cl | OEt | Me |
| H | H | CH(CH₃)OAc | H | H | Cl | OiPr | Me |
| H | H | CH(CH₃)OAc | H | H | Cl | OCH₂Ph | Me |
| H | H | CH(CH₃)OAc | H | H | Cl | OCH[₂CF₂CF₃ | Me |
| Me | Me | CH(CH₃)OAc | H | H | Cl | OMe | Me |
| Me | Me | CH(CH₃)OAc | H | H | Cl | OEt | Me |
| Me | Me | CH(CH₃)OAc | H | H | Cl | OCH₂CF₃ | Me |
| Me | Me | CH(CH₃)OAc | H | H | Cl | OCH₂CF₂CF₃ | Me |
| OMe | H | CH(CH₃)OAc | H | H | Cl | OMe | Me |
| OMe | H | CH(CH₃)OAc | H | H | Cl | OiPr | Me |
| OMe | H | CH(CH₃)OAc | H | H | Cl | OCH₂Ph | Me |
| OMe | H | CH(CH₃)OAc | H | H | Cl | OCH₂CF₃ | Me |
| OMe | Me | CH(CH₃)OAc | H | H | Cl | OMe | Me |
| OMe | OMe | CH(CH₃)OAc | H | H | Cl | OMe | Me |
| OMe | OMe | CH(CH₃)OAc | H | H | Cl | OCH₂Ph | Me |
| OMe | OMe | CH(CH₃)OAc | H | H | Cl | OiPr | Cl |
| OMe | OMe | CH(CH₃)OAc | H | H | Cl | OCH₂Ph | Cl |
| OMe | OMe | CH(CH₃)OAc | H | H | Cl | OCH₂CF₃ | Cl |
| H | H | CH(CH₃)OAc | H | H | Me | OMe | Me |
| H | H | CH(CH₃)OAc | H | H | Me | OCH₂Ph | Me |
| Me | Me | CH(CH₃)OAc | H | H | Me | OMe | Me |
| Me | Me | CH(CH₃)OAc | H | H | Me | OCH₂CF₃ | Me |
| OMe | H | CH(CH₃)OAc | H | H | Me | OMe | Me |
| OMe | H | CH(CH₃)OAc | H | H | Me | OPr | Me |
| OMe | Me | CH(CH₃)OAc | H | H | Me | OMe | Me |
| OMe | Me | CH(CH₃)OAc | H | H | Me | O(CH₂)₂OMe | Me |
| OMe | OMe | CH(CH₃)OAc | H | H | Me | OMe | Me |
| OMe | OMe | CH(CH₃)OAc | H | H | Me | OCH₂CF₃ | Me |
| H | H | CH(CH₃)OAc | H | H | Cl | OMe | H |
| H | H | CH(C₃)OAc | H | H | Cl | OEt | H |
| H | H | CH(CH₃)OAc | H | H | Cl | OiPr | H |
| OMe | OMe | CH(CH₃)OAc | H | H | Cl | OCH₂CF₃ | Me |
| H | H | CH(CH₃)OAc | H | H | H | Me | H |
| Me | H | CH(CH₃)OAc | H | H | H | iPr | H |
| Me | Me | CH(CH₃)OAc | H | H | Me | Me | H |
| Me | Me | CH(CH₃)OAc | H | H | Me | iPr | H |
| OMe | H | CH(CH₃)OAc | H | H | H | Me | H |
| OMe | H | CH(CH₃)OAc | H | H | Me | Me | H |
| OMe | H | CH(CH₃)OAc | H | H | Me | iPr | H |
| OMe | Me | CH(CH₃)OAc | H | H | Me | Me | H |
| OMe | OMe | CH(CH₃)OAc | H | H | H | Me | H |
| OMe | OMe | CH(CH₃)OAc | H | H | Me | Me | H |
| OMe | OMe | CH(C₃)OAc | H | H | H | Me | Me |
| H | H | CH(CH₃)OAc | H | H | Me | Me | Me |
| H | H | CH(CH₃)OAc | H | H | Cl | Me | H |
| Me | Me | CH(C₃)OAc | H | H | Me | Me | Me |
| Me | Me | CH(CH₃)OAc | H | H | Cl | Me | H |
| Me | Me | CH(CH₃)OAc | H | H | H | Me | Cl |
| OMe | H | CH(CH₃)OAc | H | H | Me | Me | Me |
| OMe | H | CH(CH₃)OAc | H | H | Cl | Me | H |
| OMe | OMe | CH(CH₃)OAc | H | H | Me | Me | Me |
| OMe | OMe | CH(CH₃)OAc | H | H | Cl | Me | H |
| H | H | CH(CH₃)OAc | H | H | Me | Et | Me |
| H | H | CH(CH₃)OAc | H | H | Cl | Me | Cl |
| H | H | CH(CH₃)OAc | H | H | Cl | Me | Me |
| Me | Me | CH(CH₃)OAc | H | H | Cl | Et | Me |
| Et | Et | CH(CH₃)OAc | H | H | Me | Me | Cl |

-continued

| | | | | | | | |
|---|---|---|---|---|---|---|---|
| OMe | H | CH(CH₃)OAc | H | H | Cl | Me | Cl |
| OMe | H | CH(CH₃)OAc | H | H | Cl | Me | Me |
| OMe | OMe | CH(CH₃)OAc | H | H | Me | Me | Cl |
| OMe | OMe | CH(CH₃)OAc | H | H | Cl | Me | Me |
| OMe | OMe | CH(CH₃)OAc | H | H | Me | Me | Cl |
| OEt | OEt | CH(CH₃)OAc | H | H | Me | Me | Cl |
| H | H | CH(CH₃)OAc | H | H | Me | 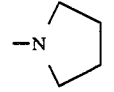 | H |
| Me | Me | CH(CH₃)OAc | H | H | Me | 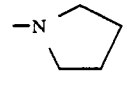 | H |
| OMe | H | CH(CH₃)OAc | H | H | Me | 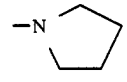 | H |
| OEt | H | CH(CH₃)OAc | H | H | H | —NMe₂ | Me |
| OMe | OMe | CH(CH₃)OAc | H | H | CH₃ | —NMe₂ | H |
| OEt | OEt | CH(CH₃)OAc | H | H | H | —NMe₂ | Me |
| Me | H | CH(CH₃)OAc | H | H | Cl | 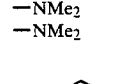 | H |
| Me | Me | CH(CH₃)OAc | H | H | Cl | —NMe₂ | H |
| OMe | H | CH(CH₃)OAc | H | H | Cl | —NMe₂ | H |
| OMe | OMe | CH(CH₃)OAc | H | H | Cl | —NMe₂ | H |
| OMe | OMe | CH(CH₃)OAc | H | H | Cl |  | H |
| H | H | CH(CH₃)OAc | H | H | Cl | —NMe₂ | Cl |
| Me | H | CH(CH₃)OAc | H | H | Cl | 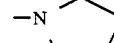 | Cl |
| Et | H | CH(CH₃)OAc | H | H | Cl | —NMe₂ | CH₃ |
| Me | Me | CH(CH₃)OAc | H | H | Cl | 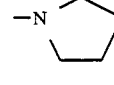 | Cl |
| OMe | H | CH(CH₃)OAc | H | H | Cl | —NMe₂ | Cl |
| OCH₂Ph | H | CH(CH₃)OAc | H | H | Cl | 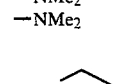 | Cl |
| OEt | H | CH(CH₃)OAc | H | H | Cl | 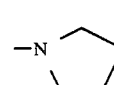 | Cl |
| OMe | H | CH(CH₃)OAc | H | H | Cl | —NMe₂ | Me |
| OMe | H | CH(CH₃)OAc | H | H | Cl | NMe₂ | Cl |
| OMe | OMe | CH(CH₃)OAc | H | H | Cl | 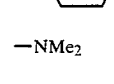 | Cl |

-continued

| | | | | | | | |
|---|---|---|---|---|---|---|---|
| OMe | OMe | CH(CH₃)OAc | H | H | Cl | 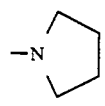 | Me |
| OEt | OEt | CH(CH₃)OAc | H | H | Me | 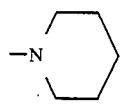 | Cl |
| H | H | CH(CH₃)—O—CO—[CH₂]₄CH₃ | H | H | Me | OMe | Cl |
| H | H | CH(CH₃)—O—CO—[CH₂]₄CH₃ | H | H | Me | OEt | Cl |
| H | H | CH(CH₃)—O—CO—[CH₂]₄CH₃ | H | H | Me | OCH₂Ph | Cl |
| H | H | CH(CH₃)—O—CO—[CH₂]₄CH₃ | H | H | Me | OCH₂CF₃ | Cl |
| Me | H | CH(CH₃)—O—CO—[CH₂]₄CH₃ | H | H | Me | OMe | Cl |
| Me | Me | CH(CH₃)—O—CO—[CH₂]₄CH₃ | H | H | Me | OMe | Cl |
| Me | Me | CH(CH₃)—O—CO—[CH₂]₄CH₃ | H | H | Me | OEt | Cl |
| Me | Me | CH(CH₃)—O—CO—[CH₂]₄CH₃ | H | H | Me | OiPr | Cl |
| H | OMe | CH(CH₃)—O—CO—[CH₂]₄CH₃ | H | H | Me | OMe | Cl |
| H | OMe | CH(CH₃)—O—CO—[CH₂]₄CH₃ | H | H | Me | OEt | Cl |
| H | OMe | CH(CH₃)—O—CO—[CH₂]₄CH₃ | H | H | Me | OiPr | Cl |
| H | OMe | CH(CH₃)—O—CO—[CH₂]₄CH₃ | H | H | Me | OCH₂Ph | Cl |
| H | OMe | CH(CH₃)—O—CO—[CH₂]₄CH₃ | H | H | Me | OCH₂CF₃ | Cl |
| H | OMe | CH(CH₃)—O—CO—[CH₂]₄CH₃ | H | H | Me | OCH₂CH₂CF₃ | Cl |
| Me | OMe | CH(CH₃)—O—CO—[CH₂]₄CH₃ | H | H | Me | OMe | Cl |
| OMe | OMe | CH(CH₃)—O—CO—[CH₂]₄CH₃ | H | H | Me | OMe | Cl |
| OMe | OMe | CH(CH₃)—O—CO—[CH₂]₄CH₃ | H | H | Me | OPr | Cl |
| OMe | OMe | CH(CH₃)—O—CO—[CH₂]₄CH₃ | H | H | Me | OCH₂Ph | Cl |
| OMe | OMe | CH(CH₃)—O—CO—[CH₂]₄CH₃ | H | H | Me | OC₂CF₃ | Cl |
| H | H | CH(CH₃)—O—CO—[CH₂]₄CH₃ | H | H | Cl | OMe | Cl |
| H | H | CH(CH₃)—O—CO—[CH₂]₄CH₃ | H | H | Cl | OPr | Cl |
| H | H | CH(CH₃)—O—CO—[CH₂]₄CH₃ | H | H | Cl | OCH₂Ph | Cl |
| Me | H | CH(CH₃)—O—CO—[CH₂]₄CH₃ | H | H | Cl | OEt | Cl |
| Me | Me | CH(CH₃)—O—CO—[CH₂]₄CH₃ | H | H | Cl | OMe | Cl |
| Me | Me | CH(CH₃)—O—CO—[CH₂]₄CH₃ | H | H | Cl | OCH₂Ph | Cl |
| H | OMe | CH(CH₃)—O—CO—[CH₂]₄CH₃ | H | H | Cl | OMe | Cl |
| H | OMe | CH(CH₃)—O—CO—[CH₂]₄CH₃ | H | H | Cl | OPr | Cl |
| H | OMe | CH(CH₃)—O—CO—[CH₂]₄CH₃ | H | H | Cl | OCH₂Ph | Cl |
| H | OMe | CH(CH₃)—O—CO—[CH₂]₄CH₃ | H | H | Cl | OCH₂CF₃ | Cl |
| Me | OMe | CH(CH₃)—O—CO—[CH₂]₄CH₃ | H | H | Cl | OMe | Cl |
| OMe | OMe | CH(CH₃)—O—CO—[CH₂]₄CH₃ | H | H | Cl | OMe | Cl |
| OMe | OMe | CH(CH₃)—O—CO—[CH₂]₄CH₃ | H | H | Cl | OEt | Cl |
| H | H | CH(CH₃)—O—CO—[CH₂]₄CH₃ | H | H | Cl | OCH₂Ph | H |
| H | H | CH(CH₃)—O—CO—[CH₂]₄CH₃ | H | H | Cl | OCH₂CF₃ | H |
| H | H | CH(CH₃)—O—CO—[CH₂]₄CH₃ | H | H | Cl | OCH₂CF₂CF₂CF₃ | H |
| Me | Me | " | H | H | Cl | OMe | H |
| Me | Me | " | H | H | Cl | OCH₂Ph | H |
| OMe | H | " | H | H | Cl | OMe | H |
| OMe | H | " | H | H | Cl | OCH₂Ph | H |
| OMe | H | " | H | H | Cl | OCH₂CF₃ | H |
| OMe | H | " | H | H | Cl | OCH₂CF₂CF₃ | H |
| Me | OMe | " | H | H | Cl | OEt | H |
| Me | OMe | " | H | H | Cl | OCH₂CF₂CF₃ | H |
| OMe | OMe | " | H | H | Cl | OMe | H |
| OMe | OME | " | H | H | Cl | OEt | H |
| OMe | OMe | " | H | H | Cl | OiPr | H |
| OMe | OMe | " | H | H | Cl | OCH₂Ph | H |
| OMe | OMe | " | H | H | Cl | OCH₂CF₃ | H |
| H | H | " | H | H | Cl | OMe | Me |
| H | H | " | H | H | Cl | OEt | Me |
| H | H | " | H | H | Cl | OiPr | Me |
| H | H | " | H | H | Cl | OCH₂Ph | Me |
| H | H | " | H | H | Cl | OCH₂CF₂CF₃ | Me |
| Me | Me | " | H | H | Cl | OMe | Me |
| Me | Me | " | H | H | Cl | OEt | Me |
| Me | Me | " | H | H | Cl | OCH₂CF₃ | Me |
| Me | Me | CH(CH₃)—O—CO—(CH₂)₄CH₃ | H | H | Cl | OCH₂CF₂CF₃ | Me |
| OMe | H | " | H | H | Cl | OMe | Me |
| OMe | H | " | H | H | Cl | OiPr | Me |
| OMe | H | " | H | H | Cl | OCH₂Ph | Me |
| OMe | Me | " | H | H | Cl | OCH₂CF₃ | Me |
| OMe | OMe | " | H | H | Cl | OMe | Me |
| OMe | OMe | " | H | H | Cl | OCH₂Ph | Me |
| OMe | OMe | " | H | H | Cl | OiPr | Cl |
| OMe | OMe | " | H | H | Cl | OCH₂Ph | Cl |
| OMe | OMe | " | H | H | Cl | OCH₂CF₃ | Cl |
| H | H | " | H | H | Me | OMe | Me |
| H | H | " | H | H | Me | OCH₂Ph | Me |
| Me | Me | " | H | H | Me | OMe | Me |
| Me | Me | " | H | H | Me | OCH₂CF₃ | Me |

-continued

| | | | | | | | |
|---|---|---|---|---|---|---|---|
| OMe | H | " | H | H | Me | OMe | Me |
| OMe | H | " | H | H | Me | Opr | Me |
| Ome | Me | " | H | H | Me | OMe | Me |
| OMe | Me | " | H | H | Me | O(CH$_2$)$_2$OMe | Me |
| OMe | OMe | " | H | H | Me | OMe | Me |
| OMe | OMe | " | H | H | Me | OCH$_2$CF$_3$ | Me |
| H | H | " | H | H | Cl | OMe | H |
| H | H | CH(CH$_3$)—O—CO—(CH$_2$)$_4$CH$_3$ | H | H | Cl | OEt | H |
| H | H | " | H | H | Cl | OiPr | H |
| OMe | OMe | " | H | H | Cl | OCH$_2$CF$_3$ | H |
| H | H | " | H | H | H | Me | H |
| Me | H | " | H | H | H | iPr | H |
| Me | Me | " | H | H | H | Me | H |
| Me | Me | " | H | H | Me | iPr | H |
| OMe | H | " | H | H | H | Me | H |
| OMe | H | " | H | H | Me | Me | H |
| OMe | OMe | " | H | H | Me | iPr | H |
| OMe | OMe | " | H | H | Me | Me | H |
| OMe | OMe | " | H | H | H | Me | H |
| OMe | OMe | " | H | H | Me | Me | H |
| H | H | " | H | H | H | Me | Me |
| H | H | " | H | H | Me | Me | Me |
| Me | Me | " | H | H | Cl | Me | H |
| Me | Me | " | H | H | Me | Me | Me |
| Me | Me | " | H | H | Cl | Me | H |
| OMe | H | " | H | H | H | Me | Cl |
| OMe | H | " | H | H | Me | Me | Me |
| OMe | OMe | CH(CH$_3$)—O—CO—(CH$_2$)$_4$CH$_3$ | H | H | Cl | Me | H |
| OMe | OMe | " | H | H | Cl | Me | H |
| H | H | " | H | H | Me | Et | Me |
| H | H | " | H | H | Cl | Me | Cl |
| H | H | " | H | H | Cl | Me | Me |
| Me | Me | " | H | H | Cl | Et | Me |
| Et | Et | " | H | H | Cl | Me | Me |
| OMe | H | " | H | H | Me | Me | Cl |
| OMe | H | " | H | H | Cl | Me | Cl |
| OMe | Me | " | H | H | Cl | Me | Me |
| OMe | OMe | " | H | H | Me | Me | Cl |
| OMe | OMe | " | H | H | Cl | Me | Me |
| OEt | OEt | " | H | H | Me | Me | Cl |
| H | H | " | H | H | Me | 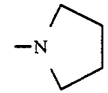 | H |
| Me | Me | " | H | H | Me | 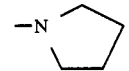 | H |
| OMe | H | " | H | H | Me | 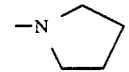 | H |
| OEt | H | " | H | H | H | —NMe$_2$ | Me |
| OMe | OMe | " | H | H | CH$_3$ | —NMe$_2$ | H |
| OEt | OEt | " | H | H | H | —NME$_2$ | Me |
| Me | H | CH(CH$_3$)—O—CO—(CH$_2$)$_4$CH$_3$ | H | H | Cl | 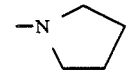 | H |
| Me | Me | " | H | H | Cl | —NMe$_2$ | H |
| OMe | H | " | H | H | Cl | —NMe$_2$ | H |
| OMe | OMe | " | H | H | Cl | —NMe$_2$ | H |
| OMe | OMe | " | H | H | Cl | 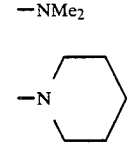 | H |
| H | H | " | H | H | Cl | —NMe$_2$ | Cl |
| Me | H | " | H | H | Cl | | Cl |

-continued

| | | | | | | | |
|---|---|---|---|---|---|---|---|
| Et | H | " | H | H | Cl | —NMe$_2$ | CH$_3$ |
| Me | Me | " | H | H | Cl | —N(pyrrolidine) | Cl |
| OCH$_2$Ph | H | " | H | H | Cl | —N(pyrrolidine) | Cl |
| OEt | H | " | H | H | Cl | —N(piperidine) | Cl |
| OMe | H | " | H | H | Cl | —NMe$_2$ | Me |
| OMe | H | " | H | H | Cl | NMe$_2$ | Cl |
| OMe | OMe | " | H | H | Cl | —N(piperidine) | Cl |
| OMe | OMe | " | H | H | Cl | —N(pyrrolidine) | Me |
| OEt | OEt | CH(CH$_3$)—O—CO—(CH$_2$O$_4$CH$_3$) | H | H | Me | —N(piperidine) | Cl |
| H | H | CH(Pr)OAc | H | H | Me | Me | OMe |
| H | H | " | H | H | Me | OEt | Cl |
| H | H | " | H | H | Me | OCH$_2$Ph | Cl |
| Me | H | " | H | H | Me | OCH$_2$CF$_3$ | Cl |
| Me | Me | " | H | H | Me | OMe | Cl |
| Me | Me | " | H | H | Me | OMe | Cl |
| Me | Me | " | H | H | Me | OEt | Cl |
| H | OMe | " | H | H | Me | OiPr | Cl |
| H | OMe | " | H | H | Me | OMe | Cl |
| H | OMe | " | H | H | Me | OEt | Cl |
| H | OMe | " | H | H | Me | OiPr | Cl |
| H | OMe | " | H | H | Me | OCH$_2$Ph | Cl |
| H | OMe | " | H | H | Me | OCH$_2$CF$_3$ | Cl |
| H | OMe | " | H | H | Me | OCH$_2$CH$_2$CF$_3$ | Cl |
| Me | OMe | " | H | H | Me | OMe | Cl |
| OMe | OMe | " | H | H | Me | OMe | Cl |
| OMe | OMe | " | H | H | Me | Opr | Cl |
| OMe | OMe | " | H | H | Me | OCH$_2$Ph | Cl |
| H | H | " | H H | Me | OCH$_2$CF$_3$ | Cl | |
| H | H | " | H | H | Cl | OMe | Cl |
| H | H | CH(Pr)OAc | H | H | Cl | OPr | Cl |
| Me | H | " | H | H | Cl | OCH$_2$Ph | Cl |
| Me | Me | " | H | H | Cl | OEt | Cl |
| Me | Me | " | H | H | Cl | OMe | Cl |
| H | OMe | " | H | H | Cl | OCH$_2$Ph | Cl |
| H | OMe | " | H | H | Cl | OMe | Cl |
| H | OMe | " | H | H | Cl | POr | Cl |
| H | OMe | " | H | H | Cl | OCH$_2$Ph | Cl |
| Me | OMe | " | H | H | Cl | OCH$_2$CF$_3$ | Cl |
| OMe | OMe | " | H | H | Cl | OMe | Cl |
| OMe | OMe | " | H | H | Cl | OMe | Cl |
| H | H | " | H | H | Cl | OEt | Cl |
| H | H | " | H | H | Cl | OCH$_2$Ph | H |
| H | H | " | H | H | Cl | OCH$_2$CF$_3$ | H |
| Me | Me | " | H | H | Cl | OCH$_2$CF$_2$CF$_3$ | H |
| Me | Me | " | H | H | Cl | OMe | H |
| OMe | H | " | H | H | Cl | OCH$_2$Ph | H |
| OMe | H | " | H | H | Cl | OMe | H |
| OMe | H | " | H | H | Cl | OCH$_2$Ph | H |
| OMe | H | " | H | H | Cl | OCH$_2$CF$_3$ | H |
| OMe | H | " | H | H | Cl | OCH$_2$CF$_2$CF$_3$ | H |

| | | |
|---|---|---|
| Me | OMe | " |
| Me | OMe | " |
| OMe | OMe | CH(Pr)OAc |
| OMe | OMe | " |
| OMe | OMe | " |
| OMe | OMe | " |
| OMe | OMe | " |
| H | H | " |
| H | H | " |
| H | H | " |
| H | H | " |
| Me | Me | " |
| Me | Me | " |
| Me | Me | " |
| Me | Me | " |
| OMe | H | " |
| OMe | H | " |
| OMe | H | " |
| OMe | H | " |
| OMe | H | " |
| OMe | OMe | " |
| OMe | OMe | " |
| OMe | OMe | CH(Pr)OAc |
| OMe | OMe | " |
| H | H | " |
| H | H | " |
| Me | Me | " |
| Me | Me | " |
| OMe | H | " |
| OMe | Me | " |
| OMe | Me | " |
| OMe | OMe | " |
| OMe | OMe | " |
| H | H | " |
| H | H | " |
| H | H | " |
| OMe | OMe | " |
| H | H | " |
| Me | H | " |
| Me | Me | " |
| OMe | H | " |
| OMe | H | CH(Pr)OAc |
| OMe | Me | " |
| OMe | OMe | " |
| OMe | OMe | " |
| OMe | OMe | " |
| H | H | " |
| H | H | " |
| Me | Me | " |
| Me | Me | " |
| Me | Me | " |
| OMe | H | " |
| OMe | H | " |
| OMe | OMe | " |
| OMe | OMe | " |
| OMe | OMe | " |
| H | H | " |
| H | H | " |
| H | H | " |
| Me | Me | " |
| Et | Et | " |
| OMe | H | " |
| OMe | H | " |
| OMe | Me | CH(Pr)OAc |
| OMe | OMe | " |
| Ome | Ome | " |
| OEt | OEt | " |
| H | H | " |
| Me | Me | " |

-continued

| | | | | |
|---|---|---|---|---|
| H | H | Cl | OEt | H |
| H | H | Cl | OCH$_2$CF$_2$CF$_3$ | H |
| H | H | Cl | OMe | H |
| H | H | Cl | OEt | H |
| H | H | Cl | OiPr | H |
| H | H | Cl | OCH$_2$Ph | H |
| H | H | Cl | OCH$_2$CF$_3$ | H |
| H | H | Cl | OMe | Me |
| H | H | Cl | OEt | Me |
| H | H | Cl | OiPr | Me |
| H | H | Cl | OCH$_2$Ph | Me |
| H | H | Cl | OCH$_2$CF$_2$CF$_3$ | Me |
| H | H | Cl | OMe | Me |
| H | H | Cl | OEt | Me |
| H | H | Cl | OCH$_2$CF$_3$ | Me |
| H | H | Cl | OCH$_2$CF$_2$CF$_3$ | Me |
| H | H | Cl | OMe | Me |
| H | H | Cl | OiPr | Me |
| H | H | Cl | OCH$_2$Ph | Me |
| H | H | Cl | OCH$_2$CF$_3$ | Me |
| H | H | Cl | OMe | Me |
| H | H | Cl | OMe | Me |
| H | H | Cl | OCH$_2$Ph | Me |
| H | H | Cl | OiPr | Cl |
| H | H | Cl | OCH$_2$Ph | Cl |
| H | H | Cl | OCH$_2$CF$_3$ | Cl |
| H | H | Me | OMe | Me |
| H | H | Me | OCH$_2$Ph | Me |
| H | H | Me | OMe | Me |
| H | H | Me | OCH$_2$CF$_3$ | Me |
| H | H | Me | OMe | Me |
| H | H | Me | Opr | Me |
| H | H | Me | OMe | Me |
| H | H | Me | O(CH$_2$)$_2$OMe | Me |
| H | H | Me | OMe | Me |
| H | H | Me | OCH$_2$CF$_3$ | Me |
| H | H | Cl | OMe | H |
| H | H | Cl | OEt | H |
| H | H | Cl | OiPr | H |
| H | H | Cl | OCH$_2$CF$_3$ | H |
| H | H | H | Me | H |
| H | H | H | iPr | H |
| H | H | H | Me | H |
| H | H | Me | iPr | H |
| H | H | H | Me | H |
| H | H | Me | Me | H |
| H | H | Me | iPr | H |
| H | H | Me | Me | H |
| H | H | H | Me | H |
| H | H | Me | Me | H |
| H | H | H | Me | Me |
| H | H | Me | Me | Me |
| H | H | Cl | Me | H |
| H | H | Me | Me | Me |
| H | H | Cl | Me | H |
| H | H | H | Me | Cl |
| H | H | Me | Me | Me |
| H | H | Cl | Me | H |
| H | H | Me | Me | Me |
| H | H | Cl | Me | H |
| H | H | Me | Et | Me |
| H | H | Cl | Me | Cl |
| H | H | Cl | Me | Me |
| H | H | Cl | Et | Me |
| H | H | Cl | Me | Me |
| H | H | Me | Me | Cl |
| H | H | Cl | Me | Cl |
| H | H | Cl | Me | Me |
| H | H | Me | Me | Cl |
| H | H | Cl | Me | Me |
| H | H | Me | Me | Cl |
| H | H | Me | Me | Cl |
| H | H | Me | 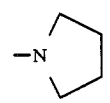 | H |
| H | H | Me | 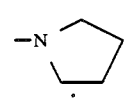 | H |

-continued

| | | | | | | | |
|---|---|---|---|---|---|---|---|
| OMe | H | " | H | H | Me | 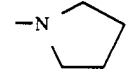 | H |
| OEt | H | " | H | H | H | —NMe$_2$ | Me |
| OMe | OMe | " | H | H | CH$_3$ | —NMe$_2$ | H |
| OEt | OEt | " | H | H | H | —NMe$_2$ | Me |
| Me | H | " | H | H | Cl | 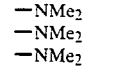 | H |
| Me | Me | " | H | H | Cl | —NMe$_2$ | H |
| OMe | H | " | H | H. | Cl | —NMe$_2$ | H |
| OMe | OMe | " | H | H | Cl | —NMe$_2$ | H |
| OMe | OMe | " | H | H | Cl | 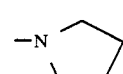 | H |
| H | H | " | H | H | Cl | —NMe$_2$ | Cl |
| Me | H | " | H | H | Cl | 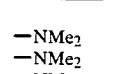 | Cl |
| Et | H | CH(Pr)OAc | H | H | Cl | —NMe$_2$ | CH$_3$ |
| Me | Me | " | H | H | Cl | 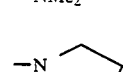 | Cl |
| OMe | H | " | H | H | Cl | —NMe$_2$ | Cl |
| OCH$_2$Ph | H | " | H | H | Cl | 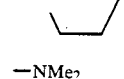 | Cl |
| OEt | H | " | H | H | Cl | 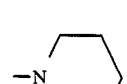 | Cl |
| OMe | H | " | H | H | Cl | —NMe$_2$ | Me |
| OMe | H | " | H | H | Cl | —NMe$_2$ | Cl |
| OMe | OMe | " | H | H | Cl | 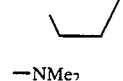 | Cl |
| OMe | OMe | " | H | H | Cl | 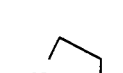 | Me |
| OEt | OEt | " | H | H | Me | 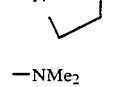 | Cl |
| H | H | CO$_2$—CH(Me)OAc | H | H | Me | OMe | Cl |
| H | H | " | H | H | Me | OEt | Cl |
| H | H | " | H | H | Me | OCH$_2$Ph | Cl |
| H | H | " | H | H | Me | OCH$_2$CF$_3$ | Cl |
| Me | H | " | H | H | Me | OMe | Cl |
| Me | Me | " | H | H | Me | OMe | Cl |
| Me | Me | " | H | H | Me | OEt | Cl |

-continued

| | | |
|---|---|---|
| Me | Me | " |
| H | OMe | CO₂—CH(Me)OAc |
| H | OMe | " |
| H | OMe | " |
| H | OMe | " |
| H | OMe | " |
| H | OMe | " |
| Me | OMe | " |
| OMe | OMe | " |
| OMe | OMe | " |
| OMe | OMe | " |
| OMe | OMe | " |
| H | H | " |
| H | H | " |
| H | H | " |
| Me | H | " |
| Me | Me | " |
| Me | Me | " |
| H | OMe | " |
| H | OMe | " |
| H | OMe | " |
| Me | OMe | " |
| OMe | OMe | CO₂CH(Me)OAc |
| OMe | OMe | " |
| H | H | " |
| H | H | " |
| H | H | " |
| Me | Me | " |
| Me | Me | " |
| OMe | H | " |
| OMe | H | " |
| OMe | H | " |
| OMe | H | " |
| Me | OMe | " |
| Me | OMe | " |
| OMe | OMe | " |
| OMe | OMe | " |
| OMe | OMe | " |
| OMe | OMe | " |
| OMe | OMe | " |
| H | H | " |
| H | H | " |
| H | H | " |
| H | H | CO₂—CH(Me)OAc |
| Me | Me | " |
| Me | Me | " |
| Me | Me | " |
| OMe | H | " |
| OMe | H | " |
| OMe | H | " |
| OMe | H | " |
| OMe | H | " |
| OME | OMe | " |
| OME | OMe | " |
| OMe | OMe | " |
| OMe | OMe | " |
| H | H | " |
| H | H | " |
| Me | Me | " |
| Me | Me | " |
| OMe | H | " |
| OMe | OMe | " |
| OMe | Me | CO₂—CH(Me)OAc |
| OMe | OMe | " |
| H | H | " |
| H | H | " |
| OMe | OMe | " |
| H | H | " |
| Me | H | " |
| Me | Me | " |
| OMe | H | " |
| OMe | H | " |

| | | | | |
|---|---|---|---|---|
| H | H | Me | OiPr | Cl |
| H | H | Me | OMe | Cl |
| H | H | Me | OEt | Cl |
| H | H | Me | OiPr | Cl |
| H | H | Me | OCH₂Ph | Cl |
| H | H | Me | OHCH₂CF₃ | Cl |
| H | H | Me | OCH₂CH₂CF₃ | Cl |
| H | H | Me | OMe | Cl |
| H | H | Me | OMe | Cl |
| H | H | Me | Opr | Cl |
| H | H | Me | OCH₂Ph | Cl |
| H | H | Me | OHC₂CF₃ | Cl |
| H | H | Cl | OMe | Cl |
| H | H | Cl | OPr | Cl |
| H | H | Cl | OCH₂Ph | Cl |
| H | H | Cl | OEt | Cl |
| H | H | Cl | OMe | Cl |
| H | H | Cl | OCH₂Ph | Cl |
| H' | H | Cl | OMe | Cl |
| H | H | Cl | OPr | Cl |
| H | H Cl | OCH₂Ph | Cl | |
| H | H | Cl | OCH₂CF₃ | Cl |
| H | H | Cl | OMe | Cl |
| H | H | Cl | OMe | Cl |
| H | H | Cl | OEt | Cl |
| H | H | Cl | OCH₂Ph | H |
| H | H | Cl | OHC₂CF₃ | H |
| H | H | Cl | OCH₂CF₂CF₃ | H |
| H | H | Cl | OMe | H |
| H | H | Cl | OCH₂Ph | H |
| H | H | Cl | OMe | H |
| H | H | Cl | OCH₂Ph | H |
| H | H | Cl | OHC₂CF₃ | H |
| H | H | Cl | OCH₂CF₂CF₃ | H |
| H | H | Cl | OEt | H |
| H | H | Cl | OCH₂CF₃ | H |
| H | H | Cl | OMe | H |
| H | H | Cl | OEt | H |
| H | H | Cl | OiPr | H |
| H | H | Cl | OCH₂Ph | H |
| H | H | Cl | OHC₂CF₃ | H |
| H | H | Cl | OMe | Me |
| H | H | Cl | OEt | Me |
| H | H | Cl | OiPr | Me |
| H | H | Cl | OCH₂Ph | Me |
| H | H | Cl | OCH₂CF₂CF₃ | Me |
| H | H | Cl | OMe | Me |
| H | H | Cl | OEt | Me |
| H | H | Cl | OCH₂CF₃ | Me |
| H | H | Cl | OCH₂CF₂CF₃ | Me |
| H | H | Cl | OMe | Me |
| H | H | Cl | OiPr | Me |
| H | H | Cl | OCH₂Ph | Me |
| H | H | Cl | OCH₂CF₃ | Me |
| H | H | Cl | OMe | Me |
| H | H | Cl | OMe | Me |
| H | H | Cl | OCH₂Ph | Me |
| H | H | Cl | OiPr | Cl |
| H | H | Cl | OCH₂Ph | Cl |
| H | H | Cl | OCH₂CF₃ | Cl |
| H | H | Me | OMe | Me |
| H | H | Me | OCH₂Ph | Me |
| H | H | Me | OMe | Me |
| H | H | Me | OCH₂CF₃ | Me |
| H | H | Me | OMe | Me |
| H | H | Me | Opr | Me |
| H | H | Me | OMe | Me |
| H | H | Me | O(CH₂)₂OMe | Me |
| H | H | Me | OMe | Me |
| H | H | Me | OCH₂CF₃ | Me |
| H | H | Cl | OMe | H |
| H | H | Cl | OEt | H |
| H | H | Cl | OiPr | H |
| H | H | Cl | OCH₂CF₃ | H |
| H | H | H | Me | H |
| H | H | H | iPr | H |
| H | H | H | Me | H |
| H | H | Me | iPr | H |
| H | H | H | Me | H |
| H | H | Me | Me | H |

-continued

| | | | | | | | |
|---|---|---|---|---|---|---|---|
| OCH₂Ph | H | " | H | H | Cl | —N(pyrrolidine) | Cl |
| OEt | H | " | H | H | Cl | —N(piperidine) | Cl |
| OMe | H | " | H | H | Cl | —NMe₂ | Me |
| OMe | H | CO₂CH(Me)OAc | H | H | Cl | —NMe₂ | Cl |
| OMe | OMe | " | H | H | Cl | —N(piperidine) | Cl |
| OMe | OMe | " | H | H | Cl | —N(pyrrolidine) | Me |
| OEt | OEt | " | H | H | Me | —N(piperidine) | Cl |
| H | H | CO₂—CH(Me)—O—CO—Pent | H | H | Me | OMe | Cl |
| H | H | " | H | H | Me | OEt | Cl |
| H | H | " | H | H | Me | OCH₂Ph | Cl |
| H | H | " | H | H | Me | OCH₂CF₃ | Cl |
| Me | H | " | H | H | Me | OMe | Cl |
| Me | Me | " | H | H | Me | OMe | Cl |
| Me | Me | " | H | H | Me | OEt | Cl |
| Me | Me | " | H | H | Me | OiPr | Cl |
| H | OMe | " | H | H | Me | OMe | Cl |
| H | OMe | " | H | H | Me | OEt | Cl |
| H | OMe | " | H | H | Me | OiPr | Cl |
| H | OMe | " | H | H | Me | OCH₂Ph | Cl |
| H | OMe | " | H | H | Me | OCH₂CF₃ | Cl |
| Me | OMe | " | H | H | Me | OCH₂CH₂CF₃ | Cl |
| OMe | OMe | CO₂—CH(Me)—O—CO—Pent | H | H | Me | OMe | Cl |
| OMe | OMe | " | H | H | Me | OMe | Cl |
| OMe | OMe | " | H | H | Me | OPr | Cl |
| OMe | OMe | " | H | H | Me | OCH₂Ph | Cl |
| OMe | OMe | " | H | H | Me | OCH₂CF₃ | Cl |
| H | H | " | H | H | Cl | OMe | Cl |
| H | H | " | H | H | Cl | OPr | Cl |
| H | H | " | H | H | Cl | OCH₂Ph | Cl |
| Me | H | " | H | H | Cl | OEt | Cl |
| Me | Me | " | H | H | Cl | OMe | Cl |
| Me | Me | " | H | H | Cl | OCH₂Ph | Cl |
| H | OMe | " | H | H | Cl | OMe | Cl |
| H | OMe | " | H | H | Cl | OPr | Cl |
| H | OMe | " | H | H | Cl | OCH₂Ph | Cl |
| H | OMe | " | H | H | Cl | OCH₂CF₃ | Cl |
| Me | OMe | " | H | H | Cl | OMe | Cl |
| OMe | OMe | " | H | H | Cl | OMe | Cl |
| OMe | OMe | " | H | H | Cl | OEt | Cl |
| H | H | " | H | H | Cl | OCH₂Ph | H |
| H | H | " | H | H | Cl | OCH₂CF₃ | H |
| H | H | " | H | H | Cl | OCH₂CF₂CF₃ | H |
| Me | Me | " | H | H | Cl | OMe | H |
| Me | Me | CO₂—CH(Me)—O—CO—Pent | H | H | Cl | OCH₂Ph | H |
| OMe | H | " | H | H | Cl | OMe | H |
| OMe | H | " | H | H | Cl | OCH₂Ph | H |
| OMe | H | " | H | H | Cl | OCH₂CF₃ | H |
| OMe | H | " | H | H | Cl | OCH₂CF₂CF₃ | H |
| Me | OMe | " | H | H | Cl | OEt | H |
| Me | OMe | " | H | H | Cl | OCH₂CF₂CF₃ | H |
| OMe | OMe | " | H | H | Cl | OMe | H |
| OMe | OMe | " | H | H | Cl | OEt | H |
| OMe | OMe | " | H | H | Cl | OiPr | H |
| OMe | OMe | " | H | H | Cl | OCH₂Ph | H |
| OMe | OMe | " | H | H | Cl | OCH₂CF₃ | H |
| H | H | " | H | H | Cl | OMe | Me |
| H | H | " | H | H | Cl | OEt | Me |

-continued

| | | | | | | | |
|---|---|---|---|---|---|---|---|
| OMe | H | " | H | H | Me | iPr | H |
| OMe | Me | " | H | H | Me | Me | H |
| OMe | OMe | " | H | H | H | Me | H |
| OMe | OMe | " | H | H | Me | Me | Me |
| OMe | OMe | " | H | H | H | Me | Me |
| H | H | " | H | H | Me | Me | Me |
| H | H | " | H | H | Cl | Me | H |
| Me | Me | " | H | H | Me | Me | Me |
| Me | Me | " | H | H | Cl | Me | H |
| Me | Me | CO$_2$—CH(Me)OAc | H | H | H | Me | Cl |
| OMe | H | " | H | H | Me | Me | Me |
| OMe | H | " | H | H | Cl | Me | H |
| OMe | OMe | " | H | H | Me | Me | Me |
| OMe | OMe | " | H | H | Cl | Me | H |
| OMe | OMe | " | H | H | Me | Et | Me |
| H | H | " | H | H | Cl | Me | Cl |
| H | H | " | H | H | Cl | Me | Me |
| H | H | " | H | H | Cl | Et | Me |
| Me | Me | " | H | H | Cl | Me | Me |
| Et | Et | " | H | H | Me | Me | Cl |
| OMe | H | " | H | H | Cl | Me | Cl |
| OMe | H | " | H | H | Cl | Me | Me |
| OMe | Me | " | H | H | Me | Me | Cl |
| OMe | OMe | " | H | H | Cl | Me | Me |
| OMe | OMe | " | H | H | Me | Me | Cl |
| OEt | OEt | " | H | H | Me | Me | Cl |
| H | H | " | H | H | Me | 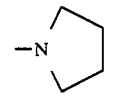 | H |
| Me | Me | " | H | H | Me | 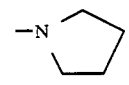 | H |
| OMe | H | " | H | H | Me | 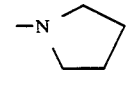 | H |
| OEt | H | CO$_2$—CH(Me)OAc | H | H | H | —NMe$_2$ | Me |
| OMe | OMe | " | H | H | CH$_3$ | —NMe$_2$ | H |
| OEt | OEt | " | H | H | H | —NMe$_2$ | Me |
| Me | H | " | H | H | Cl | 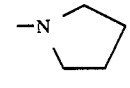 | H |
| Me | Me | " | H | H | Cl | —NMe$_2$ | H |
| OMe | H | " | H | H | Cl | —NMe$_2$ | H |
| OMe | OMe | " | H | H | Cl | —NMe$_2$ | H |
| OMe | OMe | " | H | H | Cl | 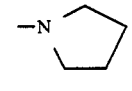 | H |
| H | H | " | H | H | Cl | —NMe$_2$ | Cl |
| Me | H | " | H | H | Cl | 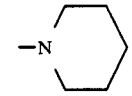 | Cl |
| Et | H | " | H | H | Cl | —NMe$_2$ | CH$_3$ |
| Me | Me | " | H | H | Cl | 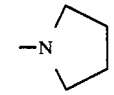 | Cl |
| OMe | H | " | H | H | Cl | —NMe$_2$ | Cl |

-continued

| | | | | | | | |
|---|---|---|---|---|---|---|---|
| H | H | " | H | H | Cl | OiPr | Me |
| H | H | " | H | H | Cl | OCH₂Ph | Me |
| H | H | " | H | H | Cl | OCH₂CF₂CF₃ | Me |
| Me | Me | " | H | H | Cl | OMe | Me |
| Me | Me | " | H | H | Cl | OEt | Me |
| Me | Me | " | H | H | Cl | OCH₂CF₃ | Me |
| Me | Me | " | H | H | Cl | OCH₂CF₂CF₃ | Me |
| OMe | H | CO₂—CH(Me)—O—CO—Pent | H | H | Cl | OMe | Me |
| OMe | H | " | H | H | Cl | OiPr | Me |
| OMe | H | " | H | H | Cl | OCH₂Ph | Me |
| OMe | H | " | H | H | Cl | OCH₂CF₃ | Me |
| OMe | Me | " | H | H | Cl | OMe | Me |
| OMe | OMe | " | H | H | Cl | OMe | Me |
| OMe | OMe | " | H | H | Cl | OCH₂Ph | Me |
| OMe | OMe | " | H | H | Cl | OiPr | Cl |
| OMe | OMe | " | H | H | Cl | OCH₂Ph | Cl |
| H | H | " | H | H | Cl | OCH₂CF₃ | Cl |
| H | H | " | H | H | Me | OMe | Me |
| Me | Me | " | H | H | Me | OCH₂Ph | Me |
| Me | Me | " | H | H | Me | OMe | Me |
| OMe | H | " | H | H | Me | OCH₂CF₃ | Me |
| OMe | H | " | H | H | Me | OMe | Me |
| OMe | Me | " | H | H | Me | Opr | Me |
| OMe | Me | " | H | H | Me | OMe | Me |
| OMe | OMe | " | H | H | Me | O(CH₂)₂OMe | Me |
| OMe | OMe | " | H | H | Me | OMe | Me |
| H | H | " | H | H | Me | OCH₂CF₃ | Me |
| H | H | CO₂CH(Me)—O—CO—Pent | H | H | Cl | OMe | H |
| H | H | " | H | H | Cl | OEt | H |
| OMe | OMe | " | H | H | Cl | OiPr | H |
| H | H | " | H | H | Cl | OCH₂CF₃ | H |
| H | H | " | H | H | H | Me | H |
| Me | H | " | H | H | H | iPr | H |
| Me | Me | " | H | H | H | Mr | H |
| Me | Me | " | H | H | Me | iPr | H |
| OMe | H | " | H | H | H | Me | H |
| OMe | H | " | H | H | Me | Me | H |
| OMe | Me | " | H | H | Me | iPr | H |
| OMe | OMe | " | H | H | H | Me | H |
| OMe | OMe | " | H | H | Me | Me | H |
| H | H | " | H | H | H | Me | Me |
| Me | Me | " | H | H | Me | Me | Me |
| Me | Me | " | H | H | Cl | Me | H |
| Me | Me | " | H | H | Me | Me | Me |
| OMe | H | " | H | H | Cl | Me | H |
| OMe | H | CO₂—CH(Me)—O—CO—Pent | H | H | H | Me | Cl |
| OMe | OMe | " | H | H | Me | Me | Me |
| OMe | OMe | " | H | H | Cl | Me | H |
| H | H | " | H | H | Me | Me | Me |
| H | H | " | H | H | Cl | Me | H |
| Me | Me | " | H | H | Me | Et | Me |
| Et | Et | " | H | H | Cl | Me | Cl |
| OMe | H | " | H | H | Cl | Me | Me |
| OMe | H | " | H | H | Cl | Et | Me |
| OMe | Me | " | H | H | Cl | Me | Me |
| OMe | OMe | " | H | H | Me | Me | Cl |
| OMe | OMe | " | H | H | Cl | Me | Cl |
| OEt | OEt | " | H | H | Me | Me | Cl |
| | | | H | H | Cl | Me | Cl |
| H | H | " | H | H | Me | —N⟨pyrrolidine⟩ | H |
| Me | Me | " | H | H | Me | —N⟨pyrrolidine⟩ | H |
| OMe | H | " | H | H | Me | —N⟨pyrrolidine⟩ | H |
| OEt | H | " | H | H | H | —NMe₂ | Me |
| OMe | OMe | CO₂—CH(Me)—O—CO—Pent | H | H | CH₃ | —NMe₂ | H |

-continued

| | | | | | | | |
|---|---|---|---|---|---|---|---|
| OEt | OEt | " | H | H | H | —NMe₂ | Me |
| Me | H | " | H | H | Cl | 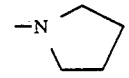 pyrrolidine | H |
| Me | Me | " | H | H | Cl | —NMe₂ | H |
| OMe | H | " | H | H | Cl | —NMe₂ | H |
| OMe | OMe | " | H | H | Cl | —NMe₂ | H |
| OMe | OMe | " | H | H | Cl | 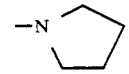 pyrrolidine | H |
| H | H | " | H | H | Cl | —NMe₂ | Cl |
| Me | H | " | H | H | Cl | 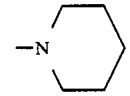 piperidine | Cl |
| Et | H | " | H | H | Cl | —NMe₂ | CH₃ |
| Me | Me | " | H | H | Cl | 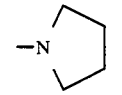 pyrrolidine | Cl |
| OMe | H | " | H | H | Cl | —NMe₂ | Cl |
| OCH₂Ph | H | " | H | H | Cl | 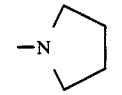 pyrrolidine | Cl |
| OEt | H | " | H | H | Cl | 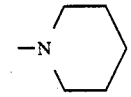 piperidine | Cl |
| OMe | H | " | H | H | Cl | —NMe₂ | Me |
| OMe | H | " | H | H | Cl | —NMe₂ | Cl |
| OMe | OMe | CO₂CH(Me)—O—CO—Pent | H | H | Cl | 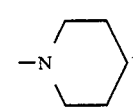 piperidine | Cl |
| OMe | OMe | " | H | H | Cl | 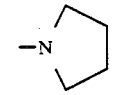 pyrrolidine | Me |
| OEt | OEt | " | H | H | Me | 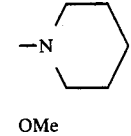 piperidine | Cl |
| H | H | Moc | H | H | Me | OMe | Cl |
| H | H | " | H | H | Me | OEt | Cl |
| H | H | " | H | H | Me | OCH₂Ph | Cl |
| H | H | " | H | H | Me | OCH₂CF₃ | Cl |
| Me | H | " | H | H | Me | OMe | Cl |
| Me | Me | " | H | H | Me | OMe | Cl |
| Me | Me | " | H | H | Me | OEt | Cl |
| Me | Me | " | H | H | Me | OiPr | Cl |
| H | OMe | " | H | H | Me | OMe | Cl |
| H | OMe | " | H | H | Me | OEt | Cl |
| H | OMe | " | H | H | Me | OiPr | Cl |
| H | OMe | " | H | H | Me | OCH₂Ph | Cl |
| H | OMe | " | H | H | Me | OCH₂CF₃ | Cl |
| H | OMe | " | H | H | Me | OCH₂CH₂CF₃ | Cl |
| Me | OMe | " | H | H | Me | OMe | Cl |
| OMe | OMe | " | H | H | Me | OMe | Cl |

-continued

| | | | | |
|---|---|---|---|---|
| OMe | OMe | Ddz | | |
| OMe | OMe | Ddz | | |
| OMe | OMe | " | | |
| H | H | " | | |
| H | H | " | | |
| Me | H | " | | |
| Me | Me | " | | |
| Me | Me | " | | |
| H | OMe | " | | |
| H | OMe | " | | |
| H | OMe | " | | |
| Me | OMe | " | | |
| OMe | OMe | " | | |
| OMe | OMe | " | | |
| H | H | Moc | | |
| H | H | " | | |
| Me | Me | " | | |
| Me | Me | " | | |
| OMe | H | " | | |
| OMe | H | " | | |
| OMe | H | Moc | | |
| OMe | H | " | | |
| Me | OMe | " | | |
| Me | OMe | " | | |
| OMe | OMe | " | | |
| OMe | OMe | " | | |
| OMe | OMe | " | | |
| OMe | OMe | " | | |
| H | H | Ddz | | |
| H | H | " | | |
| H | H | " | | |
| H | H | " | | |
| Me | Me | " | | |
| Me | Me | " | | |
| Me | Me | " | | |
| Me | Me | " | | |
| OMe | H | " | | |
| OMe | H | " | | |
| OMe | H | " | | |
| OMe | H | " | | |
| OMe | Me | Ddz | | |
| OMe | OMe | " | | |
| OMe | OMe | " | | |
| OMe | OMe | Moc | | |
| OMe | OMe | " | | |
| H | H | " | | |
| H | H | " | | |
| Me | Me | " | | |
| Me | Me | " | | |
| OMe | H | " | | |
| OMe | H | " | | |
| OMe | Me | " | | |
| OMe | Me | " | | |
| OMe | OMe | " | | |
| OMe | OMe | " | | |
| H | H | " | | |
| H | H | " | | |
| OMe | OMe | Ddz | | |
| H | H | " | | |
| Me | H | Ddz | | |
| Me | Me | " | | |
| Me | Me | " | | |
| OMe | H | " | | |
| OMe | H | " | | |
| OMe | Me | " | | |
| OMe | OMe | " | | |
| OMe | OMe | " | | |
| H | H | " | | |
| H | H | " | | |
| Me | Me | " | | |
| Me | Me | " | | |
| Me | Me | Moc | | |
| OMe | H | " | | |

| | | | | |
|---|---|---|---|---|
| H | H | Me | Opr | Cl |
| H | H | Me | OCH$_2$Ph | Cl |
| H | H | Me | OCH$_2$CF$_3$ | Cl |
| H | H | Cl | OMe | Cl |
| H | H | Cl | Opr | Cl |
| H | H | Cl | OCH$_2$Ph | Cl |
| H | H | Cl | OEt | Cl |
| H | H | Cl | OMe | Cl |
| H | H | Cl | OCH$_2$Ph | Cl |
| H | H | Cl | OMe | Cl |
| H | H | Cl | Opr | Cl |
| H | H | Cl | OCH$_2$Ph | Cl |
| H | H | Cl | OCH$_2$CF$_3$ | Cl |
| H | H | Cl | OMe | Cl |
| H | H | Cl | OEt | Cl |
| H | H | Cl | OCH$_2$Ph | H |
| H | H | Cl | OCH$_2$CF$_3$ | H |
| H | H | Cl | OCH$_2$CF$_2$CF$_3$ | H |
| H | H | Cl | OMe | H |
| H | H | Cl | OCH$_2$Ph | H |
| H | H | Cl | OMe | H |
| H | H | Cl | OCH$_2$Ph | H |
| H | H | Cl | OCH$_2$CF$_3$ | H |
| H | H | Cl | OCH$_2$CF$_2$CF$_3$ | H |
| H | H | Cl | OEt | H |
| H | H | Cl | OCH$_2$CF$_2$CF$_3$ | H |
| H | H | Cl | OMe | H |
| H | H | Cl | OEt | H |
| H | H | Cl | OiPr | H |
| H | H | Cl | OCH$_2$Ph | H |
| H | H | Cl | OCH$_2$CF$_3$ | H |
| H | H | Cl | OMe | Me |
| H | H | Cl | OEt | Me |
| H | H | Cl | OiPr | Me |
| H | H | Cl | OCH$_2$Ph | Me |
| H | H | Cl | OCH$_2$CF$_2$CF$_3$ | Me |
| H | H | Cl | OMe | Me |
| H | H | Cl | OEt | Me |
| H | H | Cl | OCH$_2$CF$_3$ | Me |
| H | H | Cl | OCH$_2$CF$_2$CF$_3$ | Me |
| H | H | Cl | OMe | Me |
| H | H | Cl | OiPr | Me |
| H | H | Cl | OCH$_2$Ph | Me |
| H | H | Cl | OCH$_2$CF$_3$ | Me |
| H | H | Cl | OMe | Me |
| H | H | Cl | OMe | Me |
| -H | H | Cl | OCH$_2$Ph | Me |
| H | H | Cl | OiPr | Cl |
| H | H | Cl | OCH$_2$Ph | Cl |
| H | H | Cl | OCH$_2$CF$_3$ | Cl |
| H | H | Me | OMe | Me |
| H | H | Me | OCH$_2$Ph | Me |
| H | H | Me | OMe | Me |
| H | H | Me | OCH$_2$CF$_3$ | Me |
| H | H | Me | OMe | Me |
| H | H | Me | Opr | Me |
| H | H | Me | OMe | Me |
| H | H | Me | O(CH$_2$)$_2$OMe | Me |
| H | H | Me | OMe | Me |
| H | H | Me | OCH$_2$CF$_3$ | Me |
| H | H | Cl | OMe | H |
| H | H | Cl | OEt | H |
| H | H | Cl | OiPr | H |
| H | H | Cl | OCH$_2$CF$_3$ | H |
| H | H | H | Me | H |
| H | H | H | iPr | H |
| H | H | H | Me | H |
| H | H | Me | iPr | H |
| H | H | H | Me | H |
| H | H | Me | Me | H |
| H | H | Me | iPr | H |
| H | H | Me | Me | H |
| H | H | H | Me | H |
| H | H | Me | Me | H |
| H | H | H | Me | Me |
| H | H | Me | Me | Me |
| H | H | Cl | Me | H |
| H | H | Me | Me | Me |
| H | H | Cl | Me | H |
| H | H | H | Me | Cl |
| H | H | Me | Me | Me |
| H | H | Cl | Me | H |

-continued

| | | | | | | | |
|---|---|---|---|---|---|---|---|
| OMe | OMe | " | H | H | Me | Me | Me |
| OMe | OMe | " | H | H | Cl | Me | H |
| OMe | OMe | " | H | H | Me | Et | Me |
| H | H | " | H | H | Cl | Me | Cl |
| H | H | " | H | H | Cl | Me | Me |
| H | H | Moc | H | H | Cl | Et | Me |
| Me | Me | " | H | H | Cl | Me | Me |
| Et | Et | " | H | H | Me | Me | Cl |
| OMe | H | " | H | H | Cl | Me | Cl |
| OMe | H | " | H | H | Cl | Me | Me |
| OMe | Me | " | H | H | Me | Me | Cl |
| OMe | OMe | " | H | H | Cl | Me | Me |
| OMe | OMe | " | H | H | Me | Me | Cl |
| OEt | OEt | Ddz | H | H | Me | Me | Cl |
| H | H | " | H | H | Me | —N(pyrrolidinyl) | H |
| Me | Me | " | H | H | Me | —N(pyrrolidinyl) | H |
| OMe | H | " | H | H | Me | —N(pyrrolidinyl) | H |
| OEt | H | " | H | H | H | —NMe$_2$ | Me |
| OMe | OMe | " | H | H | CH$_3$ | —NMe$_2$ | H |
| OEt | OEt | " | H | H | H | —NMe$_2$ | Me |
| Me | H | " | H | H | Cl | —N(pyrrolidinyl) | H |
| —NMe$_2$ | H | | | | | | |
| OMe | H | " | H | H | Cl | —NMe$_2$ | H |
| OMe | OMe | " | H | H | Cl | —NMe$_2$ | H |
| OMe | OMe | Ddz | H | H | Cl | —N(pyrrolidinyl) | H |
| H | H | " | H | H | Cl | —NMe$_2$ | Cl |
| Me | H | " | H | H | Cl | —N(piperidinyl) | Cl |
| Et | H | " | H | H | Cl | —NMe$_2$ | CH$_3$ |
| Me | Me | " | H | H | Cl | —N(pyrrolidinyl) | Cl |
| OMe | H | Moc | H | H | Cl | —NMe$_2$ | Cl |
| OCH$_2$Ph | H | " | H | H | Cl | —N(pyrrolidinyl) | Cl |
| OEt | H | " | H | H | Cl | —N(piperidinyl) | Cl |
| OMe | H | " | H | H | Cl | —NMe$_2$ | Me |
| OMe | H | " | H | H | Cl | —NMe$_2$ | Cl |

-continued

| | | | | | | | |
|---|---|---|---|---|---|---|---|
| OMe | OMe | " | H | H | Cl | −N(piperidinyl) | Cl |
| OMe | OMe | " | H | H | Cl | −N(pyrrolidinyl) | Me |
| OEt | OEt | " | H | H | Me | −N(piperidinyl) | Cl |
| H | H | −CH$_2$−O−CO−CH$_3$ | H | H | H | −O−CH$_2$−(CF$_2$)$_2$CF$_3$ | H |
| H | H | −CH$_2$−O−CO−CH$_3$ | H | H | H | −O−CH$_2$−(CF$_2$)$_2$CF$_2$H | H |
| CH$_3$ | CH$_3$ | −CH$_2$−O−CO−CH$_3$ | H | H | H | −O−CH$_2$−(CF$_2$)$_2$CF$_3$ | H |
| CH$_3$ | CH$_3$−CH$_2$−O−CO−CH$_3$ | H | H | H | −O−CH$_2$−CF$_3$ | H | |
| CH$_3$ | CH$_3$ | −CH$_2$−O−CO−CH$_3$ | H | H | H | −O−CH$_2$−CF$_2$−CF$_2$H | H |
| CH$_3$ | CH$_3$ | −CH$_2$−O−CO−CH$_3$ | H | H | H | −O−CH$_2$−CF$_2$−CF$_3$ | H |
| H | H | −CH$_2$−O−CO−CH$_3$ | H | H | H | −O−CH$_2$−CF$_3$ | CH$_3$ |
| H | H | −CH$_2$−O−CO−CH$_3$ | H | H | CH$_3$ | −O−CH$_2$−CF$_3$ | H |
| H | H | −CH$_2$−O−CO−CH$_3$ | H | H | CH$_3$ | −O−CH$_2$−CF$_2$−CF$_3$ | H |
| H | H | −CH$_2$−O−CO−CH$_3$ | H | H | CH$_3$ | −O−CH$_2$−(CF$_2$)$_2$CF$_3$ | H |
| H | H | −CH$_2$−O−CO−CH$_3$ | H | H | H | −O−CH$_2$−CF$_3$ | H |
| H | H | −CH$_2$−O−CO−CH$_3$ | H | H | H | −O−CH$_2$−CF$_2$−CF$_2$H | H |
| H | H | −CH$_2$−O−CO−CH$_3$ | H | H | H | −O−CH$_2$−CF$_2$−CF$_3$ | H |

The new compounds of the formula I and their salts have valuable pharmacological properties.

They markedly inhibit gastric acid secretion and, furthermore, have an excellent protective action on the stomach and intestines.

In this context, "protection of the stomach and intestines" is defined as the prevention and treatment of gastrointestinal disorders, in particular inflammatory gastrointestinal disorders and lesions (such as, for example, gastric ulcer, duodenal ulcer, gastritis, or irritable stomach related to hyperacidity or drugs) which may be caused by, for example, microorgansims, bacterial toxins, drugs (for example antiinflammatory and antirheumatic agents), chemicals (for example ethanol), gastric acid or stress situations.

By reason of their excellent properties, the substituted thienoimidazoles of the formula I and their pharmacologically tolerated salts are outstandingly suitable for use in human and veterinary medicine, being particularly used for the treatment and prophylaxis of disorders of the stomach and intestines and of those disorders based on excessive gastric acid secretion.

It has been found that also the colonic K$^+$-ATPase enzyme (cf. Gustin, Goodman, J. Biol. Chem. 256 [1981] 10,651–10,656) inhibited in vitro by compounds, which are obtained on treatment of the compounds of the formula I with acid (for example with NaOAc/HCl buffer with pH 4–5.5). Such conversion products can also be formed during the in vivo passage of the gastrointestinal tract. The amount of their formation depends on the substitution pattern and the pH value.

The colon-K$^+$-ATPase is believed to be of great influence on the electrolyte balance across the mucosal barrier in the colon. Colon-K$^+$-ATPase inhibitors as those mentioned above, can therefore influence said equilibrium, and they are therefore useful for treating diseases involving a disturbed electrolyte balance.

Therefore, the invention relates also to the use of compounds of the formula I, and their acid conversion products for treating diarrhoea diseases. Examples of such diseases are inflammatory intestinal diseases such as cholera, paratyphoid, tourist diarrhoea and other forms of secretory diarrhoea but also other intestinal diseases such as ulcerous colitis and regional enteritis.

The invention relates furthermore to conversion products, which are formed on treating of compounds of the formula I with acid.

Hence the invention furthermore relates to the compounds of the formula I according to the invention for use for the treatment and prophylaxis of the abovementioned disorders.

Likewise, the invention comprises the use of the compounds according to the invention for the preparation of pharmaceuticals which can be used for the treatment and prophylaxis of the abovementioned disorders.

The invention furthermore relates to pharmaceuticals which contain one or more compounds of the general formula I and/or their pharmacologically tolerated salts.

The pharmaceuticals are prepared by processes which are known per se and are familiar to the expert. The pharmacologically effective compounds (=active compounds) according to the invention are used as pharmaceuticals either as such or, preferably, in combination with suitable pharmaceutical auxiliaries, in the form of tablets, coated tablets, capsules, suppositories, emulsions, suspensions or solutions, the content of active compound advantageously being between 0.1 and 96%.

The auxiliaries which are suitable for the desired pharmaceutical formulations are familiar to the expert on the basis of his knowledge. In addition to solvents, gelforming agents, suppository bases, tableting auxiliaries and other active compound excipients it is possible to use, for example, antioxidants, dispersing agents, emulsifiers, antifoam agents, flavors, preservatives, solubilizers or colorants.

The active compounds can be administered orally or parenterally, oral administration being preferred.

In general, it has proven advantageous on oral administration in human medicine to give a daily dose of the active compound or compounds of about 0.01 to about 20 mg/kg of body weight, where appropriate in the form of several, preferably 1 to 4, individual administrations, to achieve the desired result. On parenteral administration, it is possible to use similar or (especially on intravenous administration of the active compounds) as a rule lower doses. Every expert can easily establish, on the basis of his expert knowledge, the optimal dose and mode of administration of the active compounds required in each case.

If the compounds according to the invention and/or their salts are to be used for the treatment of the abovementioned disorders, then the pharmaceutical compositions can also contain one or more pharmacologically active ingredients of other pharmaceuticals groups, such as antacids, for example aluminum hydroxide, magnesium aluminate; tranquilizers such as benzodiazepines, for example diazepam; spasmolytics, such as, for example, bietamiverine and camylofin; anticholinergics such as, for example, oxyphencylimine and phencarbamide; local anesthetics such as, for example, tetracaine and procaine; and, where appropriate, gastrin antagonists, enzymes, vitamins or amino acids.

For an oral presentation, the active compounds are mixed with the additives customary for this purpose, such as vehicles, stabilizers or inert diluents, and converted, by customary methods, into suitable forms for administration, such as tablets, coated tablets, hard gelatin capsules, aqueous, alcoholic or oily suspensions or aqueous, alcoholic or oily solutions. Examples of inert excipients which can be used are gum arabic, magnesia, magnesium carbonate, lactose, glucose or starch, in particular corn starch. This can entail preparation as either dry or moist granules. Examples of suitable oily vehicles or solvents are vegetable and animal oils, such as sunflower oil or fish liver oil.

For subcutaneous or intravenous administration, the active compounds or their physiologically tolerated salts are converted, if desired with the substances customary for this purpose, such as solubilizers, emulsifiers or further auxiliaries, into a solution, suspension or emulsion. Examples of suitable solvents for the new active compounds and the corresponding physiologically tolerated salts are: water, physiological saline solutions or alcohols, for example ethanol, propanol or glycerol, as well as sugar solutions, such as glucose or mannitol solutions, or a mixture of the various solvents mentioned.

The examples which follow are intended to illustrate the procedures according to the invention without limiting the invention to the substances mentioned here as representative.

The stated melting and decomposition points have not been corrected or standardized.

EXAMPLE 1

2-(4-Methoxy-2-picolylmercapto)-1H-thieno[3,4-d]imidazole dihydrochloride 1.6 g of 2-mercaptothieno[3,4-d]imidazole and 2 g of 4-methoxypicolyl chloride hydrochloride in 50 ml of ethanol were heated at 60° C. for about one hour and stirred at room temperature for a further 40 hours. After the crystalline substance had been filtered off, it was suspended in acetone, the mixture was stirred at room temperature for one hour, and the crystals were filtered off with suction and dried in air. Colorless crystals, melting point 330° C.

EXAMPLE 2

2-(4-Methoxy-2-picolylmercapto)-1H-thieno[3,4-d]imidazole 2.1 g of 2-(4-methoxy-2-picolylmercapto)-1H-thieno[3,4-d]imidazole dihydrochloride were suspended in 100 ml of methanol, and 1.9 g of triethylamine were then added. The resulting solution was stirred at room temperature for about one hour, and the solvent was removed by distillation. After addition of 50 ml of water, the mixture was stirred at room temperature for about one hour, and the crystals were filtered off with suction, dried and recrystallized from ethanol in the presence of active charcoal. Colorless crystals, melting point 172°–175° C.

EXAMPLE 3

2-(4Methoxy-2-picolylsulfinyl)-1H-thieno[3,4-d]imidazole 50 ml of methylene chloride were added to 0.9 g of 2-(4-methoxy-2-picolylmercapto)-1H-thieno[3,4-d]imidazole at room temperature and then, after having been cooled to 0° C., 0.64 g of 3-chloroperbenzoic acid was added in portions. The mixture was stirred for about 5 minutes while still cooling, and then 20 ml of saturated aqueous sodium bicarbonate solution were added and the mixture was stirred at room temperature for a further 10 minutes. After the organic phase had been removed and dried over sodium sulfate, the solvent was removed by distillation, the residue was stirred with a mixture of diisopropyl ether and acetone, and the crystals were filtered off and dried. Colorless crystals, melting point 142°–144° C.

EXAMPLE 4

2-(4-Methoxycarbonyl-2-picolylmercapto)-1H-thieno[3,4-d]imidazole dihydrochloride The title compound was obtained in analogy to the procedure indicated in Example 1 from 2-mercapto-6-methoxycarbonylthieno[3,4-d]imidazole and 4-methoxy-2-picolyl chloride hydrochloride.

Colorless crystals, melting point 210°–213° C.

EXAMPLE 5

6-Methoxycarbonyl-2-(4-methoxy-2-picolylmercapto)-1H-thieno[3,4-d]imidazole

The title compound was obtained in analogy to the procedure indicated in Example 2 from the compound of Example 4. Colorless crystals, melting point 156°–160° C.

EXAMPLE 6

2-(2-Picolylmercapto)-1H-thieno[3,4-d]imidazole dihydrochloride

The title compound was obtained in analogy to the procedure indicated in Example 1 from 2-picolyl chloride hydrochloride and 2-mercapto-1H-thieno[3,4-d]imidazole in isopropanol as solvent. Colorless crystals, melting point 154°–162° C.

EXAMPLE 7

4-Methoxycarbonyl-2-(2-picolylmercapto)-1H-thieno[3,4-d]imidazole hydrate hydrochloride The title compound was obtained in analogy to the procedure indicated in Example 6 from 2-mercapto-4-methoxycarbonyl-1H-thieno[3,4-d]imidazole and 2-picolyl chloride hydrochloride. Colorless crystals, melting point 204°–208° C.

EXAMPLE 8

Sodium salt of 2-(5-methyl-2-picolylsulfinyl)-1H-thieno[3,4-d]imidazole 0.036 g of sodium hydroxide was dissolved in 15 ml of methanol, and 0.24 g of 2-(5-methyl-2-picolylsulfinyl)-1H-thieno[3,4-d]imidazole was added to the solution which is then stirred at room temperature for 30 minutes. The solvent was removed by distillation under reduced pressure and the product was crystallized from ethyl acetate and filtered off. Colorless crystals, melting point 320° C.

EXAMPLE 9

2-(5-Methyl-2-picolylsulfonyl)-1H-thieno[3,4-d]imidazole

To a two-phase mixture composed of 20 ml of methylene chloride, 20 ml of saturated aqueous sodium carbonate solution and 1 g of 2-(5-methyl-2-picolylmercapto)-1H-thieno[3,4-d]imidazole was added dropwise at 0° C. a solution of 1.34 g of 3-chloroperbenzoic acid in 25 ml of methylene chloride. The mixture was stirred at 0°–5° C. for 30 minutes, the organic phase was separated off and dried over calcium chloride, and the solvent was removed by distillation. The dark residue was purified on silica gel by column chromatography using ethyl acetate/methanol =8:1 as the mobile phase and was crystallized from ethyl acetate. Colorless crystals, melting point 163° C.

EXAMPLE 10

2-(4-Methoxy-2-pyridylmethylsulfinyl)-1H-benzothieno[2,3-]imidazole (a) 3.2 g of 3-amino-2-nitrobenzo[b]thiophene were hydrogenated in 100 ml of methanol under 1 bar and at room temperature in the presence of Raney nickel until the theoretical amount of hydrogen has been absorbed, and the solvent was removed from the filtrate by distillation under reduced pressure. The resulting 2,3-diaminobenzo[b]thiophene was without further purification, dissolved in 200 ml of dichloromethane, 3.56 g of thiocarbonyldiimidazole were added, and the mixture was allowed to react at room temperature for 48 hours and then the 2-mercapto-1H-benzothieno[2,3-d]imidazole was filtered off. Crystals, melting point above 230° C.

(b) To a mixture of 1 g of 2-mercapto-1H-benzothieno[2,3-d]imidazole with 50 ml of isopropanol, 10 ml of water and 0.4 g of NaOH was added 0.97 g of 4-methoxypicolyl chloride hydrochloride, and the mixture was stirred at the reflux temperature for 2 hours and then the solvent was removed by distillation. The residue was taken up in 40 ml of water, the solution is extracted with ethyl acetate, and the solvent was removed by distillation, resulting in 2-(4-methoxy-2-picolylmercapto)-1H-benzothieno[2,3-d]imidazole as a viscous amorphous material.

(c) To a solution of 1 g of 2-(4-methoxy-2-picolylmercapto)-1H-benzothieno[2,3-d]imidazole in 75 ml of dichloromethane at room temperature was added 0.6 g of m-chloroperbenzoic acid and, after stirring for 20 minutes, saturated aqueous sodium bicarbonate solution was added, and the organic phase was separated off. After the solvent had been evaporated off under reduced pressure, crystallization was induced by treatment with a little ethyl acetate and diisopropyl ether. Colorless solid, decomposition above 90° C.

EXAMPLE 11

3-Chloro-4-methoxy-2-picoline-N-oxide

To a solution of sodium methylate, prepared from 0.51 g of sodium and 20 ml of methanol, at −10° C. were added 3.5 g of 3,4-dichloro-2-picoline-N-oxide in 20 ml of anhydrous methanol. The mixture was allowed to warm slowly to room temperature and was then heated to reflux for 1 hour. The solvent was now removed by distillation under reduced pressure, water was added to the residue, the mixture was extracted with dichloromethane, and the solvent was evaporated off. Colorless crystals from diisopropyl ether, melting point 94°–97° C.

EXAMPLE 12

3-Chloro-2-hydroxymethyl-4-methoxypyridine 5.8 g of 3-chloro-4-methoxy-2-picoline-N-oxide were dissolved in 8 ml of glacial acetic acid and, while stirring at 90° C., 14 ml of acetic anhydride were added. The mixture was heated at 110°–115° C. for 2 hours and then cooled to 80° C. and 25 ml of methanol were added dropwise. The solvent was then removed by distillation under reduced pressure, and subsequently 20 ml of water and 8 g of sodium hydroxide were added in small portions to the residue, and this mixture was heated to reflux for 2 hours. After cooling, the mixture was extracted with dichloromethane, the solvent was evaporated off, and the residue is induced to crystallize with diethyl ether. Solid, melting point 103°–105° C.

EXAMPLE 13

3-Chloro-2-chloromethyl-4-methoxypyridine hydrochloride

To a mixture of 2.6 g of 3-chloro-2-hydroxymethyl-4-methoxypyridine and 30 ml of dichloromethane at −10 to −15° C. was added dropwise a solution of 3.5 ml of thionyl chloride in 25 ml of dichloromethane, and then the mixture was stirred at room temperature for 2 hours. The solvent was evaporated off, and the residue was induced to crystallized with diethyl ether. Colorless crystals, melting point 145°–146° C.

EXAMPLE 14

(a)

3-Acetylamino-4,5-dimethoxycarbonyl-2-nitrothiophene The compound was obtained by nitration of 3-acetylamino-4,5-dimethoxythiophene with potassium nitrate/sulfuric acid or with nitric acid. Crystals, melting point 160°–165° C.

(b)

3-Amino-4,5-dimethoxycarbonyl-2-nitrothiophene

The compound from the preceding example was hydrolyzed with methanolic hydrochloric acid. Crystals, melting point 104°–107° C.

(c)

2-Mercapto-4,5-dimethoxycarbonyl-thieno[2,3-d]imidazole 2,3-Diamino-4,5-dimethoxycarbonylthiophene (0.02 mol) was obtained from the 3-amino-2-nitrothiophene derivative described above by hydrogenation with 1 bar of hydrogen at room temperature with Raney nickel as catalyst. The diamino compound thus obtained was without further purification, stirred with 0.02 mole of thiocarbonyldiimidazole in 50 ml of anhydrous dimethylacetamide at room temperature for 2 hours and then at 50° C. for 1 hour, the solvent was removed by distillation in vacuo, and the residue was induced to crystallize in isopropanol, cooling in ice. Crystals, melting point 95°–97° C.

EXAMPLE 15

1-Ethoxycarbonyl-2-(4-methoxy-2-picolylmercapto)-1H-thieno[3,4-d]imidazole

Under nitrogen, 1.4 g (5.0 mmol) of 2-(4-methoxy-2-picolylmercapto)-1H-thieno[3,4-d]imidazole were dissolved in 15 ml of anhydrous dimethylformamide, and 270 mg (6 mmol) of a 60% suspension of NaH in oil were added in portions, and the mixture was heated at 30°–40° C. for 10 minutes. Now, at 25° C., 0.5 ml (5 mmol) of ethyl chloroformate (95%) was added, during which the temperature increases to about 36° C. 30 minutes later the crystalline product was filtered off with suction and washed twice with diethyl ether. Melting point 154°–156° C. (decomposition).

EXAMPLE 16

1-Ethoxycarbonyl-2-(4-methoxy-2-picolylsulfinyl)-1H-thieno[3,4-d]imidazole

To 750 mg (2.1 mmol) of 1-ethoxycarbonyl-2-(4-methoxy-2-picolylmercapto)-1H-thieno[3,4-d]imidazole in 30 ml of methylene chloride and 25 ml of 0.5 N aqueous sodium bicarbonate solution were added dropwise, with stirring, initially 420 mg (2.1 mmol) and then a further 210 mg (1.05 mmol) of 3-chloroperbenzoic acid $CH_2Cl_2$. The organic phase was dried over $MgSO_4$ and concentrated in vacuo, and the residue was crystallized from ethyl acetate. Melting point 143° C. (decomposition).

EXAMPLE 17

1-Vinyloxycarbonyl-2-(5-methyl-2-picolylmercapto)-1H-thieno[3,4-d]imidazole

In analogy to Example 15 1.5 g of crude product were obtained from 2.1 g (8 mmol) of 2-(5-methyl-2-picolylmercapto)-1H-thieno[3,4-d]imidazole and 0.85 g (0.72 ml, 8 mmol) of vinyl chloroformate and were chromatographed on $SiO_2$ ($CH_2Cl_2$/MeOH 50:1). 1.1 g of title compound were obtained by crystallization from diisopropyl ether. Melting point 78°–80° C.

EXAMPLE 18

1-Vinyloxycarbonyl-2-(5-methyl-2-picolylsulfinyl)-1H-thieno[3,4-d]imidazole

In analogy to Example 16 0.5 g (1.5 mmol) of 1-vinyloxycarbonyl-2-(5-methyl-2-picolymercapto)-1H-thieno[3,4-d]imidazole was oxidized with m-chloroperbenzoic acid but in a 2-phase mixture composed of methylene chloride and aqueous $KH_2PO_4$/$Na_2HPO_4$ buffer solution (pH=7.5). Chromatography on $SiO_2$ is carried out with $CH_2Cl_2$/$CH_3OH$ (30:1). Melting point 162° C.

EXAMPLE 19

1-Benzyloxycarbonyl-2-(4-methoxy-2-picolylmercapto)-1H-thieno[3,4-d]imidazole 1.4 g (5 mmol) of 2-(4-methoxy-2-picolylmercapto)-1H-thieno[3,4-d]imidazole were reacted in analogy to Example 15 with 0.8 ml (5 mmol) of benzyl chloroformate (90–95%). 2.2 g of oily crude product were obtained and were chromatographed on silica gel (35–70μ) with toluene/ethyl acetate (1:5). The product crystallized from diethyl ether. Melting point 102°–104° C.

EXAMPLE 20

1-Benzyloxycarbonyl-2-(5-methyl-2-picolylmercapto)-1H-thieno[3,4-d]imidazole 2-(5-Methyl-2-picolylmercapto)-1H-thieno[3,4-d]imidazole was reacted in analogy to Example 19. The DMF were removed by distillation in vacuo, the residue was taken up in $CH_2Cl_2$, and the solution was extracted by shaking with water and dried over $MgSO_4$. After concentration, the title compound crystallized from ethyl acetate. Melting point 103°–104° C.

EXAMPLE 21

1-(4-Methoxybenzyloxycarbonyl)-2-(5-methyl-2-picolylmercapto)-1H-thieno[3,4-d]imidazole To 1.3 g (5 mmol) of 2-(5-methyl-2-picolylmercapto)-1H-thieno[3,4-d]imidazole dissolved in 15 ml of anhydrous DMF were added, under nitrogen, 275 mg (6 mmol) of sodium hydride. After the mixture had been heated at 40°–50° C. for 10 min, at room temperature 1.92 g (7.5 mmol) of 4-methoxybenzyl phenyl carbonate (prepared from 4-methoxybenzyl alcohol and phenyl chloroformate) were added, and the mixture was heated at 30°–40° C. for 10 minutes and stirred at room temperature for 1 hour. The solvent was removed by distillation in vacuo, and water was added to the residue. The oily/resinous precipitate was taken up in $CH_2Cl_2$, and the solution was dried over $MgSO_4$ and the solvent was evaporated off. The residue crystallized from diethyl ether and was recrystallized from isopropanol. Melting point 120°–121° C.

EXAMPLE 22

1-(4-Methoxybenzyloxycarbonyl)-2-(5-methyl-2-picolylsulfinyl)-1H-thieno[3,4-d]imidazole 850 mg (2 mmol) of the title compound from Example 21 were dissolved in 50 ml of $CH_2Cl_2$, and 50 ml of aqueous Na₂HPO₄/KH₂PO₄ buffer solution (pH 7.5; 7.4 ml of KH₂PO₄ solution (45.35 g/l)+42.5 ml of Na₂HPO₄ solution (59.5 g/l) were added. While stirring vigorously at room temperature, 500 mg (2.5 mmol) of m-chloroperbenzoic acid dissolved in CH₂Cl₂ were added dropwise. The organic phase was dried over MgSO₄ and concentrated, and the residue was chromatographed on silica gel using ethyl acetate. The title compound crystallized from isopropanol. Melting point 119°–120° C.

EXAMPLE 23

1-tert.-Butoxycarbonyl-2-(5-methyl-2-picolylmercapto)-1H-thieno[3,4-d]imidazole 2 g (7.7 mmol) of 2-(5-methyl-2-picolylmercapto)-1H-thieno[3,4-d]imidazole were dissolved in 25 ml of DMF, and 1.2 ml of triethylamine and 1.85 g (8.5 mmol) of di-tert.-butyl dicarbonate were added. After 2 hours a further 3 g of the dicarbonate were added, and the mixture was stirred at 70° C. for 4 hours. After DMF had been substantially evaporated off, the residue was taken up in CH₂Cl₂, and the solution was shaken with water, dried over MgSO₄ and concentrated. The residue could be crystallized from diisopropyl ether or petroleum ether. Melting point 115°–117° C.

EXAMPLE 24

1-tert.-Butoxycarbonyl-2-(5-methyl-2-picolylsulfinyl)-1H-thieno[3,4-d]imidazole 1.1 g (3 mmol) of the title compound from Example 23 were dissolved in 50 ml of CH₂Cl₂, and 50 ml of the KH₂PO₄/Na₂HPO₄ buffer solution from Example 22 were added. At 10° C. a total of 900 mg (4.5 mmol) of m-chloroperbenzoic acid in CH₂Cl₂ was added dropwise in portions until the precursor has been completely used up.

The organic phase was separated off, washed with water, dried and concentrated.

The residue was first chromatographed on silica gel using ethyl acetate. The appropriate fractions were crystallized from diethyl ether/petroleum ether, and the title compound was obtained. Melting point 98° C. (decomposition)

EXAMPLE 25

1-tert.-Butoxycarbonyl-2-(5-methyl-2-picolylsulfinyl)-1H-thieno[3,4-d]imidazole

The title compound was obtained by further elution with methanol/ethyl acetate (1:20) in the purification by column chromatography in Example 24. Melting point 127° C. (decomposition).

EXAMPLE 26

1-tert.-butoxycarbonyl-2-(4-methoxy-2-picolylmercapto)-1H-thieno[3,4-d]imidazole 1.1 g (4.0 mmol) of 2-(4-methoxy-2-picolylmercapto)-1H-thieno[3,4-d]imidazole were dissolved in 15 ml of anhydrous DMF, and 0.6 ml of triethylamine and 0.96 g (about 4.5 mmol) of di-tert.-butyl dicarbonate were added. After stirring at room temperature for 2 hours a further 0.32 g (1.5 mmol) of di-tert.-butyl dicarbonate was added.

The precipitated product was filtered off with suction; water was added to the solution, which was extracted with CH₂Cl₂ and the organic phase was dried over MgSO₄ concentrated in vacuo. The oily residue crystallized from diethyl ether. Melting point 152° C. (decomposition).

EXAMPLE 27

1-(p-Nitrophenyloxycarbonyl)-2-(5-methyl-2-picolylmercapto)-1H-thieno[3,4-d]imidazole The title compound was prepared in analogy to Example 17 from 2-(5-methyl-2-picolylmercapto)-1H-thieno[3,4-d]imidazole and p-nitrophenyl chloroformate. After working up and chromatography on silica gel using toluene/ethyl acetate (1:1), the appropriate fractions were crystallized from ethyl acetate, and the title compound was obtained. Melting point 165°–168° C.

EXAMPLE 28

1-Hydroxymethyl-2-(4-methoxy-2-picolylmercapto)1H-thieno[3,4-d]imidazole

Under a nitrogen atmosphere, 0.7 ml of 37% strength aqueous formaldehyde solution in 3 ml of acetonitrile was added dropwise to 1.6 g (5.8 mmol) of 2-(4-methoxy-2-picolylmercapto)-1H-thieno[3,4-d]imidazole dissolved in 50 of acetonitrile. The mixture was then stirred at 70° C. for 15 minutes. The solution was concentrated in vacuo, washed with water and saturated aqueous NaCl solution and dried over MgSO₄. The residue obtained after evaporation resulted, after treatment with diisopropyl ether, in a semicrystalline crude product which crystallized from ethyl acetate. Melting point 125°–127° C.

EXAMPLE 29

1-Acetoxymethyl-2-(4-methoxy-2-picolylmercapto)-1H-thieno[3,4-d]imidazole 1.3 g (4.2 mmol) of the title compound from Example 28 were dissolved in 25 ml of anhydrous pyridine, and 50 mg of 4-dimethylaminopyridine were added. Under a nitrogen atmosphere and while stirring, 6.3 ml acetic anhydride were added dropwise, and the mixture was stirred at room temperature for one hour. It was then poured onto ice water, extracted with methylene chloride, and the organic phase was dried over MgSO₄ and concentrated in vacuo. The crystalline solid was recrystallized from ethanol. Melting point 111°–113° C.

EXAMPLE 30

1-Hydroxymethyl-2-(5-methyl-2-picolylmercapto)-1H-thieno[3,4-d]imidazole

The title compound was prepared in analogy to Example 28 from 2-(5-methyl-2-picolylmercapto)-1H-thieno[3,4-d]imidazole.

EXAMPLE 31

1Acetoxymethyl-2-(5-methyl-2-picolymercapto)-1H-thieno[3,4-d]imidazole

The title compound was obtained in analogy to Example 29 from the title compound of Example 30. The resulting crude product was purified by chromatography on silica gel (ethyl acetate/toluene=2:1) and spontaneously crystallized from diisopropyl ether on scratching. Colorless crystals, melting point 87°–89° C.

EXAMPLE 32

1-Acetoxymethyl-2-(5-methyl-2-picolylsulfinyl)-1H-thieno[3,4-d]imidazole 0.67 g (2 mmol) of the title compound from Example 31 was dissolved in 30 ml of anhydrous $CH_2Cl_2$ and, under a nitrogen atmosphere, 0.6 ml (2 mmol) of titanium tetraisopropylate is added. Then at 0° C. 0.6 ml (2 mmol) of a 3M solution of tert.-butyl hydroperoxide in toluene was added dropwise. After 30 minutes the mixture was allowed to reach room temperature and was then stirred for 20 hours, water was added, the precipitated white solid was filtered off, the organic phase was dried over $MgSO_4$, the solvent was removed by distillation in vacuo, and the crude product was chromatographed on silica gel using toluene/ethyl acetate (1:5). Colorless crystals of the title compound ($R_f$=0.18) were obtained from diisopropyl ether. Melting point 104°–106° C.

EXAMPLE 33

1-Hydroxymethyl-2-(4-piperidino-3-chloro-2-picolylmercapto)-1H-thieno[3,4-d]imidazole The title compound was obtained in analogy to Example 28 from 2-(4-piperidino-3-chloro-2-picolylmercapto)-1H-thieno[3,4-d]imidazole. Melting point 132°–134° C.

EXAMPLE 34

1-Acetoxymethyl-2-(4-piperidino-3-cholor-2-picolylmercapto)-1H-thieno[3,4-d]imidazole The title compound was obtained in analogy to Example 28 from the title compound of Example 33. The crude product was chromatographed on silica gel using toluene/ethyl acetate (1:1). Melting point 169°–170° C.

EXAMPLE 35

1-(4-Methoxybenzyl)-2-(5-methyl-2-picolylmercapto)-1H-thieno[3,4-d]imidazole

The sodium salt was prepared in analogy to Example 15 from 2.6 g (10 mmol) of 2-(5-methyl-2-picolylmercapto)-1H-thieno[3,4-d]imidazole, and was alkylated with 1.7 g (11 mmol) of 4-methoxybenzyl chloride. After working up, the product was chromatographed on silica gel using $CH_2Cl_2$/methanol (50:1). The appropriate fractions were recrystallized from diethyl ether, and the title compound was obtained.
Melting point 114°–116° C.

EXAMPLE 36

1-(4-Methoxybenzyl)-2-(5-methyl-2-picolylsulfonyl)-1H-thieno[3,4-d]imidazole

The title compound from Example 35 was oxidized with 2 equivalents of m-chloroperbenzoic acid in $CH_2Cl_2$ and $Na_2HPO_4/KH_2PO_4$ buffer (as described in Example 22). The crude product was purified by chromatography (silica gel, toluene/ethyl acetate 1:4). The title compound crystallized from a little diisopropyl ether. Melting point 148°–150° C.

EXAMPLE 37

1-Acetyl-2-(5-methyl-2-picolylmercapto)-1H-thieno[3,4-d]imidazole

The title compound was obtained in analogy to Example 29 by reaction of 2-(5-methyl-2-picolylmercapto)-1H-thieno[3,4-d]imidazole with pyridine/acetic anhydride/dimethylaminopyridine. After working up, the crude product was dissolved in a little $CH_2Cl_2$ and chromatographed on silica gel using toluene/ethyl acetate (1:1). The title compound crystallized from the appropriate fractions. Melting point 139°–141° C.

EXAMPLE 38

1-(1-Acetoxyethoxycarbonyl)-2-(5-methyl-2-picolylmercapto)-1H-thieno[3,4-d]imidazole In analogy to Example 15 the sodium salt was prepared from 2.6 g (10 mmol) of 2-(5-methyl-2-picolylmercapto)-1H-thieno[3,4-d]imidazole. At −10° C. a solution of 2.7 g (10 mmol) of 1-acetoxyethyl p-nitrophenyl carbonate in DMF was added dropwise. The reaction mixture was warmed to room temperature and, after 2 hours, concentrated in vacuo, water was added to the residue, and the mixture was extracted with $CH_2Cl_2$ which dried over $MgSO_4$ and concentrated.

The residue was chromatographed on silica gel using toluene/ethyl acetate (3:1). The title compound crystallized from the appropriate fractions. Melting point 111°–113° C. In addition, a small amount of the title compound of Example 36 was obtained.

The compound in Table 2 which follows were prepared in analogous manner.

TABLE 2

| Example No. | A | T | $R^3$ | $R^4$ | $R^5$ | $R^6$ | $R^7$ | $R^8$ | $R^9$ | m.p. |
|---|---|---|---|---|---|---|---|---|---|---|
| 39. | thienyl (S) | S | H | H | H | H | $C_6H_5$–O–$CH_2$ | H | H × 2HCl | 177° C. (decomp.) |
| 40. | thienyl (S) | S | H | H | H | H | $C_6H_5$–O–$CH_2$– | H | H | 186° C. (decomp.) |
| 41. | thienyl (S) | S | H | H | H | H | $OC_2H_5$ | H | H × 2HCl | 206° C. |

TABLE 2-continued

| Example No. | A | T | R³ | R⁴ | R⁵ | R⁶ | R⁷ | R⁸ | R⁹ | m.p. |
|---|---|---|---|---|---|---|---|---|---|---|
| 42. | thiophene | S | H | H | H | H | CH₃ | H | H × 2HCl | 204° C. |
| 43. | thiophene | S | H | H | H | H | H | CH₃ | H × 2HBr | 218° C. |
| 44. | thiophene | S | H | H | H | H | H | CH₃ | H | 136° C. |
| 45. | thiophene | S | H | H | H | CH₃ | H | CH₃ | H × 2HCl | 207° C. (decomp.) |
| 46. | thiophene | SO | H | H | H | CH₃ | H | CH₃ | H | 156° C. (decomp.) |
| 47. | thiophene | S | H | H | H | CH₃ | OCH₃ | CH₃ | H | 108–112° C. |
| 48. | thiophene | S | H | H | H | CH₃ | OCH₃ | H | H | 174–177° C. |
| 49. | thiophene | SO | H | H | H | CH₃ | OCH₃ | CH₃ | H | 190° C. (decomp.) |
| 50. | thiophene | SO | H | H | H | CH₃ | OCH₃ | H | H | 145° C. (decomp.) |
| 51. | thiophene | S | H | H | H | H | H | H | H | 126–129° C. |
| 52. | thiophene | SO | H | H | H | H | H | H | H | 148–149° C. |
| 53. | thiophene | SO | H | H | H | H | OC₂H₅ | H | H | 135° C. (decomp.) |
| 54. | thiophene | S | H | H | H | CH₃ | H | H | H | >320° C. (decomp.) |

TABLE 2-continued

| Example No. | A | T | R³ | R⁴ | R⁵ | R⁶ | R⁷ | R⁸ | R⁹ | m.p. |
|---|---|---|---|---|---|---|---|---|---|---|
| 55. | 3-thienyl | SO | H | H | H | CH₃ | H | H | H | above 155° C. (decomp.) |
| 56. | 3-thienyl | SO | H | H | H | H | H | CH₃ | H | 120-123° C. |
| 57. | 2,5-dimethylthienyl | S | H | H | H | H | H | H | H × 2HCl | 330° C. |
| 58. | 2,5-dimethylthienyl | SO | H | H | H | H | H | H | H | 155-157° C. |
| 59. | 2,5-dimethylthienyl | S | H | H | H | H | OCH₃ | H | H | 217-222° C. |
| 60. | 2,5-dimethylthienyl | SO | H | H | H | H | OCH₃ | H | H | 170-174° C. |
| 61. | 3-methyl-2-(methoxycarbonyl)thienyl | SO | H | H | H | H | OCH₃ | H | H | 142° C. |
| 62. | 3-thienyl | S | H | H | H | H | morpholino | H | H × 2HCl | >320° C. |
| 63. | 2,5-dimethylthienyl | S | H | H | H | H | H | CH₃ | H × 2HCl | 250° C. |

TABLE 2-continued

| Example No. | A | T | R³ | R⁴ | R⁵ | R⁶ | R⁷ | R⁸ | R⁹ | m.p. |
|---|---|---|---|---|---|---|---|---|---|---|
| 64. | 2,5-dimethylthiophene (H₃C-thiophene-CH₃) | S | H | H | H | H | H | CH₃ | H | 164° C. (decomp.) |
| 65. | thiophene | S | H | H | —CH₂—CH₂— | | H | H | H | 147° C. |
| 66. | thiophene | SO | H | H | —CH₂—CH₂— | | H | H | H | 93° C. (decomp.) |
| 67. | thiophene | S | H | H | H | H | H | C₂H₅ | H × 2HCl | 183° C. (decomp.) |
| 68. | thiophene | SO | H | H | H | H | H | C₂H₅ | H | >85° C. (decomp.) |
| 69. | thiophene | S | H | H | H | H | —O—CH₂—C₆H₅ (—O—CH(C₆H₅)) | H | H × 2HCl | 181° C. (decomp.) |
| 70. | thiophene | SO | H | H | H | H | —O—CH₂—C₆H₅ | H | H | 174° C. (decomp.) |
| 71. | thiophene | S | H | H | H | H | —O—(CH₂)₂—O—CH₃ | H | H × 2HCl | 170° C. (decomp.) |
| 72. | thiophene | S | H | H | H | H | —O—(CH₂)₂—O—CH₃ | H | H | 114° C. |
| 73. | thiophene | SO | H | H | H | H | —O—(CH₂)₂—OCH₃ | H | H | 105° C. |
| 74. | thiophene | S | H | H | H | H | H | H | CH₃ × 2HCl | >300° C. |
| 75. | thiophene | SO | H | H | H | H | H | H | CH₃ | 125° C. |

TABLE 2-continued

| Example No. | A | T | R³ | R⁴ | R⁵ | R⁶ | R⁷ | R⁸ | R⁹ | m.p. |
|---|---|---|---|---|---|---|---|---|---|---|
| 76. | thienyl | S | H | H | H | Cl | morpholino (O,N ring) | H | H × 2HCl | 194° C. (decomp.) |
| 77. | thienyl | S | H | H | H | Cl | morpholino (O,N ring) | H | H | >90° C. |
| 78. | thienyl | S | H | H | H | Cl | OCH₃ | H | H × 2HCl | >250° C. |
| 79. | thienyl | S | H | H | H | Cl | OCH₃ | H | H | 156° C. |
| 80. | thienyl | SO | H | H | H | Cl | OCH₃ | H | H | above 160° C. (decomp.) |
| 81. | H₃CO₂C–/H₃CO₂C– substituted thienyl | S | H | H | H | H | H | H | H | 117° C. |
| 82. | CON(C₂H₅) thienyl | S | H | H | H | H | H | H | H | 102° C. |
| 83. | Cl / COOCH₃ thienyl | S | H | H | H | H | OCH₃ | H | H × 2HCl | 168° C. |
| 84. | H₃C thienyl | S | H | H | H | H | OCH₃ | H | H × 2HCl | above 188° C. |

EXAMPLE 85

2-[4-(2,2,3,3,4,4,4-heptafluorobutyloxy)-2-picolylsulfinyl]-1H-thieno[3,4-d]imidazole (a)

4-Nitro-2-picoline N-oxide

While cooling with ice, 163.5 g (1.5 mol) of 2-picoline N-oxide were introduced to 250 ml of 98% sulfuric acid. At room temperature, 250 ml of 100% nitric acid were added dropwise, and subsequently, the reaction mixture was carefully warmed up to 80° C., with stirring, and was stirred for 3 hours at this temperature. The reaction mixture was allowed to cool down to room temperature was poured in 1 l of ice and neutralized with concentrated sodium hydroxide solution, with cooling and stirring. A yellow slush of crystals precipitated, which was filtered with suction, washed with a small portion of ice water and was dried. Yield: 186 g (80% of the theory), mp.: 156° C.

(b)

4-(2,2,3,3,4,4,4-heptafluorobutyloxy)-2-picoline N-oxide 15.4 g (0.1 mol) of the compound of Example 85(a) were dissolved in 150 ml of dimethylformamide, 41.4 g (0.3 mol) of pulverised anhydrous potassium carbonate and 23 g (0.11 mol) of 96% 2,2,3,3,4,4,4-heptafluorobutanol were added, and the reaction mixture was warmed to 70° C., with stirring. After 4 hours, additional 13.9 g of pottasium carbonate were added, and the mixture was stirred for further 6 hours. The mixture was allowed to cool down to room temperature, the salts were filtered off, and were washed with a small portion of dimethylformamide.

The filtrate was concentrated in vacuo, and the residue was extracted with water/ethylacetate. The organic layer was dried with $Na_2SO_4$, concentrated, and filtered over silical gel with ethyl acetate/methanol 3:1. After concentrating the filtrate, 22.7 g (74% of the theory) of the title compound, mp.: 65° C., were isolated.

(c)

2-Chloromethyl-4-(2,2,3,3,4,4,4)-heptafluorobutyloxypyridine 49.1 g of the compound of Example 85(b) in 450 ml of acetic anhydride were stirred at 90° C. for 1 hour. A control with TLC showed the complete conversion into 2-acetyloxymethyl-4-(2,2,3,3,4,4,4)-heptafluorobutyloxypyridine.

The solvent was evaporated off in vacuo, the oily residue was dissolved in 500 ml of methanol, and a solution of 12 g of sodium hydroxide in 50 ml of water was added. After stirring at room temperature for 2 hours, TLC control showed the complete saponification of the acetate.

The solvent was removed in vacuo, the residue was dissolved in methylene chloride and washed with water. After drying with $Na_2SO_4$ the organic layer was concentrated in vacuo. The residue was dissolved in 500 ml of chloroform and 50 ml of thionyl chloride were added dropwise, with stirring. The reaction mixture was heated to reflux for 1 hour, and then allowed to cool down. The solvent was removed in vacuo, the residue was dissolved in methylene chloride, the solvent was again evaporated off, the residue was taken up in diisopropyl ether, and the title compound crystalized. Yield: 39 g (67% of the theory); mp.: 98°–101° C.

(d)

2-[4-(2,2,3,3,4,4,4-heptafluorobutyloxy)-2-picolylmercapto]-1H-thieno[3,4-d]imidazole 18.7 g of thieno[3,4-d]imidazole-2-thiol were added to a sodium methylate solution (prepared from 8.2 g of sodium and 300 ml methanol), and, during stirring, a solution of 43.8 g of the compound of Example 85(c) in 100 ml of methanol was added. After heating to reflux for 1 hour, a TLC control showed that the reaction was completed. The solvent was evaporated off in vacuo, the residue was dissolved in methylene chloride, and washed with water. The organic layer was dried with $Na_2SO_4$ and concentrated in vacuo. The residue was triturated with diisopropyl ether, filtered with suction and dried. Yield: 43 g (80% of the theory), mp.: 117° C.

(e)

2-[4-(2,2,3,3,4,4,4)-heptafluorobutyloxy)-2-picolylsulfinyl]-1H-thieno[3,4-d]imidazole 40.0 g of the mercapto compound of Example 85(d) were dissolved in 800 ml of methylene chloride, and 500 ml of an aqueous phosphate buffer (pH ≈ 7) were added. The suspension was stirred vigorously, and a solution of 20 g of 77% meta-chloroperbenzoic acid in 150 ml methylene chloride were added dropwise at 0° C. The reaction mixture was stirred at this temperatue for additional 10 minutes, and, after starch-iodine paper no longer showed the presence of the peracid, the organic layer was separated from the aqueous layer. The aqueous layer wax extracted with 100 ml of methylene chloride, the organic layers were combined, dried with $Na_2SO_4$ and concentrated in vacuo until the volume was approximately 100 ml. After addition of 800 ml of diisopropyl ether, the crystallization (which had already been started) was completed. The crystals were filtered off with suction and were dried. Yield: 32 g (76% of the theory); mp.: 140° C. (decomp.)

The following compounds were prepared in analogous manner.

EXAMPLE 86

2-[4-(2,2,3,3,4,4,5,5,-octafluoropentyloxy)-2-picolylsulfinyl]-1H-thieno[3,4-d]imidazole mp.: 116°–119° C. (decomp.).

EXAMPLE 87

2-[4-(2,2,3,3,4,4,4-heptafluorobutyloxy)-2-picolylsulfinyl]-4,6-dimethyl-1H-thieno[3,4-d]imidazole mp.: 147° C. (decomp.).

EXAMPLE 88

2-[4-(2,2,2-trifluoroethyloxy)-2-picolylsulfinyl]-4,6-dimethy-1H-thieno[3,4-d]imidazole mp.: 163°–165° C. (decomp.).

EXAMPLE 89

2-[4-(2,2,3,3-tetrafluoropropyloxy)-2-picolylsulfinyl]-4,6-dimethyl-1H-thieno[3,4-d]imidazole mp.: 144°–147° C. (decomp.).

EXAMPLE 90

2-[4-(2,2,3,3,3-pentafluoropropyloxy)-2-picolylsulfinyl]-4,6-dimethyl-1H-thieno[3,4-d]imidazole mp.: 147°–151° C. (decomp.).

EXAMPLE 91

2-[3-methyl-4-(2,2,2-trifluoroethyloxy)-2-picolylsulfinyl]-1H-thieno[3,4-d]imidazole mp.: 121° C. (decomp.).

EXAMPLE 92

2-[5-methyl-4-(2,2,2-trifluoroethyloxy)-2-picolylsulfinyl]-1H-thieno[3,4-d]imidazone mp.: 163° C. (decomp.).

EXAMPLE 93

4-[3-Methyl-(2,2,3,3,3-pentafluoropropyloxy)-2-picolylsulfinyl]-1H-thieno[3,4-d]imidazole mp.: 145° C. (decomp.).

EXAMPLE 94

2-[3-Methyl-4-(2,2,3,3,4,4,4-heptafluorobutyloxy)-2-picolylsulfinyl-1-thieno[3,4-d]imidazole mp.: 115° C. (decomp.).

EXAMPLE 95

2-[4-(2,2,2-trifluoroethyloxy)-2-picolylsulfinyl]-1H-thieno[3,4-d]imidazole mp.: 132°–136° C. (decomp.).

EXAMPLE 96

2-[4-(2,2,3,3-tetrafluoropropyloxy)-2-picolylsulfinyl]-1H-thieno[3,4-d]imidazole mp.: 152° C. (decomp.).

EXAMPLE 97

2-[4-(2,2,3,3,3-pentafluoropropyloxy)-2-picolylsulfinyl]-1H-thieno[3,4-d]imidazole mp.: 148°–152° C. (decomp.).

EXAMPLE 98

2-[4-(1,1,1,3,3,3-hexafluoroisopropyloxy)-2-picolylsulfinyl]-1H-thieno[3,4-d]imidazole

(a)

4-(1,1,1,3,3,3-Hexafluoroisopropyloxy)-2-picoline N-oxide

The title compound was obtained in analogy to Example 85(b) using potassium tert.butylate as a base.

(b)

4-(1,1,1,3,3,3-Hexafluoroisopropyloxy)-2-picoline 4.5 g (16 mmol) of the compound of Example 98(a) were dissolved in 100 ml of methanol and hydrogenated, using Raney nickel as a catalyst.

MS: m/e=259 (M+, 100%), 240 (30%), 220 (8%) 80 (77%).

(c)

2-Chloromethyl-4-(1,1,1,3,3,3-hexafluoroisopropyloxy)-pyridine hydrochloride 2.2 g (8.6 mmol) of the compound of Example 98(b) were dissolved in 50 ml tetrachloromethane, 0.56 g of dimethylformamide and 1.4 g (5.6 mmol of trichloroisocyanuric acid were added, and the reaction mixture was heated to reflux for 1 hour. A precipitate was filtered off, 30 ml of 1N hydrochloric acid in methanol were added to the filtrate and the solvent was evaporated off in vacuo. The crude product was used without further purification for the following step.

(d)

2-[4-(1,1,1,3,3,3-Hexafluoroisopropyloxy)-2-picolylmercapto]-1H-thieno[3,4-d]imidazole The title compound was obtained from the Example 98(b) and thieno[3,4-d]imidazole-2-thiol in analogy to Example 85(d)

(e)

2-[4-(1,1,1,3,3,3Hexafluoroisopropyloxy)-2-picolylsulfinyl]-1H-thieno[3,4-d]imidazole The title compound was obtained * from the compound of Example 98(e); mp.: 168°–169° C. [from diethyl ether].

* in analogy to Example 85(e).

We claim:

1. A compound of the formula I

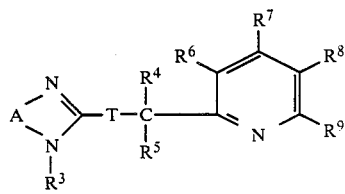

in which

A represents

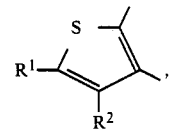

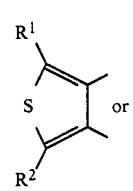

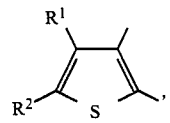

T is —S—, —S— or —SO$_2$—,

R$^1$ and R$^2$ are identical or different and are hydrogen, halogen, cyano, nitro, (C$_1$–C$_6$)-alkyl, (C$_1$–C$_6$)-hydroxyalkyl, (C$_1$–C$_6$)-alkoxy, —O(—CH$_2$)$_x$—C$_f$H$_{(2f+1-g)}$F$_g$—OCF$_2$Cl, —O—CF$_2$—CHFCl, (C$_1$–C$_6$)-alkylmercapto, (C$_1$–C$_6$)-alkylsulfinyl, (C$_1$–C$_6$)-alkylsulfonyl, (C$_1$–C$_6$)-alkylcarbonyl, (C$_1$–C$_6$)-alkoxycarbonyl, carbamoyl, N-(C$_1$–C$_4$)-alkylcarbamoyl, N,N-di-(C$_1$–C$_4$)-alkylcarbamoyl, (C$_1$–C$_6$)-alkylcarbonyloxy, (C$_3$–C$_8$)-cycloalkyl, phenyl, benzyl, phenoxy, benzyloxy, anilino, N-methyl-anilino, phenylmercapto, phenylsulfonyl, phenylsulfinyl, sulfamoyl, N-(C$_1$–C$_4$)-alkylsulfamoyl or N,N-di-(C$_1$–C$_4$)-alkylsulfamoyl or, if A is as defined above under (a) or (c), can also together be —(CH$_2$)n— or —CH=CH—CH=CH—, or said —(CH$_2$)n— or —CH=CH—CH=CH— wherein one CH$_2$ group is replaced by O, S, SO, OR SO$_2$, R$^3$ is hydrogen, (C$_1$–C$_{11}$)-alkanoyl, (C$_1$–C$_6$)-alkylcarbamoyl or another physiologically tolerated N$^{im}$ protective group which can be eliminated, R$^4$ and R$^5$ are identical or different and are hydrogen or (C$_1$–C$_3$)-alkyl, R$^6$, R$^7$, R$^8$ and R$^9$ are identical or different and are hydrogen, halogen, (C$_1$–C$_{12}$)-alkyl, (C$_1$–C$_{12}$)-alkoxy, —O[—CH$_2$]$_x$—C$_f$H$_{(2f+1-g)}$F$_g$, —NR'R", (C$_1$–C$_{12}$)-alkoxy-(C$_1$–C$_{12}$)-alkyl, (C$_1$–C$_{12}$)alkoxy-(C$_1$–C$_{12}$)-alkoxy, (C$_7$–C$_{11}$)-aralkyloxy, (C$_1$–C$_{12}$)-alkyl-mercapto, (C$_1$–C$_{12}$)-alkylsulfinyl or (C$_1$–C$_{12}$)-alkylsulfonyl, R' and R" are identical or different and denote hydrogen or (C$_1$–C$_4$)-alkyl, f is an integer from 1 to 10, g is 1 to (2f+1).

x is 0 or 1, and n is 3 or 4, or a physiologically tolerated salt thereof.

2. A compound of the formula I as claimed in claim 1, in which $R^9$ is hydrogen or a physiologically tolerated salt thereof.

3. A compound of the formula I as claimed in claim 1, in which A is as defined under (b) in claim 1 or a physiologically tolerated salt thereof.

4. A compound of the formula I as claimed in claim 1, in which T represents —SO—, or a physiologically tolerated salt thereof.

5. A compound of the formula I as claimed in claim 1, in which $R^1$ and $R^2$ are identical or different and are hydrogen, $(C_1-C_3)$-alkyl, halogen, $(C_1-C_4)$-alkoxy, or $(C_1-C_4)$-alkoxycarbonyl, $R^3$ is as defined in claim 1, $R^4$ and $R^5$ each is hydrogen, $R^6$, $R^7$, $R^8$ and $R^9$ are identical or different and are hydrogen, halogen, $-O(-CH_2)_x-C_fH_{(2f+1-g)}F_g$, $(C_1-C_3)$-alkyl, $(C_1-C_4)$-alkoxy, benzyloxy or $(C_1-C_7)$-alkoxy-$(C_1-C_3)$-alkyl, and f, g and x are as defined in claim 1, or a physiologically tolerated salt thereof.

6. A compound of the formula I as claimed in claim 1, in which $R^1$ and $R^2$ are identical or different and are hydrogen or $(C_1-C_3)$-alkyl, $R^3$ is as defined in claim 1, $R^4$ and $R^5$ each is hydrogen, $R^6$ and $R^8$ are identical or different and are hydrogen, chlorine, methyl or ethyl, $R^9$ is hydrogen, $R^7$ is hydrogen, $-O(-CH_2)_x-C_fH_{(2f+1-g)}F_g$, $(C_1-C_4)$-alkoxy, $(C_1-C_3)$-alkyl or benzyloxy, and f, g and x are as defined in claim 1, or a physiologically tolerated salt thereof.

7. A compound as claimed in claim 1, which is:
2-(2-picolylsulfinyl)-1H-thieno[3,4-d]imidazole,
2-(4-methoxy-2-picolylsulfinyl)-1H-thieno[3,4-d]imidazole,
2-(4-methoxy-3-methyl-2-picolyl-sulfinyl)-1H-thieno[3,4-d]imidazole,
2-(4-methoxy-3,5-dimethyl-2-picolylsulfinyl)-1H-thieno[3,4-d]imidazole,
2-(3-methyl-2-picolylsulfinyl)-1H-thieno[3,4-d]imidazole,
2-(5-methyl-2-picolylsulfinyl)-1H-thieno[3,4-d]imidazole,
2-(4-methyl-2-picolylsulfinyl)-1'H-thieno[3,4-d]imidazole,
2-(5-ethyl-2-picolylsulfinyl)-1H-thieno[3,4-d]imidazole,
4,6-dimethyl-2-(5-methyl-2-picolylsulfinyl)1H-thieno[3,4-d]imidazole or
2-(3-chloro-4-methoxy-2-picolylsulfinyl)-1H-thieno[3,4-d]imidazole
or a physiologically tolerated salt of said compound.

8. The compound 2-(4-(2,2,3,3,4,4,4-heptafluorobutyloxy)-2-picolylsulfinyl)-1H-thieno(3,4-d)imidazole or a physiologically tolerated salt thereof.

9. A pharmaceutical composition comprising an amount effective for the inhibition of gastric acid secretion, for the treatment of an inflammatory intestinal disease or for the treatment of diarrhoea of a compound as claimed in claim 1 or of a physiologically tolerated salt thereof, and a physiologically acceptable vehicle.

10. A method for the inhibition of gastric acid secretion which comprises administering an effective amount of a compound of the formula I as claimed in claim 1 or of a physiologically tolerated salt thereof.

11. A method for the treatment of an inflammatory intestinal disease which comprises administering an effective amount of a compound of the formula I as claimed in claim 1 or of a physiologically tolerated salt thereof.

12. A method for the treatment of diarrhoea which comprises administering an effective amount of a compound of the formula I as claimed in claim 1 or of a physiologically tolerated salt thereof.

13. A pharmaceutical composition comprising an amount effective for the inhibition of gastric acid secretion, for the treatment of an inflammatory intestinal disease or for the treatment of diarrhoea of the compound as claimed in claim 8 or of a physiologically tolerated salt thereof, and a physiologically acceptable vehicle.

14. A method for the inhibition of gastric acid secretion which comprises administering an effective amount of the compound as claimed in claim 8 or of a physiologically tolerated salt thereof.

15. A method for the treatment of an inflammatory intestinal disease which comprises administering an effective amount of the compound as claimed in claim 8 or of a physiologically tolerated salt thereof.

16. A method for the treatment of diarrhoea which comprises administering an effective amount of the compound as claimed in claim 8 or of a physiologically tolerated salt thereof.

17. A compound of the structure

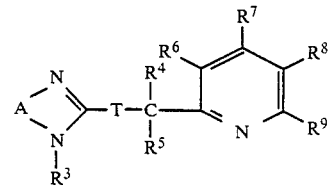

(I)

in which

A represents (b)

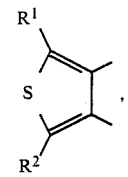

T is —SO—, $R^1$, $R^2$, $R^3$, $R^4$, $R^5$, $R^6$, $R^8$ and $R^9$ each is hydrogen, $R^7$ is $-O(-CH_2)_x-C_fH_{(2f+1-g)}F_g$, f is an integer from 1 to 10, g is 1 to $(2f+1)$, and x is 0 or 1, or a physiologically tolerated salt thereof.

18. A pharmaceutical composition comprising an amount effective for the inhibition of gastric acid secretion, for the treatment of an inflammatory intestinal disease or for the treatment of diarrhoea of a compound of the structure as claimed in claim 17 or of a physiologically tolerated salt thereof, and a physiologically acceptable vehicle.

19. A method for the inhibition of gastric acid secretion which comprises administering an effective amount of a compound of the structure as claimed in claim 17 or of a physiologically tolerated salt thereof.

20. A method for the treatment of an inflammatory intestinal disease which comprises administering an effective amount of a compound of the structure as claimed in claim 17 or of a physiologically tolerated salt thereof.

21. A method for treatment of diarrhoea which comprises administering an effective amount of a compound of the structure as claimed in claim 17 or of a physiologically tolerated salt thereof.

* * * * *

UNITED STATES PATENT AND TRADEMARK OFFICE
CERTIFICATE OF CORRECTION

PATENT NO.  : 4,845,118
DATED       : July 04, 1989
INVENTOR(S) : Hans-Jochen Lang et al It is certified that error appears in the above-identified patent and that said Letters Patent is hereby corrected as shown below:

Claim 1, column 92, line 33, change "—S—" (2nd occurence) to ---SO---.

Claim 1, column 92, line 52, change "OR" to --or--.

Claim 1, column 92, line 60, change "...[—CH$_2$]..." to --...(—CH$_2$)...--.

Claim 7, column 93, line 50, change "'H-thieno" to --H-thieno--.

Signed and Sealed this

Thirtieth Day of July, 1991

Attest:

HARRY F. MANBECK, JR.

*Attesting Officer*   Commissioner of Patents and Trademarks